US012221428B2

(12) United States Patent
Cozzi et al.

(10) Patent No.: US 12,221,428 B2
(45) Date of Patent: Feb. 11, 2025

(54) USE OF DEUTERATED EMPATHOGENS AS THERAPEUTIC AGENTS

(71) Applicant: Alexander Shulgin Research Institute, Inc., Lafayette, CA (US)

(72) Inventors: Nicholas V. Cozzi, Slinger, WI (US); Paul F. Daley, El Sobrante, CA (US)

(73) Assignee: Alexander Shulgin Research Institute, Inc., Lafayette, CA (US)

( * ) Notice: Subject to any disclaimer, the term of this patent is extended or adjusted under 35 U.S.C. 154(b) by 0 days.

(21) Appl. No.: 18/743,944

(22) Filed: Jun. 14, 2024

(65) Prior Publication Data
US 2024/0351993 A1 Oct. 24, 2024

Related U.S. Application Data

(62) Division of application No. 18/549,374, filed as application No. PCT/US2022/041279 on Aug. 23, 2022.

(60) Provisional application No. 63/236,224, filed on Aug. 23, 2021, provisional application No. 63/236,221, filed on Aug. 23, 2021.

(51) Int. Cl.
C07D 317/58 (2006.01)
A61P 25/00 (2006.01)

(52) U.S. Cl.
CPC ............ C07D 317/58 (2013.01); A61P 25/00 (2018.01)

(58) Field of Classification Search
CPC .................................................. C07D 317/58
See application file for complete search history.

(56) References Cited

U.S. PATENT DOCUMENTS

| | | | |
|---|---|---|---|
| 4,327,725 A | 5/1982 | Cortese et al. |
| 4,624,848 A | 11/1986 | Lee |
| 4,871,549 A | 10/1989 | Ueda et al. |
| 4,968,509 A | 11/1990 | Radebaugh et al. |
| 5,011,692 A | 4/1991 | Fujioka et al. |
| 5,017,381 A | 5/1991 | Maruyama et al. |
| 5,229,135 A | 7/1993 | Philippon et al. |
| 5,260,068 A | 11/1993 | Chen |
| 5,260,069 A | 11/1993 | Chen |
| 5,456,923 A | 10/1995 | Nakamichi et al. |
| 5,461,140 A | 10/1995 | Heller et al. |
| 5,508,040 A | 4/1996 | Chen |
| 5,516,527 A | 5/1996 | Curatolo |
| 5,567,441 A | 10/1996 | Chen |
| 5,622,721 A | 4/1997 | Dansereau et al. |
| 5,686,105 A | 11/1997 | Kelm et al. |
| 5,700,410 A | 12/1997 | Nakamichi et al. |
| 5,837,284 A | 11/1998 | Mehta et al. |
| 5,840,329 A | 11/1998 | Bai |
| 5,977,175 A | 11/1999 | Lin |
| 6,465,014 B1 | 10/2002 | Moroni et al. |
| 6,875,751 B2 | 4/2005 | Imbach et al. |
| 6,932,983 B1 | 8/2005 | Straub et al. |
| 7,585,851 B2 | 9/2009 | Bryant et al. |
| 7,964,580 B2 | 6/2011 | Sofia et al. |
| 10,034,832 B2 | 7/2018 | Salce, Jr. et al. |
| 2007/0190187 A1 | 8/2007 | Kneller et al. |
| 2008/0045588 A1 | 2/2008 | Gant et al. |
| 2020/0390746 A1 | 12/2020 | Rands et al. |

FOREIGN PATENT DOCUMENTS

WO 9826775 A1 6/1998

OTHER PUBLICATIONS

Lin T, et al., In vitro assessment of cytochrome P450 inhibition: Strategies for increasing LC/MS based assay throughput using a one point IC50 method and multiplexing high performance liquid chromatograpy. J Pharm Sci. 2007;96(9):2485-95.
Liu RH, Liu HC & Lin DL, Distribution of Methylenedioxymethamphetamine (MDMA) and Methylenedioxyamphetamine(MDA) in Postmortem and Antemortem Specimens, J Anal Toxicol. 2006;30(8):545-50.
Lockwood A, Steinke DT & Botts SR, Psychiatry Medication Adherence and Its Effect on Relapse Among Patients Discharged from a Veterans Affairs Posttraumatic Stress Disorder Treatment Program. Ann. Pharmacother. 2009;43:1227-32.
Luethi D & Liechti ME, Designer drugs: mechanism of action and adverse effects, Arch. Toxicol., 2020; 94, 1085-133.
Lynch T & Price A, The Effect of Cytochrome P450 Metabolism on Drug Response, Interactions, and Adverse Effects, Am Fam Physician. 2007;76(3):391-6.
Maddox JC, Levi M & Thompson C, The compliance with antidepressants in general practice, Journal of Psychopharmacology, 1994;8:48-53.
Mas M, et al. Cardiovascular and neuroendocrine effects and pharmacokinetics of 3,4-methylenedioxymethamphetamine in humans. J Pharmacol Exp. Ther 1999;290(1):136-45.
McCulloch DE, et al., A Quantitative and Qualitative Report of Psilocybin Induced Mystical-Type Experiences and Their Relation to Lasting Positive Effects. Front Pharmacol. 2022;13:841648.
Mitchell J, et al., Reply to: Caution at psychiatry's psychedelic frontier and Challenges with benchmarking of MDMA-assisted psychotherapy. Nat Med. 2021;27(6):1025-33.
Mithoefer MC, et al., A Manual for MDMA-Assisted Therapy in the Treatment of Postraumatic Stress Disorder. 2017 Ver 8.1.

(Continued)

Primary Examiner — Yong S. Chong
(74) Attorney, Agent, or Firm — CALYX LAW; Graham Pechenik

(57) ABSTRACT

Provided are deuterated analogs of MDMA, including deuterated empathogens. In some embodiments, such compounds are monoamine releasers or inhibit monoamine transporters. In some aspects, features of the compounds provide stability, such as metabolic stability, and efficacy. Also provided are methods for the preparation of deuterated empathogens and pharmaceutical compositions comprising the same. Methods of using the deuterated empathogens, alone or in combination with other therapeutic agents, are provided. In some embodiments, deuterated empathogens are used to treat CNS disorders, such as mental health conditions and neurodegenerative disorders.

20 Claims, No Drawings

(56) References Cited

OTHER PUBLICATIONS

Mithoefer MC, et al., MDMA-assisted psychotherapy for treatment of PTSD: study design and rationale for phase 3 trials based on pooled analysis of six phase 2 randomized controlled trials. Psychopharmacology (Berl). 2019;236(9):2735:45/.

Mithoefer MC, et al., The safety and efficacy of ±3,4-methylenedioxymethamphetamine-assisted psychotherapy in subjects with chronic, treatment-resistant posttraumatic stress disorder: the first randomized controlled pilot study. J. of Psychopharmacology. 2010;25(4):439-452.

Muller DM & Rentsch KM, Generation of metabolites by an automated online metabolism method using human liver microsomes with subsequent identification by LC-MS(n), and metabolism of 11 cathinones. Anal Bioanal Chem. 2012;402:2141-51.

Mundt JC, et al., Prediciton of Suicidal Behavior in Clinical Research by Lifetime Suicidal Ideation and Behavior Ascertained by the Electronic Columbia-Suicide Severity Rating Scale. The Journal of Clinical Psychiatry. 2013;74(9):887-93.

NCBI "1-(1,3-benzodioxol-5-yl)-2-(methylamino)ethanone: Pubchem CID 82075799" Pubchem 2014.

NCBI "5-[2-(Ethylamino)ethyl]-1,3 benzodioxole: Pubchem CID 19894326" Pubchem 2007.

NCBI "Butylone-d3 (hydrochloride): Pubchem CID 71312549" Pubchem 2013.

NCBI "Ethylone-d5: Pubchem CID 71316650" Pubchem 2013.

NCBI "Homarylamine: Pubchem CID 10776" Pubchem 2008.

NCBI "MDE-d5 Hydrochloride: Pubchem CID 71750306." Pubchem 2013.

NCBI "Methylone, (+)-: Pubchem CID 27281604". Pubchem 2008.

Neff KD, The Development and Validation of a Scale to Measure Self-Compassion. Self and Identity. 2003;2(3):223-50.

Nichols DE, et al., 2,3-Dihydrobenzofuran Analogues of Hallucinogenic Phenethylamines. J Med Chem, 1991; 34(1):276-81.

Nichols DE, Psychedelics, Pharmacological Reviews, 2016; 68(2):264-355.

Oehen P, et al., A Randomized Controlled Pilot Study of MDMA-Assisted Psychotherapy for Treatment of Resistant, chronic Post-Traumatic Strss Disorder (PTSD). Journal of Psychopharmacology. 2013:40-52.

PCT/US22/41279 International Search Report. Jan. 18, 2023.
PCT/US22/41279 PCT Search Strategy and Results. Jan. 18, 2023.
PCT/US22/41279 Written Opinion of the International Searching Authority. Jan. 18, 2023.

Pedersen AJ, Petersen TH & Linnet K, In vitro metabolism and pharmacokinetic studies on methylone, Drug Metab Dispos, 2013;41:1247-55.

Perez Silanes S, et al., J Heterocyclic Chem, 2001; 38(5):1025-30.

Petry et al. "Prize reinforcement contingency management for cocaine dependence: integration with group therapy in a methadone clinic." Journal of consulting and clinical psychology. 2005;73(2):354.

Poetzsch M, et al., Development of an ultrafast high throughput MALDI-triple quadrupole mass spectrometric method for the determination of 3,4-methylenedioxymethamphetamine (MDMA) in oral fluid. Drug Test Anal. 2016;8(2):235-40.

Poyatos L, et al., A comparison of acute pharmacological effects of methylone and MDMA administration in humans and oral fluid concentrations as biomarkers of exposure, Biology (Basel). 2021;10(8):788.

Ray TS, Psychedelics and the Human Receptorome, PloS one, 2010; 5(2), e9019.

Rogers G, et al., The Harmful Effects of Recreational Ecstacy: A Systematic Review of Observational Evidence. Health Technology Assessment, 2009; 13(6): iii-iv, ix-xii, 1-315.

Rohsenhow et al., Brief coping skills treatment for cocaine abuse: 12-month substance use outcomes. J. Consul. Clin. Psychol. 2000; 68(3): 515-2.

Romberg RW, et al., Differences in Binding Affinities of Mda, Mdma, Mdea, Amphetamine, Methamphetamine, and their Deuterated Analogues to Solid-Phase Extraction Cartridges. J Anal Toxicol. 2011;35(1):15-22.

Roseman et al. Quality of Acute Psychedelic Experience Predicts Therapeutic Efficacy of Psilocybin for Treatment-Resistant Depression, Front Pharmacol. 2018;8:974.

Salas J, et al., Large Posttraumatic Stress Disorder Improvement and Antidepressant Medication Adherence, J Affect Disord 2020;260:119-23.

Schenberg EE, Psychedelic-Assisted Psychotherapy: A Paradigm Shift in Psychiatric Research and Development. Neuropharmacology, 2018;9:733.

Sheehan DV, et al., The Mini-International Neuropsychiatric Interview (MINI): the development and validation of a structured diagnostic psychiatric interview for DSM-IV and ICD-10. 1998.

Shulgin & Shulgin. PiHKAL: A Chemical Love Story, 1992 Transform Press, Berkeley CA.

Shulgin & Shulgin. TiHKAL: The Continuation, 1997 Transform Press.

Simmler LD & Liechti ME, Pharmacology of MDMA-and Amphetamine-Like New Psychoactive Substances, Handbook of Experimental Pharmacology, 2018;252:143-64.

Simplício et al. Prodrugs for Amines, Molecules, 2008;13(3):519-47.

Spitzer RL et al., A Breif Measure for Assessing Generalized Anxiety Disorder: The GAD-7 Archives of Internal Medicine. 2006;166(10):1092-7.

Stotts AL, et al., Motivational Interviewing with Cocaine-Dependent Patients: A Pilot Study, J. Consul. Clin. Psychol. 2001;69(5):858-62.

Taghizadeh G, et al., Protective effects of physical exercise on MDMA-induced cognitive and mitochondrial impairment. Free Radic. Biol. Med. 2016;99:11-9.

Takano H, Cognitive Function and Monoamine Neurotransmission in Schizophrenia: Evidence From Positron Emission Tomography Studies. Front Psychiatry, 2018;9:228.

Tarawneh R, et al., Cerebrospinal Fluid Markers of Neurodegeneration and Rates of Brain Atrophy in Early Alzheimer Disease, Neurol. 2015; 72(6): 656-65.

Adams CE, et al. Contingency Management for Patients with Cooccurring Disorders: Evaluation of a Case Study and Recommendations for Practitioners, Case Reports in Psychiatry, 2012, Article ID 731638.

Azra et al. AAPA PharmaSciTech., 2009;10(1):220-6.

Barry D, Sullivans B & Petry NM, Comparable efficacy of contingency management for cocaine dependence among African American, Hispanic, and White methadone maintenance clients. Psychology of Addictive Behaviors. 2009;23(1):168.

Baumann MH, et al., The Designer Methcathinone Analogs, Mephedrone and Methylone, are Substrates for Monoamine Transporters in Brain Tissue, Neuropsychopharmacology, 2012;37(5):1192-1203.

Belal T, et al., GC—MS Evaluation of a Series of Acylated Derivatives of 3,4-Methylenedioxymethamphetamine., J Chromatogr Sci. 2009;47(5):359-64.

Berge et al., Pharmaceutical Salts. J.Pharm. Sci., 1977;66:1-19.

Bergquist MD, et al., In vivo effects of 3,4-methylenedioxymethamphetamine (MDMA) and itsdeuterated form in rodents: Drug discrimination and thermoregulation, Drug Alcohol Depend.2020;208:107850.

Bergquist MD, et al., Locomotor effects of 3,4-methylenedioxymethamphetamine (MDMA) and its deuterated form in mice: psychostimulant effects, stereotypy, and sensitization. Psychopharmacology. 2020;237:431-42.

Bolla KI, McCann UD & Ricautre GA., Memory impairment inabstinent MDMA ("Ecstasy") users. Neurology. 1998;51(6):1532-1537.

Buysse DJ. et al., The Pittsburgh Sleep Quality Index: a new instrument for psychiatric practice and research. Psychiatry Research. 1989;28(2):193-213.

Chan FK, et al., Programmed Necrosis in the Cross Talk of Cell Death and Inflammation, Annu Rev Immunol. 2015;33:79-10.

(56) References Cited

OTHER PUBLICATIONS

Chefer VI, et al., Curr Protoc Neurosci. 2009; Chapter: Unit 7.1.
Chi et al. Neuronal cell death mechanisms in major neurodegenerative diseases, Int J Mol Sci. 2018;19(10):3082.
Concheiro M, et al., Fast LC—MS/MS method for the determination of amphetamine, methamphetamine, MDA, MDMA, MDEA, MBDB and PMA in urine, Forensic Sci Int. 2007;171(1):44-51.
Costa G, et al., Activation of Antioxidant and Proteolytic Pathways in the Nigrostriatal Dopaminergic System After 3,4-Methylenedioxymethamphetamine Administration: Sex-Related Differences, Front Pharmacol. 2021;12:713486.
Crits-Cristoph P, et al., Psychosocial treatments for cocaine dependence: National Institute on Drug Abuse collaborative cocaine.
Darvesh AS, et al., In vivo brain microdialysis: advances in neuropsychopharmacology and drug discovery. Expert Opin Drug Discov. 2011; 6(2): 109-27.
Davidson JR, et al., Fragmentation pathways of odd and even-electron N-alkylated synthetic cathinones, International Journal of Mass Spectrometry. 2020;453:1-12.
Davis MH. Interpersonal Reactivity Index. 1980.
De La Torre R, et al., Human Pharmacology of MDMA: Pharmacokinetics, Metabolism, and Disposition. Therapeutic Drug Monitoring, 2004; 26(2):137-44.
Dugger BN & Dickson DW, Pathology of Neurodegenerative Diseases. Cold Spring Harb Perspect Biol. 2017;9(7):a028035.
Foster A, et al., Deuterium isotope effects in the metabolism of drugs and xenobiotics: implications for drug design, Adv. Drug Res., 1985;14:1-36.
Frau L, et al., Effect of crowding, temperature and age on glia activation and dopaminergic neurotoxicity induced by MDMA in the mouse brain, Neurotoxicology. 2016;56:127-38.
Frau L, et al., Microglial and astroglial activation by 3,4-methylenedioxymethamphetamine (MDMA) in mice depends on S(+) enantiomer and is associated with an increase in body temperature and motility. J. Neurochem., 2013;124(1):69-78.
Fukuto JM, Kumagai Y & Cho AK, Determination of the mechanism of demethylenation of (methylenedioxy) phenyl compounds by cytochrome P450 using deuterium isotope effects, Journal of Medicinal Chemistry, 1991:34(9):2871-76.
Gannes LZ, Delrio CM & Koch P, "Natural abundance variations in stable isotopes and their potential uses in animal physiological ecology." Comparative biochemistry and physiology. 1998;199(3):725-37.
Glennon R, Arylalkylamine Drugs of Abuse: An Overview of Drug Discrimination Studies, Pharmacology Biochemistry and Behavior, 1999; 64, 251-56.
Glennon R, et al., 5-HT1 and 5-HT2 binding characteristics of 1-(2,5-dimethoxy-4-bromophenyl)-2-aminopropane analogs. J Med Chem 1986;29(2):194-9.
Green BL, Trauma History Questionaire. Measurement of stress, self-report trauma, and adaptation. 1996.
Greene TA & Wuts PGM, "Protective Groups in Organic Chemistry," (Wiley, 2nd ed. 1991).
Grob CS & Grigsby J, Handbook of Medical Hallucinogens, 2021.
Harris DS, et al. "Subjective and hormonal effects of 3, 4-methylenedioxymethamphetamine (MDMA) in humans." Psychopharmacology 2002;162:396-405.
Harrison IT & Harrison S, et al., "Compendium of Synthetic Organic Methods," 1971-1996 vols. 1-8 John Wiley and Sons.
Herndon JM, et al., Glial Cell Response to 3,4-(±)-Methylenedioxymethamphetamine and Its Metabolites, Toxicological Sciences, 2014;138(1):130-8.
Heydari A, et al., Mechanism-based inactivation of CYP2D6 by methylenedioxymethamphetamine, Drug Metab Dispos. 2004;32(11):1213-7.
Holland J, et al., Ecstasy: The Complete Guide; A Comprehensive Look At The Risks And Benefits Of MDMA, 2001;82 n.2.
Huang RY, et al., Sobologram Analysis: A Comprehensive Review of Methodology and Current Research. Front in Pharmacology, 2019;10:1222.
Hung CI, Factors predicting adherence to antidepressant treatment, Curr. Opin. Psychiatry 2014;27:344-9.
Jaiswal M, et al., Nanoemulsion: an advanced mode of drug delivery system. Biotech., 2015; 3(5):123-7.
Johnson M, Richards W & Griffiths R, Human hallucinogen research: guidelines for safety. J Psychopharmacology, 2008;22: 603-20.
Kamata HT, et al., Metabolism of the recently encountered designer drug, methylone, in humans and rats. Xenobiotica, 2006;36(8):709-723.
Kedrowski SMA, et al., 1-Oxo-5-hydroxytryptamine: A Surprisingly Potent Agonist of the 5-HT3 (Serotonin) Receptor. Organic Letters, 2007; 9(17):3205-7.
Keri RP, et al., An overview of benzo[b]thiophene-based medicinal chemistry. European J Med Chem, 2017;138:1002-33.
Kish SJ, et al., Striatal serotonin is depleted in brain of a human MDMA (Ecstasy) user, Neurology, 2000;55(2):294-6.
Ko JW, et al. In vitro inhibition of the cytochrome P450 (CYP450) system by the antiplatelet drug ticlopidine: potent effect on CYP2C19 and CYP2D6, Br J Clin Pharmacol, 2000;29(4):343-451.
Kroenke K, et al., The PHQ9: Validity of a brief depression severity measure. Journal of General Internal Medicine. 2001;16(9):606-13.
Kushner DJ, Baker A & Dunstall Tg, Pharmacological uses and perspectives of heavy water and deuterated compounds, Can. J. Physiol. Pharmacol. 1999;77:79.
Leonardi ETK & Azmitia EC, MDMA (Ecstasy) Inhibition of MAO Type A and Type B: Comparisons with Fenfluramine and Fluoxetine (Prozac), Neuropsychopharmacology, 1994;10(4):231-8.
Liechti ME et al., Gender Differences in the Subjective Effects of MDMA. Psychopharmacology (Berl) 2001; 154(2):161-8.
Lin DL, et al., Effectiveness of Multiple Internal Standards: Deuterated Analogues of Methylenedioxymethamphetamine, Methylenedioxyamphetamine, Methamphetamine, and Amphetamine, J Anal Toxicol. 2004;28(8):650-4.
Teng SF, et al., Characteristics and trends of 3,4-methylenedioxymethamphetamine (MDMA) tablets found in Taiwan from 2002 to Feb. 2005, Forensic Sci Int. 2006;161(2-3):202.
Toh EA, et al., Comparison of cognitive and UHDRS measures in monitoring disease progression in Huntington's disease: a 12-month longitudinal study, Transl Neurodegener. 2014;3:15.
Tsujikawa K, et al., Urinary excretion profiles of N-hydroxy-3,4-methylenedioxymethamphetamine in rats, Xenobiotica 2011;41(7):578-84.
Uebelhack R & Schewe FH., Inhibition of platelet MAO-B by kava pyrone-enriched extract from Piper methysticum Forster (kava-kava), Pharmacopsychiatry, 1998;31(5):187-92.
Vegting Y, Reneman L & Booij J, The effects of ecstasy on neurotransmitter systems: a review on the findings of molecular imaging studies, Psychopharmacology, 2016; 233:19-20.
Vig BS, et al., Amino Acids as Promoieties in Prodrug Design and Development. Advanced Drug Delivery Reviews, 2013;65(10):1370-85.
Weyler W & Salach JI, Purification and Properties of Mitochondrial Monoamine Oxidase Type A from Human Placenta, J Biol Chem, 1985; 260(24):13199-207.
Wojcikowski J, et al., In vitro inhibition of human cytochrome P450 enzymes by the novel atypical antipsychotic drug asenapine: A prediction of possible drug—drug interactions. Pharmacol Rep. 2020;72(3)612-21.
Wong DF & Gjedde A, Monoamines: Human brain imaging, Encyclopedia of Neuroscience, 2009; 939-52.
Yamamoto et al. Metabolism of methamphetamine, amphetamine and p-hydroxymethamphetamine by rat-liver microsomal preparations in vitro. Xenobiotica, 1984;14(11)867-75.
Yamashiro T, et al., pH-dependent pyridoxine transport by SLC19A2 and SLC19A3: Implications for absorption in acidic microclimates, J Biol Chem. 2020;295(50):16998-17008.
Zhou JF, et al., 3,4-Methylenedioxymethamphetamine (MDMA) Abuse may Cause Oxidative Stress and Potential Free Radical Damage. Free Radic Res, 2003;37(5):491-7:37.

USE OF DEUTERATED EMPATHOGENS AS THERAPEUTIC AGENTS

CROSS-REFERENCE

This is a divisional application under 35 U.S.C. § 121 of U.S. application Ser. No. 18/549,374, filed Sep. 7, 2023, which is a national stage entry under 35 U.S.C. § 371 of International App. No. PCT/US22/41279, filed Aug. 23, 2022, which claims priority under PCT Article 8(1) and Rule 4.10 to U.S. Provisional App. Nos. 63/236,221 and 63/236,224, both filed Aug. 23, 2021; each of the above are incorporated by reference for all purposes as if fully set forth herein

FIELD OF THE INVENTION

The present disclosure relates in some aspects to deuterated empathogen compounds, including analogs of 3,4-methylenedioxymethamphetamine (MDMA) and 3,4-methylenedioxymethcathinone (methylone). In some aspects, the disclosure further relates to methods of synthesizing the compounds, compositions containing the compounds, and methods of using such compounds, including their administration to subjects. In some aspects, features of the compounds include enhanced metabolic stability, which prolongs duration of action and reduces formation of, and thereby exposure to, toxic metabolites of MDMA, such as 3,4-methylenedioxyamphetamine (MDA).

BACKGROUND OF THE INVENTION

The enormous public health burden of mental health disorders, combined with the shortcomings of currently available treatments, reveal the necessity of developing novel alternative treatments, especially those which minimize side effects and optimize efficacy.

One alternative treatment being developed for mental health disorders is MDMA, which has received FDA Breakthrough Therapy designation and is on track for approval as a medicine, to be provided together with psychotherapy. However, MDMA and other known empathogens have numerous drawbacks. Disclosed herein are various therapeutic empathogens including those which will have enhanced metabolic stability, reduced toxicity, and other improvements on prior art compounds, and which will meet the needs for additional alternative treatments.

INCORPORATION BY REFERENCE

Each patent, publication, and non-patent literature cited in the application is hereby incorporated by reference in its entirety as if each was incorporated by reference individually. Unless specifically stated otherwise, reference to any document herein is not to be construed as an admission that the document referred to or any underlying information in the document is prior art in any jurisdiction, or forms part of the common general knowledge in the art.

BRIEF SUMMARY OF THE INVENTION

The following presents a simplified summary of some embodiments of the invention in order to provide a basic understanding of the invention. This summary is not an extensive overview of the invention. It is not intended to identify key or critical elements of the invention or to delineate the scope of the invention. Its sole purpose is to present some embodiments of the invention in a simplified form as a prelude to the more detailed description that is presented later.

In some aspects, provided are compounds of Formula (I):

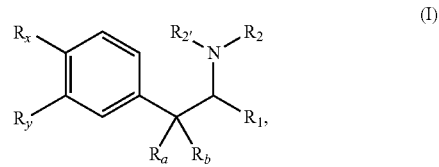

wherein:
$R_1$ is hydrogen or $C_1$-$C_6$ alkyl; and
$R_2$ and $R_{2'}$ are each independently a deuterated $C_1$-$C_6$ alkyl; or
$R_2$ is H and $R_{2'}$ is a deuterated $C_1$-$C_6$ alkyl; or
$R_2$ and $R_{2'}$ are taken together to form a deuterated 4- to 8-membered heterocyclyl;
$R_a$ and $R_b$ are each independently hydrogen, —OH, or $C_1$-$C_6$ alkoxy; or
$R_a$ and $R_b$ are taken together to form =O; and
$R_x$ and $R_y$ are taken together as —OCH=CH—, —CH=CHO—, —OCH$_2$O—, —SCH=CH—, —CH=CHS—, —SCH$_2$S—, —SCH$_2$O—, —OCH$_2$S—, —NHCH=CH—, —CH=CHNH—, —NHCH$_2$NH—, —NHCH$_2$O—, —OCH$_2$NH—, —NHCH$_2$S—, or —SCH$_2$NH—;

or a pharmaceutically acceptable salt, prodrug, hydrate, or solvate thereof;

provided that the compound is not

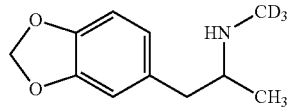

(MDMA-d3).

In some aspects, provided are compounds of Formula (II):

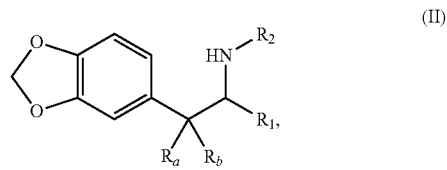

wherein: J
$R_1$ is hydrogen, —CH$_3$, or —CH$_2$CH$_3$; and
$R_2$ is —CD$_3$, —CHD$_2$, —CH$_2$D, —CH$_2$CD$_3$, —CH$_2$CHD$_2$, —CH$_2$CH$_2$D, —CHDCD$_3$, —CHDCHD$_2$, —CHDCH$_2$D, —CD$_2$CD$_3$, —CD$_2$CHD$_2$, or —CD$_2$CH$_2$D; and
$R_a$ and $R_b$ are each independently hydrogen, —OH, or $C_1$-$C_6$ alkoxy; or
$R_a$ and $R_b$ are taken together to form =O;

or a pharmaceutically acceptable salt, prodrug, hydrate, or solvate thereof.

In some embodiments, the compound has the structure of Formula (III):

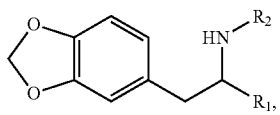

(III)

wherein R₁ is hydrogen, —CH₃, or —CH₂CH₃; and
R₂ is —CD₃, —CHD₂, —CH₂D, —CH₂CD₃, —CH₂CHD₂, —CH₂CH₂D, —CHDCD₃, —CHDCHD₂, —CHDCH₂D, —CD₂CD₃, —CD₂CHD₂, or —CD₂CH₂D;

or a pharmaceutically acceptable salt, prodrug, hydrate, or solvate thereof.

In some embodiments, the compound is of Formula (IIIA):

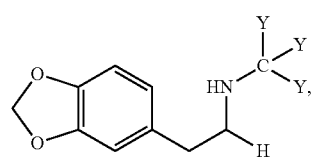

(IIIA)

wherein each Y is independently protium (H) or deuterium (D), and wherein at least one Y is deuterium (D) and the remaining Ys are protium (H);

or a pharmaceutically acceptable salt, prodrug, hydrate, or solvate thereof.

In some embodiments, the compound is of Formula (IIIB):

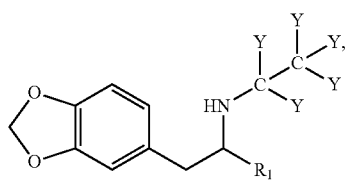

(IIIB)

wherein each Y is independently protium (H) or deuterium (D), and wherein at least one Y is deuterium (D) and the remaining Ys are protium (H);

or a pharmaceutically acceptable salt, prodrug, hydrate, or solvate thereof.

In some embodiments, the compound is of Formula (IIIC):

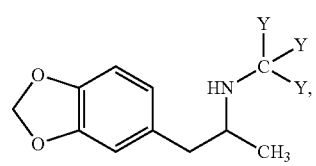

(IIIC)

wherein each Y is independently protium (H) or deuterium (D), and wherein at least one Y is deuterium (D) and the remaining Ys are protium (H);

or a pharmaceutically acceptable salt, prodrug, hydrate, or solvate thereof.

In some embodiments, the compound is of Formula (IIID):

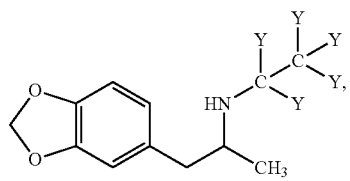

(IIID)

wherein each Y is independently protium (H) or deuterium (D), and wherein at least one Y is deuterium (D) and the remaining Ys are protium (H);

or a pharmaceutically acceptable salt, prodrug, hydrate, or solvate thereof.

In some embodiments, the compound is of Formula (IIIE):

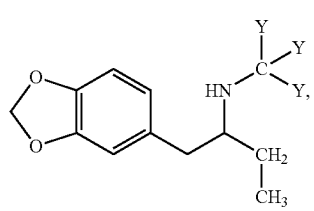

(IIIE)

wherein each Y is independently protium (H) or deuterium (D), and wherein at least one Y is deuterium (D) and the remaining Ys are protium (H);

or a pharmaceutically acceptable salt, prodrug, hydrate, or solvate thereof.

In some embodiments, the compound is of Formula (IIIF):

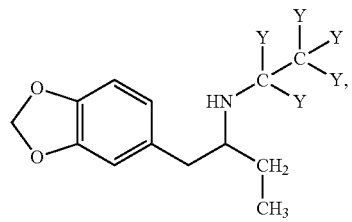

(IIIF)

wherein each Y is independently protium (H) or deuterium (D), and wherein at least one Y is deuterium (D) and the remaining Ys are protium (H);

or a pharmaceutically acceptable salt, prodrug, hydrate, or solvate thereof.

In some embodiments, the compound has the structure of Formula (IV):

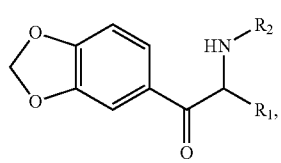

(IV)

wherein R₁ is hydrogen, —CH₃, or —CH₂CH₃; and
R₂ is —CD₃, —CHD₂, —CH₂D, —CH₂CD₃, —CH₂CHD₂, —CH₂CH₂D, —CHDCD₃, —CHDCHD₂, —CHDCH₂D, —CD₂CD₃, —CD₂CHD₂, or —CD₂CH₂D;

or a pharmaceutically acceptable salt, prodrug, hydrate, or solvate thereof.

In some embodiments, the compound is of Formula (IVA):

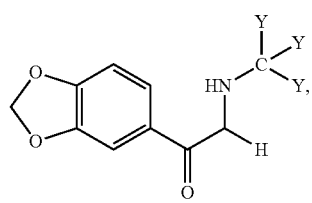
(IVA)

wherein each Y is independently protium (H) or deuterium (D), and wherein at least one Y is deuterium (D) and the remaining Ys are protium (H);

or a pharmaceutically acceptable salt, prodrug, hydrate, or solvate thereof.

In some embodiments, the compound is of Formula (IVB):

(IVB)

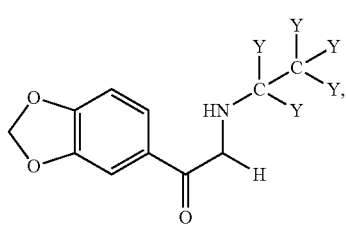

wherein each Y is independently protium (H) or deuterium (D), and wherein at least one Y is deuterium (D) and the remaining Ys are protium (H);

or a pharmaceutically acceptable salt, prodrug, hydrate, or solvate thereof.

In some embodiments, the compound is of Formula (IVC):

(IVC)

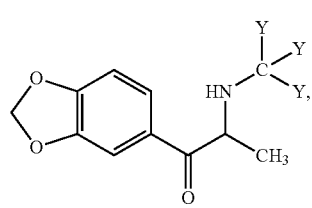

wherein each Y is independently protium (H) or deuterium (D), and wherein at least one Y is deuterium (D) and the remaining Ys are protium (H);

or a pharmaceutically acceptable salt, prodrug, hydrate, or solvate thereof.

In some embodiments, the compound is of Formula (IVD):

(IVD)

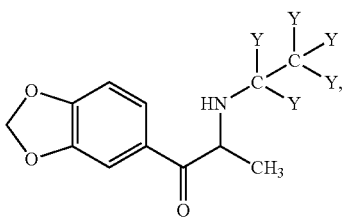

wherein each Y is independently protium (H) or deuterium (D), and wherein at least one Y is deuterium (D) and the remaining Ys are protium (H);

or a pharmaceutically acceptable salt, prodrug, hydrate, or solvate thereof.

In some embodiments, the compound is of Formula (IVE):

(IIE)

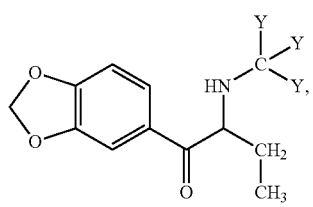

wherein each Y is independently protium (H) or deuterium (D), and wherein at least one Y is deuterium (D) and the remaining Ys are protium (H);

or a pharmaceutically acceptable salt, prodrug, hydrate, or solvate thereof.

In some embodiments, the compound is of Formula (IVF):

(IVF)

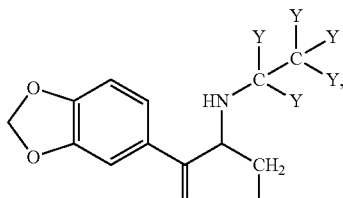

wherein each Y is independently protium (H) or deuterium (D), and wherein at least one Y is deuterium (D) and the remaining Ys are protium (H);

or a pharmaceutically acceptable salt, prodrug, hydrate, or solvate thereof.

In some aspects, provided is a compound selected from the group consisting of:

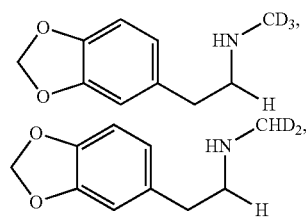

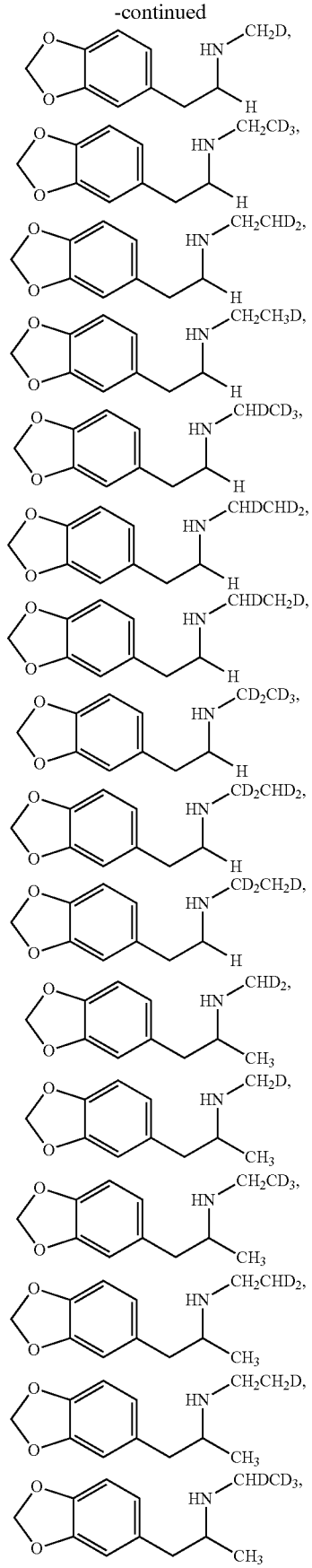
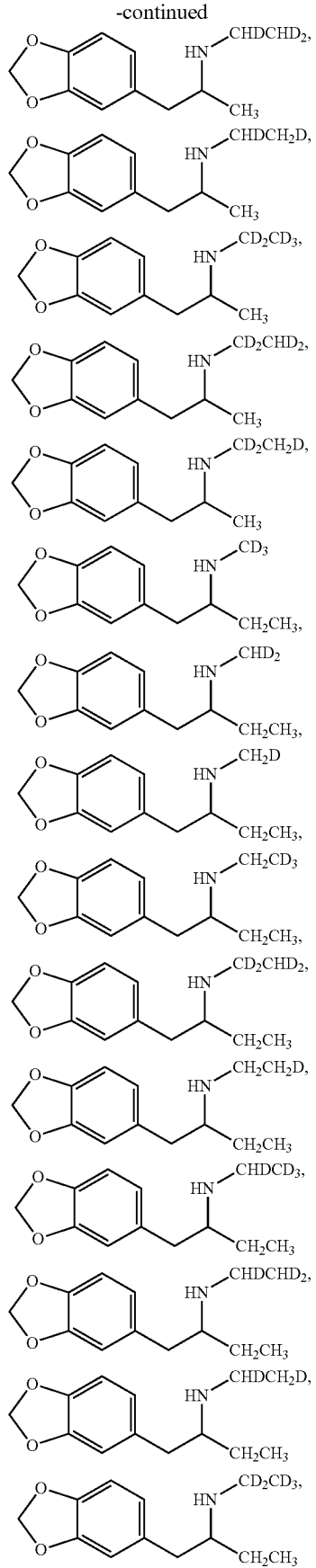

-continued
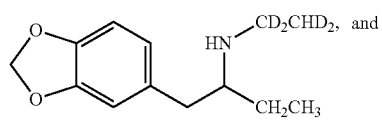, and
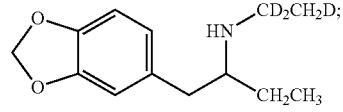;
or a pharmaceutically acceptable salt, prodrug, hydrate, or solvate thereof.
In some aspects, provided is a compound selected from the group consisting of:
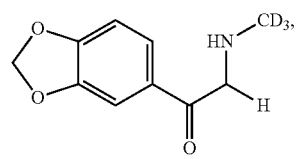
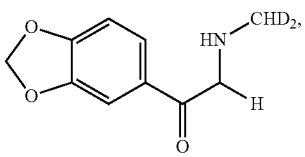
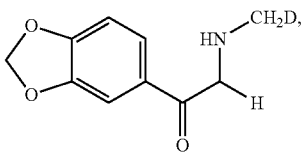
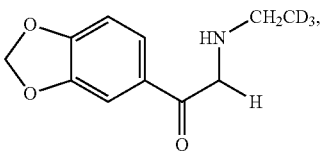
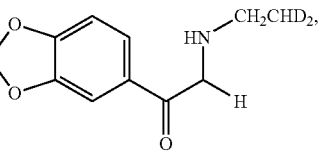
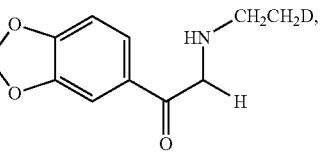
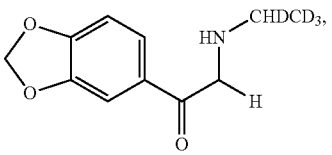
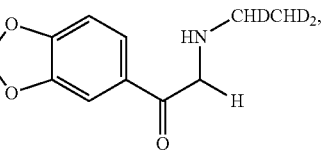
-continued
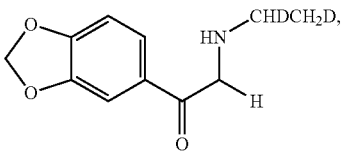
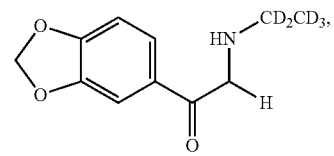
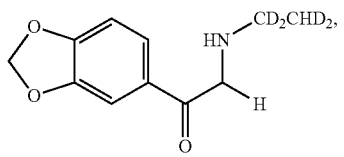
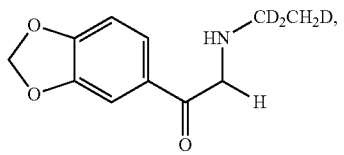
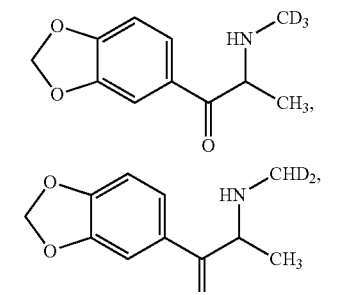
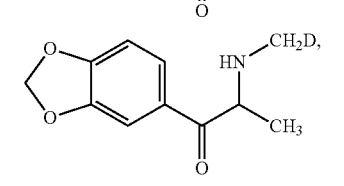
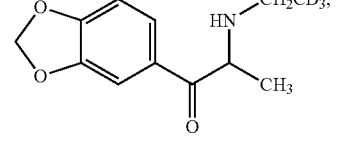
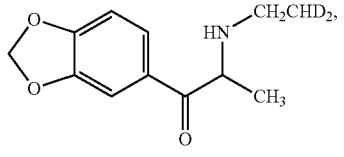
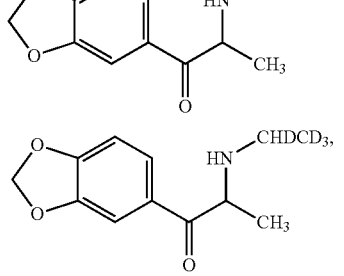

-continued

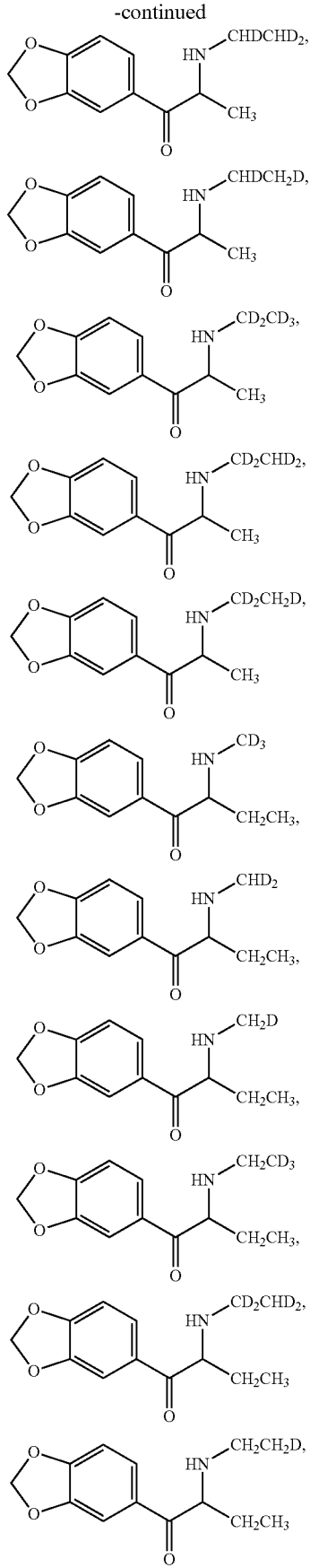

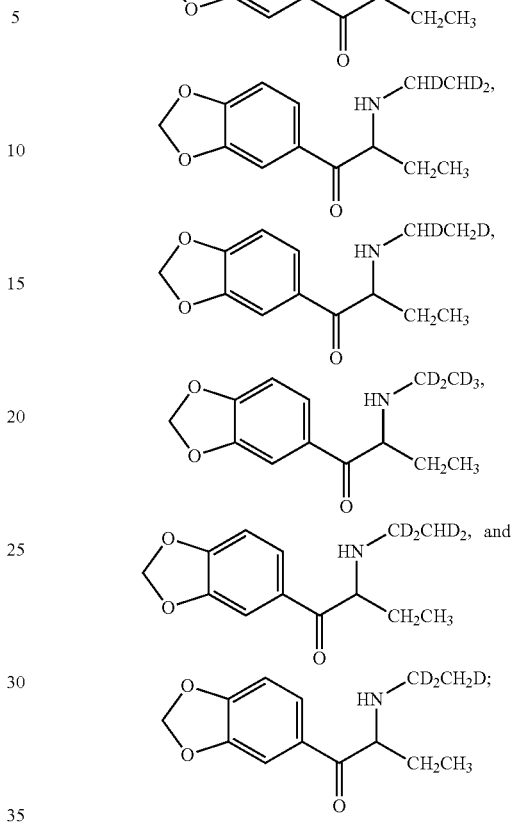

or a pharmaceutically acceptable salt, prodrug, hydrate, or solvate thereof.

In some embodiments, the compound has reduced intrinsic clearance relative to a corresponding non-substituted (undeuterated) compound. In some embodiments, intrinsic clearance is reduced by at least 5%, 10%, 25%, 50%, 75%, 100%, 150%, or 200%. In some embodiments, the compound has an increased half-life relative to a corresponding non-substituted (undeuterated) compound. In some embodiments, the half-life is increased by at least 5%, 10%, 25%, 50%, 75%, 100%, 150%, or 200%.

In some embodiments, the compound stimulates release of a monoamine neurotransmitter and/or inhibits the function of a monoamine transporter. In some embodiments, the monoamine neurotransmitter is any of serotonin (5-HT), dopamine (DA), and norepinephrine (NE), and/or the monoamine transporter is any of a serotonin transporter (SERT), a dopamine transporter (DAT), and a norepinephrine transporter (NET).

In some embodiments, the compound does not cause neurotoxicity, or results in a reduction of neurotoxic effects. In some embodiments, an absence or reduction of neurotoxic effect is determined by tests and procedures that are in silico, in vitro, or in vivo. In some embodiments, the neurotoxic effect is determined by measuring one or more of: a) at least one toxic metabolite of MDMA or at least one toxic metabolite of an MDMA analog; b) oxidative stress and dopamine-based quinones; c) mitochondrial dysfunction; and d) activation of glial cells. In some embodiments, the reduction of a neurotoxic effect is at 5%, 10%, 25%, 50%, 75%, 100%, 150%, or 200% relative to one or more comparators. In some embodiments, the one or more comparator is MDMA and/or MDMA-d3.

In some aspects, provided are pharmaceutical compositions comprising a therapeutically effective amount of a disclosed compound, and a pharmaceutically acceptable carrier, diluent, or excipient. In some embodiments, the compound is a pure or substantially pure individual enantiomer, or an enantiomerically enriched mixture having an optical purity of between 0-25%, between 25-50%, between 50-75%, between 75-90%, between 90-95%, or at least 95% enantiomeric excess.

In some aspects, provided are pharmaceutical compositions comprising a therapeutically effective amount of a disclosed compound and its non-substituted (undeuterated) compound, in a mixture by mole ratio or mass ratio of greater than 10:1, between 10:1 and 5:1, between 5:1 and 1:1, about 1:1, between 1:1 and 5:1, between 5:1 and 10:1, or greater than 10:1.

In some embodiments, the provided pharmaceutical compositions are suitable for oral, buccal, sublingual, injectable, subcutaneous, intravenous, or transdermal administration. In some embodiments, the pharmaceutical compositions are in unit dosage form. In some embodiments, a unit dosage form comprises the compound in a total amount of between 10 and 200 mg. In some embodiments, a unit dosage form comprises the compound in a total amount of between 25 and 150 mg. In some embodiments, the unit dosage form is an immediate release, controlled release, sustained release, extended release, or modified release formulation.

In some embodiments, the pharmaceutical composition further comprises a therapeutically effective amount of an additional active compound. In some embodiments, the additional active compound is selected from the group consisting of: amino acids, antioxidants, anti-inflammatory agents, analgesics, antineuropathic and antinociceptive agents, antimigraine agents, anxiolytics, antidepressants, antipsychotics, anti-PTSD agents, dissociatives, cannabinoids, immunostimulants, anti-cancer agents, antiemetics, orexigenics, antiulcer agents, antihistamines, antihypertensives, anticonvulsants, antiepileptics, bronchodilators, neuroprotectants, empathogens, psychedelics, monoamine oxidase inhibitors, tryptamines, terpenes, phenethylamines, sedatives, stimulants, nootropics, and vitamins.

In some embodiments, the additional active compound acts to increase a therapeutic effect, provide an additional therapeutic effect, decrease an unwanted effect, increase stability or shelf-life, improve bioavailability, induce synergy, or alter pharmacokinetics or pharmacodynamics. In some embodiments, the additional therapeutic effect is an antioxidant, anti-inflammatory, analgesic, antineuropathic, antinociceptive, antimigraine, anxiolytic, antidepressant, antipsychotic, anti-PTSD, dissociative, immunostimulant, anti-cancer, antiemetic, orexigenic, antiulcer, antihistamine, antihypertensive, anticonvulsant, antiepileptic, bronchodilator, neuroprotective, empathogenic, psychedelic, sedative, or stimulant effect.

In some aspects, a disclosed compound is provided for use in the treatment of a mental health disorder. In some aspects, provided are uses of a disclosed compound for the manufacture of a medicament for the treatment of a mental health disorder patient according to any of the methods described herein. In some aspects, provided are methods for modulating neurotransmission in a mammal, comprising administering to the mammal a therapeutically effective amount of a disclosed compound.

In some aspects, provided are methods for modulating neurotransmission in a mammal, comprising administering to the mammal a therapeutically effective amount of the pharmaceutical composition. In some embodiments, modulating neurotransmission comprises stimulating release of a monoamine neurotransmitter and/or inhibiting the function of a monoamine transporter. In some embodiments, the monoamine neurotransmitter is any of serotonin (5-HT), dopamine (DA), and norepinephrine (NE), and/or the monoamine transporter is any of a serotonin transporter (SERT), a dopamine transporter (DAT), and a norepinephrine transporter (NET).

In some aspects, provided are methods of treating a medical condition in a mammal in need of such treatment, the method comprising administering to the mammal a therapeutically effective amount of a disclosed compound. In some aspects, provided are methods for treating a medical condition in a mammal in need of such treatment, the method comprising administering to the mammal a therapeutically effective amount of a disclosed pharmaceutical composition, such as a pharmaceutical composition comprising a disclosed compound. In some embodiments, the medical condition is a disorder linked to dysregulation or inadequate functioning of neurotransmission. In some embodiments, the disorder linked to dysregulation or inadequate functioning of neurotransmission is that of monoaminergic neurotransmission. In some embodiments, the disorder linked to dysregulation or inadequate functioning of monoaminergic neurotransmission is that of serotonergic, dopaminergic, or noradrenergic neurotransmission.

In some embodiments, the medical condition is a mental health disorder. In some embodiments, the mental health disorder is selected from the group consisting of: post-traumatic stress disorder (PTSD), adjustment disorder, affective disorder, depression, atypical depression, postpartum depression, catatonic depression, a depressive disorder due to a medical condition, premenstrual dysphoric disorder, seasonal affective disorder, dysthymia, anxiety, phobia disorders, binge disorders, body dysmorphic disorder, alcohol or drug abuse or dependence disorders, a substance use disorder, substance-induced mood disorder, a mood disorder related to another health condition, disruptive behavior disorders, eating disorders, impulse control disorders, obsessive compulsive disorder (OCD), attention deficit hyperactivity disorder (ADHD), personality disorders, attachment disorders, and dissociative disorders.

In some embodiments, the mental health disorder is a disorder related to rigid modes of thinking. In some embodiments, the disorder related to rigid modes of thinking is anxiety, depression, addiction, an eating disorder, an alcohol or drug abuse or dependence disorder, OCD, or PTSD. In some embodiments, depression is Major Depressive Disorder or Treatment Resistant Depression. In some embodiments, anxiety is General Anxiety Disorder. In some embodiments, the substance use disorder is any of alcohol use disorder, nicotine dependency, opioid use disorder, sedative, hypnotic, or anxiolytic use disorder, stimulant use disorder, or tobacco use disorder. In some embodiments, the medical condition is a neurodegenerative disorder. In some embodiments, the neurodegenerative disorder is any of multiple sclerosis, Parkinson's disease, dementia, Alzheimer's disease, Huntington's disease, amyotrophic lateral sclerosis (ALS), and motor neuron disease.

In some embodiments, the method does not cause neurotoxicity, or results in a reduction of neurotoxic effects. In some embodiments, the neurotoxic effect is determined by measuring one or more of: a) at least one toxic metabolite of MDMA or at least one toxic metabolite of an MDMA analog; b) oxidative stress and dopamine-based quinones; c) mitochondrial dysfunction; and d) activation of glial cells. In some embodiments, the reduction of a neurotoxic effect is at least 5%, 10%, 25%, 50%, 75%, 100%, 150%, or 200% relative to one or more comparators. In some embodiments, the one or more comparators is MDMA, MDMA-d3, and/or a corresponding non-substituted (undeuterated) compound.

In some embodiments, the mammal has a genetic variation associated with drug metabolism, including a genetic variation relating to CYP2B6, CYP1A2, CYP2C19, CYP2D6, or CYP3A4 enzymes; or associated with a mental health disorder, trauma or stressor related disorder, depression, or anxiety, and including a genetic variation in mGluR5 or FKBP5; or relating to a membrane transporter, such as SERT, DAT, NET, or VMAT. In embodiments, the mammal has altered epigenetic regulation of a gene the expression of which is associated with a mental health condition or susceptibility to a mental health treatment, such as the SIGMAR1 gene for the non-opioid sigma-1 receptor. In some embodiments, the mammal is a human.

In some aspects provided are methods for improving mental health or functioning in a human, the method comprising identifying a human in need of said improving, and administering to the human a disclosed compound. In some aspects provided are methods for improving mental health or functioning in a human, the method comprising identifying a human in need of said improving, and administering to the human a disclosed pharmaceutical composition. In some embodiments, the improvement in mental health or functioning is a reduction of neuroticism or psychological defensiveness, an increase in creativity or openness to experience, an increase in decision-making ability, an increase in feelings of wellness or satisfaction, or an increase in ability to fall or stay asleep.

In some aspects provided are methods for reducing the symptoms of a mental health disorder in a human, the method comprising identifying a human in need of said reducing, and administering to the human a disclosed compound. In some aspects provided are methods for reducing the symptoms of a mental health disorder in a human, the method comprising identifying a human in need of said reducing, and administering to the human a disclosed pharmaceutical composition. In some embodiments, the compound or composition is administered together with one or more sessions of psychotherapy.

The foregoing has outlined broadly some pertinent features of certain exemplary embodiments of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be also realized that such equivalent structures do not depart from the spirit and scope of the invention as set forth in the appended claims. Hence, this summary has been made with the understanding that it is to be considered as a brief and general synopsis of only some of the objects and embodiments disclosed herein, is provided solely for the benefit and convenience of the reader, and is not intended to limit in any manner the scope, or range of equivalents, to which the claims are lawfully entitled.

DETAILED DESCRIPTION

Provided are deuterated empathogens, such as deuterated analogs and derivatives of MDMA and beta-keto (bk) MDMA (methylone) analogs. Also provided are methods of making the disclosed compounds, such as by chemical synthesis. Additionally provided are compositions, such as pharmaceutical compositions, comprising the disclosed compounds. Further provided are kits containing such compositions together with instructions for use. In other aspects, provided are methods of using the disclosed compounds and compositions thereof.

In some embodiments, the methods comprise modulating neurotransmission, such as in a subject. In some embodiments, disclosed compounds and compositions are used to treat a condition, such as a disease or a disorder. In some embodiments, any of the disclosed compounds or compositions may be used for treating a disease, preventing a disease, treating a condition, preventing a condition, and/or causing an effect. In embodiments, the methods of use are for treatment of a mental health disorder, or for the improvement of mental health and functioning.

Results have been published for certain deuterium-substituted MDMA having deuterium substitution of hydrogen at the methylenedioxy ring moiety (e.g., Berquist et al., Drug and Alcohol Dependence, 2020; 208, 107850; Fukuto et al., Journal of Medicinal Chemistry, 1991, 34(9), 2871-2876 [d2-MDMA]), and certain deuterated MDMA and methylone compounds are available as analytical reference materials for use as an internal standard for quantification (e.g., Cayman Chemical, Ann Arbor, Mich., d3-MDMA HCl [Item No. 15822] and d5-MDMA HCl [Item Nos. 18573 (RM), 20743 (CRM)]) and (CRM)]; d3-Methylone HCl [Item No. 18732]). Substituted amphetamine derivatives, including certain deuterated MDMA compounds, are also disclosed in U.S. Pub. No. 2008/0045588A1.

Applicant is unaware of the specific compounds and compositions disclosed herein having been synthesized, formulated, and/or used in the compositions and methods of the invention. Additionally, the results of replacing hydrogen with deuterium on any given structure can be variable and unpredictable. In some embodiments, Applicant's disclosed deuterated compounds are particularly advantageous. For example, by reducing the rate of N-dealkylation, the deuterated compounds disclosed herein may produce fewer species or lower concentrations of metabolites responsible for adverse effects, resulting in improved side-effect profiles, and may provide other advantages compared to corresponding non-substituted compounds.

While various aspects and features of certain embodiments are summarized above, the following detailed description illustrates several exemplary embodiments in further detail to enable one of skill in the art to practice such embodiments, and to make and use the full scope of the invention claimed. The described examples are provided for illustrative purposes and are not intended to limit the scope of the invention or its applications. It will be understood that many modifications, substitutions, changes, and variations in the described examples, embodiments, applications, and details of the invention illustrated herein can be made by those skilled in the art without departing from the spirit of the invention, or the scope of the invention as described in the appended claims, and the general principles defined herein may be applied to a wide range of aspects. Thus, the invention is not intended to be limited to the aspects presented, but is to be accorded the widest scope consistent with the principles and novel features disclosed. The description below is designed to make such embodiments apparent to a person of ordinary skill, in that the embodiments shall be both readily cognizable and readily creatable without undue experimentation, solely using the teachings herein together with general knowledge of the art.

A. Deuterated Compounds

In some aspects provided herein are deuterated empathogen compounds of Formula (I), Formula (II), Formula (III), and Formula (IV). Such compounds may be referred to herein as "disclosed compounds," "deuterated empathogens," or "therapeutic empathogens," and the terms may be used interchangeably. The term "deuterated" refers to a compound or substituent in which one or more protium (1H) atom(s) is/are replaced by one or more deuterium atom(s) and in which the abundance of deuterium (2H or D) at each position of the compound is higher than the natural abundance of deuterium isotope, which is approximately 0.0154%.

The term "empathogen" (meaning "generating a state of empathy") was independently suggested in 1983-84 by the psychologist and psychopharmacologist Ralph Metzner and the Purdue University professor of pharmacology and medicinal chemistry David Nichols. Nichols subsequently coined the term "entactogen" in 1986 (meaning "to touch within") (Holland et al., Ecstasy: The Complete Guide; A Comprehensive Look At The Risks And Benefits Of MDMA, 2001 at 182 n.2). Although both terms may be (and are) used interchangeably, compounds herein will be referred to as "empathogens."

In some embodiments, deuterated compounds are deuterium enriched. "Deuterium enriched" refers to a compound or composition where the abundance of deuterium at at least one position is higher than the natural abundance of deuterium, which is about 0.0154%, i.e., the amount of deuteration in a "naturally occurring" non-deuterated compound. In deuterium enriched compounds and compositions, the abundance of deuterium at each deuterated position may be higher than 10%, 20%, 30%, 40%, 50%, 60%, 70% or 80%, preferably higher than 90%, 95%, 96% or 97%, even more preferably higher than 98%, 99% or 99.5% at said position(s). It is understood that the abundance of deuterium at each deuterated position is independent of the abundance of deuterium at other deuterated position(s). In some embodiments, a compound of Formula (I), Formula (II), Formula (III), and Formula (IV), or a pharmaceutically acceptable salt, hydrate, solvate or prodrug thereof, is produced and tested in compliance with Good Laboratory Practice (GLP) or Good Manufacturing Practice (GMP) requirements.

In some embodiments, the invention provides deuterated analogs of 3,4-methylenedioxy methamphetamine (MDMA). In some embodiments, the invention provides deuterated beta-keto analogs of MDMA. In some embodiments, the invention provides deuterated analogs of methylone. In some embodiments, the deuterated analogs are fully deuterated. In some embodiments, the deuterated analogs are partially deuterated derivatives.

In some embodiments, disclosed is a compound of Formula (I):

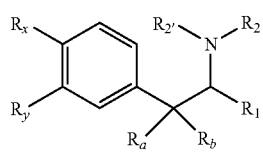

wherein: $R_1$ is hydrogen or $C_1$-$C_6$ alkyl; and $R_2$ and $R_{2'}$ are each independently a deuterated $C_1$-$C_6$ alkyl; or $R_2$ is H and $R_{2'}$ is a deuterated $C_1$-$C_6$ alkyl; or $R_2$ and $R_{2'}$ are taken together to form a deuterated 4- to 8-membered heterocyclyl; $R_a$ and $R_b$ are each independently hydrogen, —OH, or $C_1$-$C_6$ alkoxy; or $R_a$ and $R_b$ are taken together to form=O; and $R_x$ and $R_y$ are taken together as OCH=CH—, —CH=CHO—, —OCH$_2$O—, —SCH=CH—, —CH=CHS—, —SCH$_2$S—, —SCH$_2$O—, —OCH$_2$S—, —NHCH=CH—, —CH=CHNH—, —NHCH$_2$NH—, —NHCH$_2$O—, —OCH$_2$NH—, —NHCH$_2$S—, or —SCH$_2$NH—; or a pharmaceutically acceptable salt, prodrug, hydrate, or solvate thereof.

In some embodiments of a compound of Formula (I), $R_a$ and $R_b$ are both hydrogen, or $R_a$ and $R_b$ are taken together to form =O. In some embodiments of a compound of Formula (I), $R_a$ and $R_b$ are both hydrogen. In some embodiments of a compound of Formula (I), $R_a$ and $R_b$ are taken together to form =O. In some embodiments of a compound of Formula (I), $R_a$ and $R_b$ are each independently hydrogen or —OH. In some embodiments of a compound of Formula (I), one of $R_a$ and $R_b$ is hydrogen, and the other of $R_a$ and $R_b$ is —OH. In some embodiments of a compound of Formula (I), $R_a$ and $R_b$ are each independently hydrogen or $C_1$-$C_6$ alkoxy. In some embodiments of a compound of Formula (I), $R_a$ and $R_b$ are each independently hydrogen or methoxy. In some embodiments of a compound of Formula (I), one of $R_a$ and $R_b$ is hydrogen, and the other of $R_a$ and $R_b$ is methoxy. In all such embodiments are also included a pharmaceutically acceptable salt, prodrug, hydrate, or solvate of the compound.

In some embodiments, a compound of Formula (I) is not

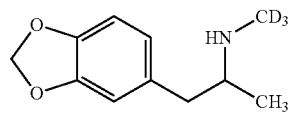 [SMILES: [2H]C([2H])([2H])NC(C)Cc1ccc2c(c1)OCO2]

(MDMA-d3).

In some embodiments, disclosed is a compound of Formula (II):

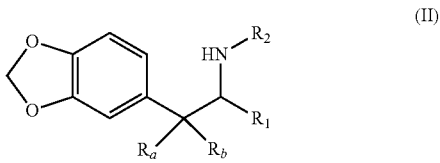

wherein: $R_1$ is hydrogen, —CH$_3$, or —CH$_2$CH$_3$; and $R_2$ is —CD$_3$, —CHD$_2$, —CH$_2$D, —CH$_2$CD$_3$, —CH$_2$CHD$_2$, —CH$_2$CH$_2$D, —CHDCD$_3$, —CHDCHD$_2$, —CHDCH$_2$D, —CD$_2$CD$_3$, —CD$_2$CHD$_2$, or —CD$_2$CH$_2$D; and $R_a$ and $R_b$ are each independently hydrogen, —OH, or $C_1$-$C_6$ alkoxy; or $R_a$ and $R_b$ are taken together to form =O; or a pharmaceutically acceptable salt, prodrug, hydrate, or solvate thereof.

In some embodiments of a compound of Formula (II), $R_a$ and $R_b$ are both hydrogen, or $R_a$ and $R_b$ are taken together to form =O. In some embodiments of a compound of Formula (II), $R_a$ and $R_b$ are both hydrogen. In some embodiments of a compound of Formula (II), $R_a$ and $R_b$ are taken together to form =O. In some embodiments of a compound of Formula (II), $R_a$ and $R_b$ are each independently hydrogen or —OH. In some embodiments of a compound of Formula (II), one of $R_a$ and $R_b$ is hydrogen, and the other of $R_a$ and $R_b$ is —OH. In some embodiments of a compound of Formula (II), $R_a$ and $R_b$ are each independently hydrogen or $C_1$-$C_6$ alkoxy. In some embodiments of a compound of Formula (II), $R_a$ and $R_b$ are each independently hydrogen or methoxy. In some embodiments of a compound of Formula (II), one of $R_a$ and $R_b$ is hydrogen, and the other of $R_a$ and $R_b$ is methoxy. In all such embodiments are also included a pharmaceutically acceptable salt, prodrug, hydrate, or solvate of the compound.

A deuterated analog of the invention may in particular be characterized by Formula (III) or a pharmaceutically acceptable salt thereof, wherein $R_1$ represents hydrogen, methyl, or ethyl, and $R_2$ represents an alkyl group with at least one deuterium.

"Alkyl" will be understood to include radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" can also be used. Preferably, an alkyl group comprises from 1 to 10 carbon atoms, more preferably, from 1 to 4 carbon atoms, and most preferably, from 1 to 4 carbon atoms.

In some preferred embodiments, $R_2$ is a methyl or ethyl group with at least one deuterium, and is therefore —$CD_3$, —$CHD_2$, —$CH_2D$, —$CH_2CD_3$, —$CH_2CHD_2$, —$CH_2CH_2D$, —$CHDCD_3$, —$CHDCHD_2$, —$CHDCH_2D$, —$CD_2CD_3$, —$CD_2CHD_2$, or —$CD_2CH_2D$.

With $R_1$ and $R_2$ as defined above, a compound of Formula (III) is as follows:

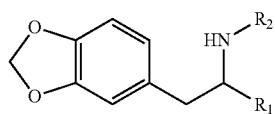

(III)

In one aspect, the compound of Formula (III) is a compound of Formula (IIIA):

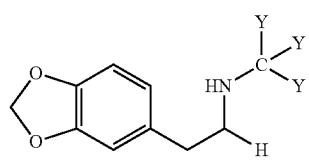

(IIIA)

or a pharmaceutically acceptable salt, prodrug, hydrate, or solvate thereof (which will be understood to include all amorphous and polymorphic forms); wherein each Y is independently protium (H) or deuterium (D), and wherein at least one or all Ys represents deuterium (D) and the remaining Ys represent protium (H).

In another aspect, the compound of Formula (III) is a compound of Formula (IIIB):

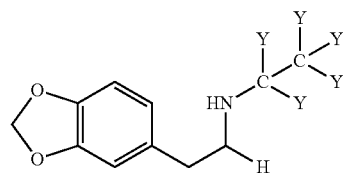

(IIIB)

or a pharmaceutically acceptable salt, prodrug, hydrate, or solvate thereof; wherein each Y is independently protium (H) or deuterium (D), and wherein at least one or all Ys represents deuterium (D) and the remaining Ys represent protium (H).

In a further aspect, the compound of Formula (III) is a compound of Formula (IIIC):

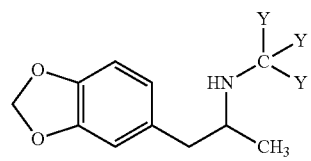

(IIIC)

or a pharmaceutically acceptable salt, prodrug, hydrate, or solvate thereof; wherein each Y is independently protium (H) or deuterium (D), and wherein at least one or all Ys represents deuterium (D) and the remaining Ys represent protium (H).

In another aspect, the compound of Formula (III) is a compound of Formula (IIID):

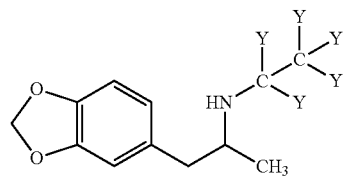

(IIID)

or a pharmaceutically acceptable salt, prodrug, hydrate, or solvate thereof; wherein each Y is independently protium (H) or deuterium (D), and wherein at least one or all Ys represents deuterium (D) and the remaining Ys represent protium (H).

In another aspect, the compound of Formula (III) is a compound of Formula (IIIE):

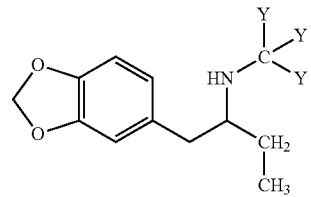

(IIIE)

or a pharmaceutically acceptable salt, prodrug, hydrate, or solvate thereof; wherein each Y is independently protium (H) or deuterium (D), and wherein at least one or all Ys represents deuterium (D) and the remaining Ys represent protium (H).

In a further aspect, the compound of Formula (III) is a compound of Formula (IIIF):

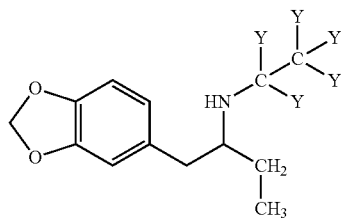

(IIIF)

or a pharmaceutically acceptable salt, prodrug, hydrate, or solvate thereof; wherein each Y is independently protium (H) or deuterium (D), and wherein at least one or all Ys represents deuterium (D) and the remaining Ys represent protium (H).

In the pharmaceutical compositions comprising a compound of Formula (IIIA), at least one instance of Y in the compound of Formula (IIIA) is deuterium. In certain aspects, at least two instances of Y of the compound of Formula (IIIA) are deuterium. In certain aspects, at least three instances of Y of the compound of Formula (IIIA) are deuterium.

In the pharmaceutical compositions comprising a compound of Formula (IIIB), at least one instance of Y in the compound of Formula (IIIB) is deuterium. In certain aspects, at least two instances of Y of the compound of Formula (IIIB) are deuterium. In certain aspects, at least three instances of Y of the compound of Formula (IIIB) are deuterium. In certain aspects, at least four instances of Y of the compound of Formula (IIIB) are deuterium. In certain aspects, at least five instances of Y of the compound of Formula (IIIB) are deuterium.

In the pharmaceutical compositions comprising a compound of Formula (IIIC), at least one instance of Y in the compound of Formula (IIIC) is deuterium. In certain aspects, at least two instances of Y of the compound of Formula (IIIC) are deuterium. In certain aspects, at least three instances of Y of the compound of Formula (IIIC) are deuterium.

In the pharmaceutical compositions comprising a compound of Formula (IIID), at least one instance of Y in the compound of Formula (IIID) is deuterium. In certain aspects, at least two instances of Y of the compound of Formula (IIID) are deuterium. In certain aspects, at least three instances of Y of the compound of Formula (IIID) are deuterium. In certain aspects, at least four instances of Y of the compound of Formula (IIID) are deuterium. In certain aspects, at least five instances of Y of the compound of Formula (IIID) are deuterium.

In the pharmaceutical compositions comprising a compound of Formula (IIIE), at least one instance of Y in the compound of Formula (IIIE) is deuterium. In certain aspects, at least two instances of Y of the compound of Formula (IIIE) are deuterium. In certain aspects, at least three instances of Y of the compound of Formula (IIIE) are deuterium.

In the pharmaceutical compositions comprising a compound of Formula (IIIF), at least one instance of Y in the compound of Formula (IIIF) is deuterium. In certain aspects, at least two instances of Y of the compound of Formula (IIIF) are deuterium. In certain aspects, at least three instances of Y of the compound of Formula (IIIF) are deuterium. In certain aspects, at least four instances of Y of the compound of Formula (IIIF) are deuterium. In certain aspects, at least five instances of Y of the compound of Formula (IIIF) are deuterium.

Non-limiting exemplary compounds of Formula (III) are below:

| Exemplary embodiments of IIIA |
|---|
| 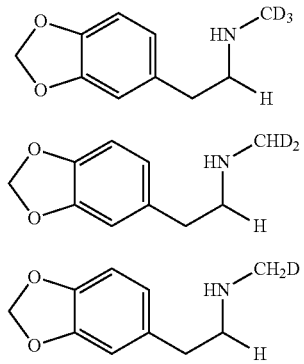 |

| Exemplary embodiments of IIIB |
|---|
| 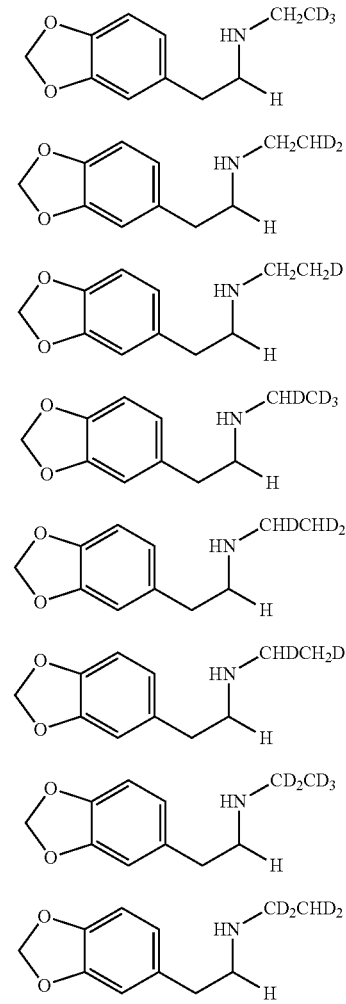 |

Exemplary embodiments of IIIB
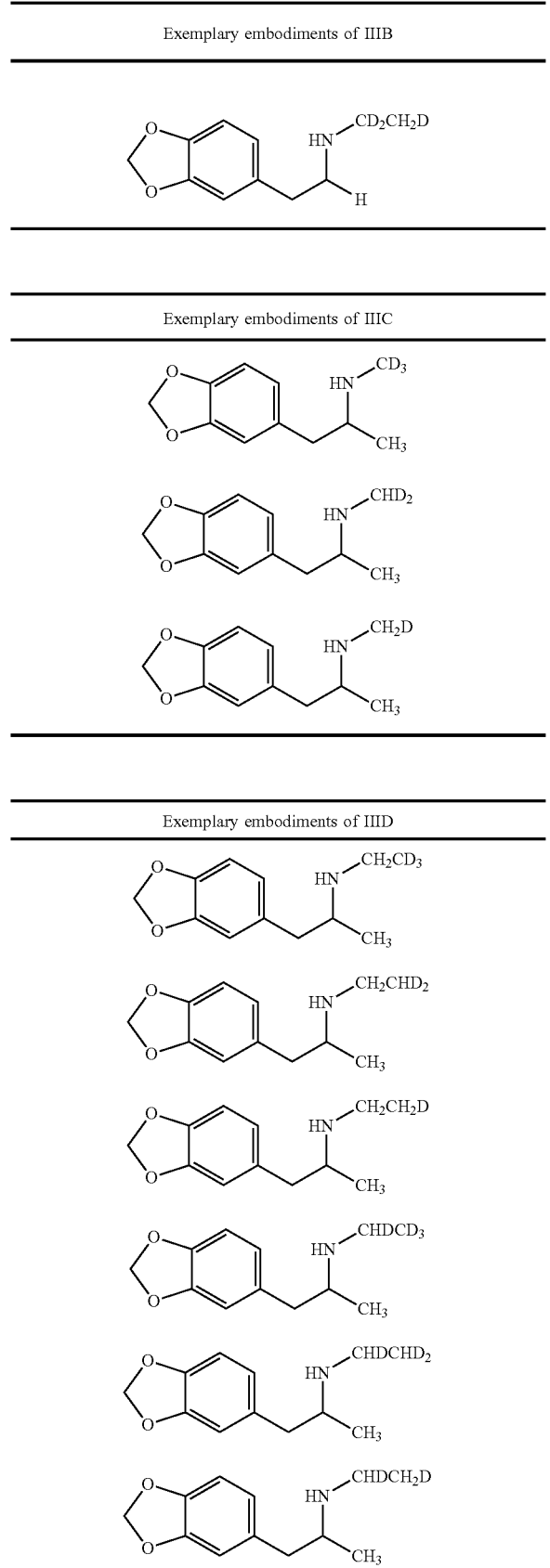
Exemplary embodiments of IIIC
Exemplary embodiments of IIID
Exemplary embodiments of IIID
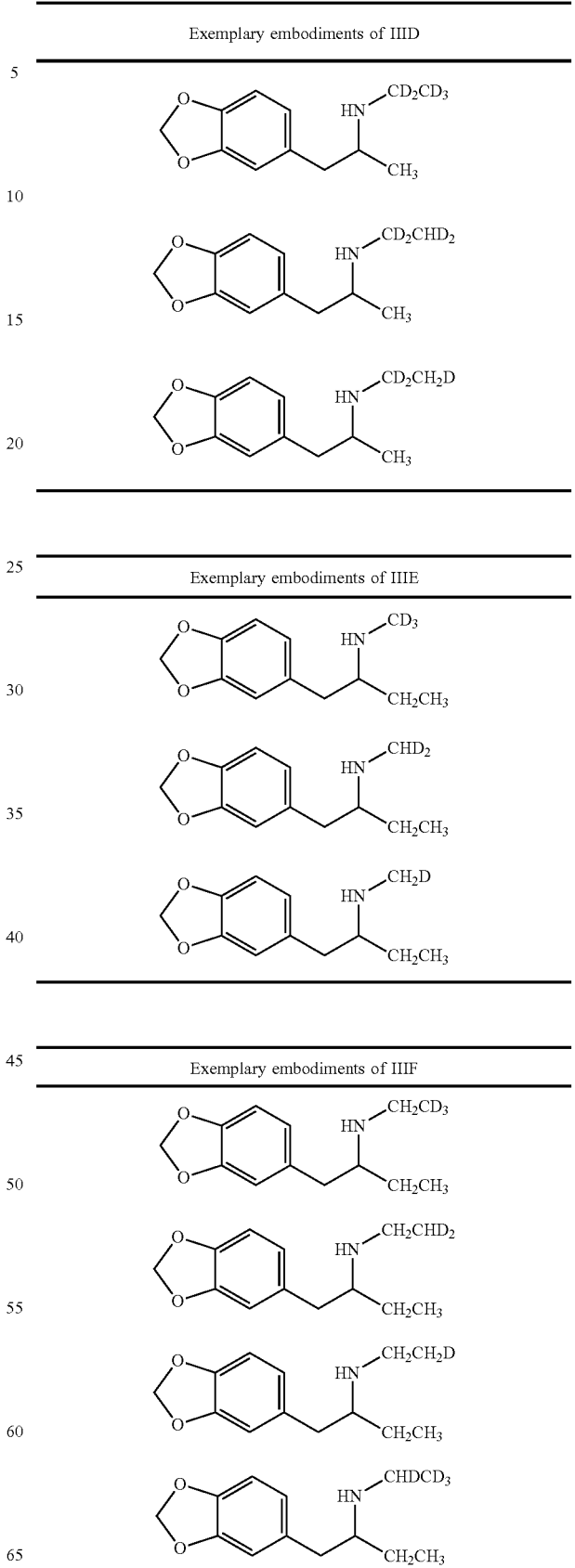
Exemplary embodiments of IIIE
Exemplary embodiments of IIIF

| Exemplary embodiments of IIIF |
|---|
| 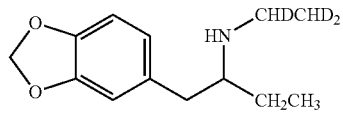 |
| 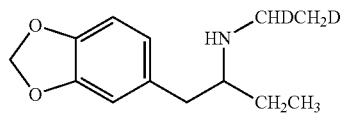 |
| 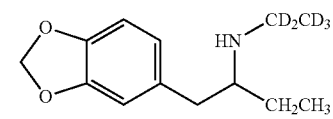 |
| 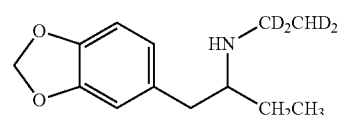 |
| 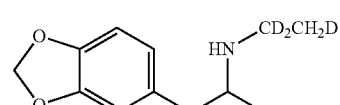 |

In some embodiments, the invention relates to deuterated compounds of Formula (IV). In some embodiments, deuterated compounds of Formula (IV) and compositions thereof are deuterium enriched. In some embodiments, deuterium enriched compounds of Formula (IV) and compositions thereof comprise an abundance of deuterium at each deuterated position that may be higher than 10%, 20%, 30%, 40%, 50%, 60%, 70% or 80%, preferably higher than 90%, 95%, 96% or 97%, even more preferably higher than 98%, 99% or 99.5% at said position(s). It is understood that the abundance of deuterium at each deuterated position is independent of the abundance of deuterium at other deuterated position(s).

In some embodiments, the invention provides deuterated analogs of methylone. The deuterated analogs of the invention may be fully or partially deuterium substituted derivatives.

A deuterated analog of the invention may in particular be characterized by Formula (IV) or pharmaceutically acceptable salt thereof, wherein $R_1$ represents hydrogen, methyl, or ethyl, and $R_2$ represents an alkyl group with at least one deuterium.

In some preferred embodiments, $R_2$ is a methyl or ethyl group with at least one deuterium, and is therefore —$CD_3$, —$CHD_2$, —$CH_2D$, —$CH_2CD_3$, —$CH_2CHD_2$, —$CH_2CH_2D$, —$CHDCD_3$, —$CHDCHD_2$, —$CHDCH_2D$, —$CD_2CD_3$, —$CD_2CHD_2$, or —$CD_2CH_2D$.

With $R_1$ and $R_2$ as defined above, a compound of Formula (IV) is as follows:

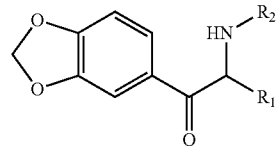

(IV)

In one aspect, the compound of Formula (IV) is a compound of Formula (IVA):

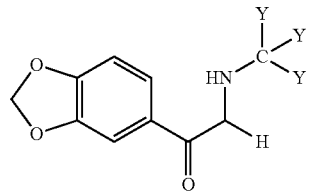

(IVA)

or a pharmaceutically acceptable salt, prodrug, hydrate, or solvate thereof; wherein each Y is independently protium (H) or deuterium (D), and wherein at least one or all Ys represents deuterium (D) and the remaining Ys represent protium (H).

In another aspect, the compound of Formula (IV) is a compound of Formula (IVB):

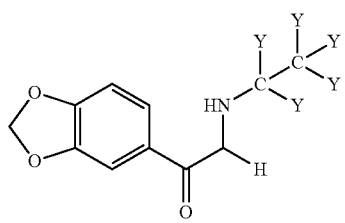

(IVB)

or a pharmaceutically acceptable salt, prodrug, hydrate, or solvate thereof; wherein each Y is independently protium (H) or deuterium (D), and wherein at least one or all Ys represents deuterium (D) and the remaining Ys represent protium (H).

In another aspect, the compound of Formula (IV) is a compound of Formula (IVC):

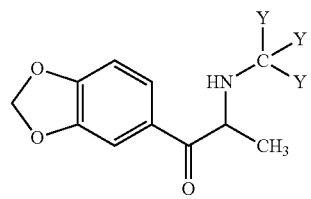

(IVC)

or a pharmaceutically acceptable salt, prodrug, hydrate, or solvate thereof; wherein each Y is independently protium (H) or deuterium (D), and wherein at least one or all Ys represents deuterium (D) and the remaining Ys represent protium (H).

In another aspect, the compound of Formula (IV) is a compound of Formula (IVD):

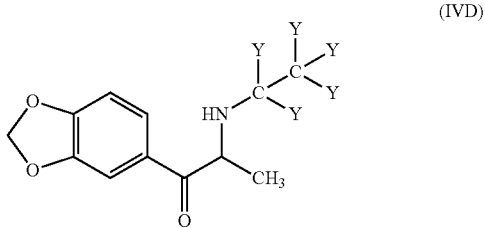

(IVD)

or a pharmaceutically acceptable salt, prodrug, hydrate, or solvate thereof; wherein each Y is independently protium (H) or deuterium (D), and wherein at least one or all Ys represents deuterium (D) and the remaining Ys represent protium (H).

In another aspect, the compound of Formula (IV) is a compound of Formula (IVE):

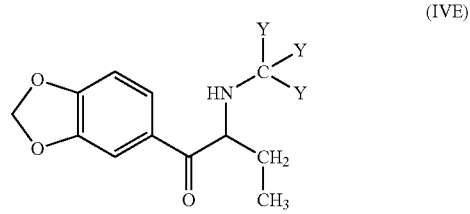

(IVE)

or a pharmaceutically acceptable salt, prodrug, hydrate, or solvate thereof; wherein each Y is independently protium (H) or deuterium (D), and wherein at least one or all Ys represents deuterium (D) and the remaining Ys represent protium (H).

In a further aspect, the compound of Formula (IV) is a compound of Formula (IVF):

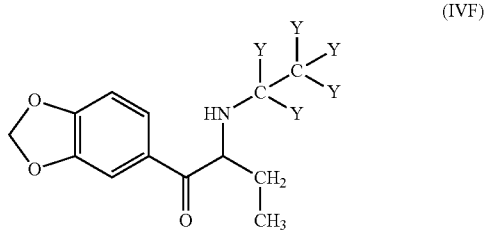

(IVF)

or a pharmaceutically acceptable salt, prodrug, hydrate, or solvate thereof; wherein each Y is independently protium (H) or deuterium (D), and wherein at least one or all Ys represents deuterium (D) and the remaining Ys represent protium (H).

In the pharmaceutical compositions comprising a compound of Formula (IVA), at least one instance of Y in the compound of Formula (IVA) is deuterium. In certain aspects, at least two instances of Y of the compound of Formula (IVA) are deuterium. In certain aspects, at least three instances of Y of the compound of Formula (IVA) are deuterium.

In the pharmaceutical compositions comprising a compound of Formula (IVB), at least one instance of Y in the compound of Formula (IVB) is deuterium. In certain aspects, at least two instances of Y of the compound of Formula (IVB) are deuterium. In certain aspects, at least three instances of Y of the compound of Formula (IVB) are deuterium. In certain aspects, at least four instances of Y of the compound of Formula (IVB) are deuterium. In certain aspects, at least five instances of Y of the compound of Formula (IVB) are deuterium.

In the pharmaceutical compositions comprising a compound of Formula (IVC), at least one instance of Y in the compound of Formula (IVC) is deuterium. In certain aspects, at least two instances of Y of the compound of Formula (IVC) are deuterium. In certain aspects, at least three instances of Y of the compound of Formula (IVC) are deuterium.

In the pharmaceutical compositions comprising a compound of Formula (IVD), at least one instance of Y in the compound of Formula (IVD) is deuterium. In certain aspects, at least two instances of Y of the compound of Formula (IVD) are deuterium. In certain aspects, at least three instances of Y of the compound of Formula (IVD) are deuterium. In certain aspects, at least four instances of Y of the compound of Formula (IVD) are deuterium. In certain aspects, at least five instances of Y of the compound of Formula (IVD) are deuterium.

In the pharmaceutical compositions comprising a compound of Formula (IVE), at least one instance of Y in the compound of Formula (IVE) is deuterium. In certain aspects, at least two instances of Y of the compound of Formula (IVE) are deuterium. In certain aspects, at least three instances of Y of the compound of Formula (IVE) are deuterium.

In the pharmaceutical compositions comprising a compound of Formula (IVF), at least one instance of Y in the compound of Formula (IVF) is deuterium. In certain aspects, at least two instances of Y of the compound of Formula (IVF) are deuterium. In certain aspects, at least three instances of Y of the compound of Formula (IVF) are deuterium. In certain aspects, at least four instances of Y of the compound of Formula (IVF) are deuterium. In certain aspects, at least five instances of Y of the compound of Formula (IVF) are deuterium.

Non-limiting exemplary compounds of Formula (IV) are below:

Exemplary embodiments of IVA

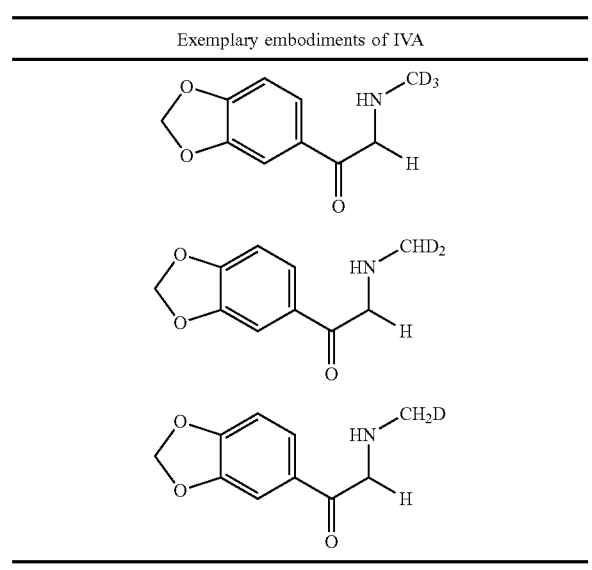

| Exemplary embodiments of IVB | Exemplary embodiments of IVC |
|---|---|
| 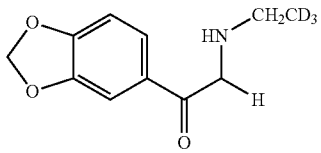 | 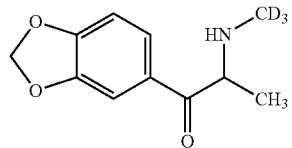 |
| 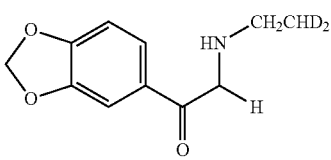 | 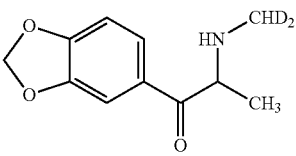 |
| 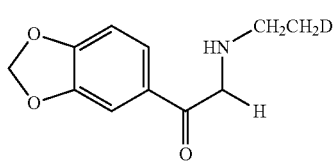 | 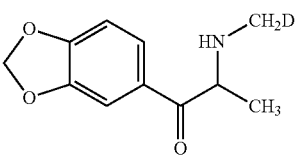 |
| Exemplary embodiments of IVD |
|---|
| 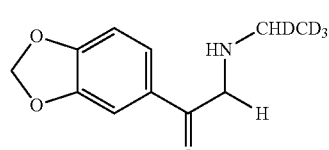 |
| 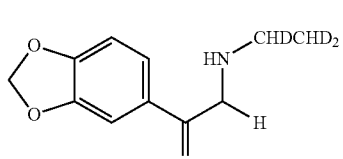 |
| 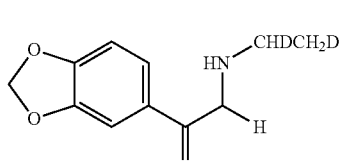 |
| 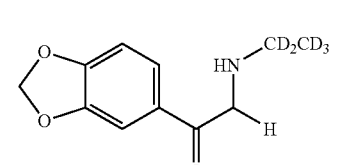 |
| 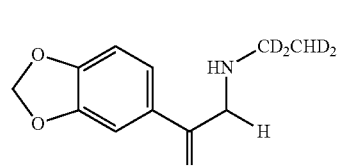 |
| 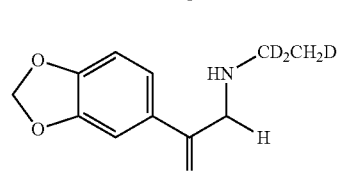 |
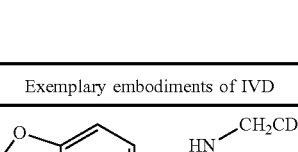
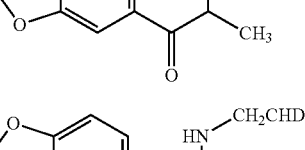
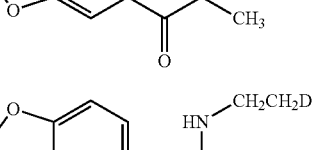
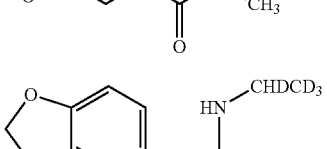
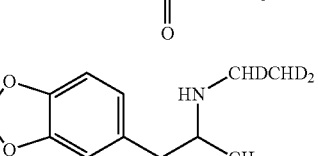
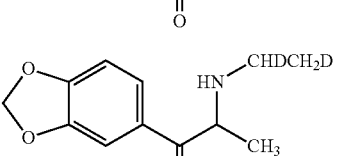

| Exemplary embodiments of IVD |
|---|
| 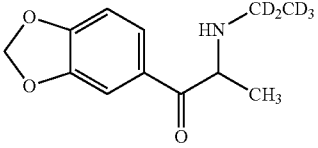 |
|  |
| 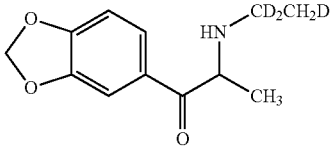 |

| Exemplary embodiments of IVE |
|---|
| 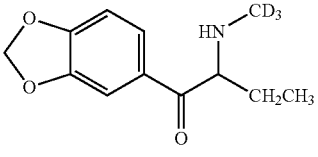 [SMILES: [2H]C([2H])([2H])NC(CC)C(=O)c1ccc2c(c1)OCO2] |
| 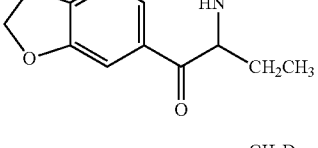 |
| 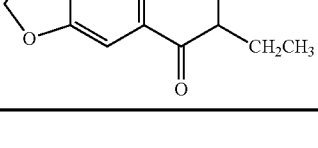 |

| Exemplary embodiments of IVF |
|---|
| 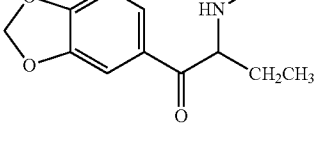 |
| 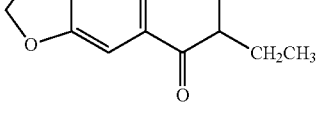 |
|  |
| 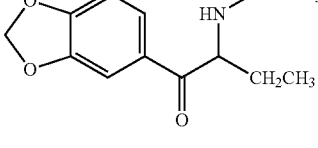 |
| 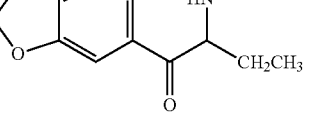 |
| 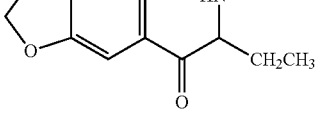 |
| 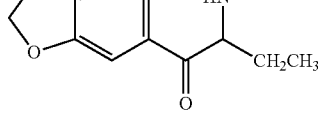 |
| 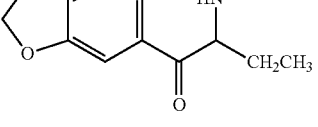 |
| 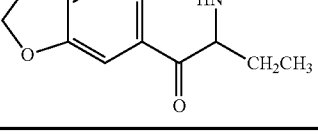 |

3,4-methylenedioxymethcathinone also known as methylone and bk-MDMA, is a beta-keto analog of MDMA. Pharmacologically, methylone and MDMA share certain similarities. However, while repeated high doses of MDMA have been shown to markedly reduce serotonin concentrations in the cortex and striatum, in some embodiments herein, such an effect will not be observed with methylone (Baumann et al., Neuropsychopharmacology 37(5):1192-1203). Substantially high doses (1.0-1.5 g) nevertheless can cause vomiting, sweating, paresthesia, palpitations, agitation, tremors, muscle twitching, and vertigo (Poyatos et al., Biology (Basel). 2021; 10(8):788).

Two major metabolic pathways of methylone have been shown for both humans and rats: (1) side-chain degradation by N-demethylation to the corresponding primary amine methylenedioxycathinone (MDC), partly conjugated; and (2) demethylenation followed by O-methylation of either a 3- or 4-OH group on the benzene ring to produce 4-hydroxy- 3-methoxymethcathinone (HMMC) or 3-hydroxy-4-methoxymethcathinone (3-OH-4-MeO-MC), respectively, mostly conjugated (Kamata et al., Xenobiotica, 2006; 36(8): 709-723). Methylone is metabolized in the liver, predominantly by the enzymatic activity of CYP2D6, CYP2B6, CYP1A2, and CYP2C19. Hepatic metabolism of methylone by CYP2B6, CYP1A2, and CYP2C19 results in formation of the N-demethylated primary metabolite 3,4-methylenedioxycathinone (MDC).

Evidence has shown that the adverse events associated with ingestion of its non-beta substituted analog MDMA, such as described above, as well as serotonin depletion, serotonergic nerve terminal degeneration, and neuronal apoptosis, may be caused by the N-demethylated metabolite of MDMA, 3,4-methylenedioxyamphetamine (MDA). Accordingly, while methylone may have less side effects than MDMA generally, in some disclosed embodiments herein, protecting methylone from N-dealkylation (and reducing the rate of its metabolism to MDC) may likewise result in fewer adverse events.

a. Isotopic Purity

In some embodiments, a compound of Formula (I), Formula (II), Formula (III), and Formula (IV), or a pharmaceutically acceptable salt, hydrate, solvate or prodrug thereof, has a deuterium isotopic purity of at least 50%, 55%, 60%, 65%, 70%, 75%, 80%, 85%, 90%, 91%, 92%, 93%, 94%, 95%, 96%, 97%, 98%, 99%, 99.5%, 99.6%, 99.7%, 99.8%, 99.9%, or 100%. In one embodiment, the compound of any of Formula (I), Formula (II), Formula (III), and Formula (IV), or a pharmaceutically acceptable salt, hydrate, solvate or prodrug thereof, has an isotopic purity of at least 50%. In an embodiment, the compound of any of Formula (I), Formula (II), Formula (III), and Formula (IV), or a pharmaceutically acceptable salt, hydrate, solvate or prodrug thereof, has an isotopic purity of at least 55%. In another embodiment, the compound of any of Formula (I), Formula (II), Formula (III), and Formula (IV), or a pharmaceutically acceptable salt, hydrate, solvate or prodrug thereof, has an isotopic purity of at least 60%. In yet another embodiment, the compound of any of Formula (I), Formula (II), Formula (III), and Formula (IV), or a pharmaceutically acceptable salt, hydrate, solvate or prodrug thereof, has an isotopic purity of at least 65%. In another embodiment, the compound of any of Formula (I), Formula (II), Formula (III), and Formula (IV), or a pharmaceutically acceptable salt, hydrate, solvate or prodrug thereof, has an isotopic purity of at least 70%. In another embodiment, the compound of any of Formula (I), Formula (II), Formula (III), and Formula (IV), or a pharmaceutically acceptable salt, hydrate, solvate or prodrug thereof, has an isotopic purity of at least 75%. In another embodiment, the compound of any of Formula (I), Formula (II), Formula (III), and Formula (IV), or a pharmaceutically acceptable salt, hydrate, solvate or prodrug thereof, has an isotopic purity of at least 80%. In another embodiment, the compound of any of Formula (I), Formula (II), Formula (III), and Formula (IV), or a pharmaceutically acceptable salt, hydrate, solvate or prodrug thereof, has an isotopic purity of at least 85%. In another embodiment, the compound of any of Formula (I), Formula (II), Formula (III), and Formula (IV), or a pharmaceutically acceptable salt, hydrate, solvate or prodrug thereof, has an isotopic purity of at least 90%. In another embodiment, the compound of any of Formula (I), Formula (II), Formula (III), and Formula (IV), or a pharmaceutically acceptable salt, hydrate, solvate or prodrug thereof, has an isotopic purity of at least 91%. In another embodiment, the compound of any of Formula (I), Formula (II), Formula (III), and Formula (IV), or a pharmaceutically acceptable salt, hydrate, solvate or prodrug thereof, has an isotopic purity of at least 92%. In another embodiment, the compound of any of Formula (I), Formula (II), Formula (III), and Formula (IV), or a pharmaceutically acceptable salt, hydrate, solvate or prodrug thereof, has an isotopic purity of at least 93%. In another embodiment, the compound of any of Formula (I), Formula (II), Formula (III), and Formula (IV), or a pharmaceutically acceptable salt, hydrate, solvate or prodrug thereof, has an isotopic purity of at least 94%. In another embodiment, the compound of any of Formula (I), Formula (II), Formula (III), and Formula (IV), or a pharmaceutically acceptable salt, hydrate, solvate or prodrug thereof, has an isotopic purity of at least 95%. In another embodiment, the compound of any of Formula (I), Formula (II), Formula (III), and Formula (IV), or a pharmaceutically acceptable salt, hydrate, solvate or prodrug thereof, has an isotopic purity of at least 96%. In another embodiment, the compound of any of Formula (I), Formula (II), Formula (III), and Formula (IV), or a pharmaceutically acceptable salt, hydrate, solvate or prodrug thereof, has an isotopic purity of at least 97%. In another embodiment, the compound of any of Formula (I), Formula (II), Formula (III), and Formula (IV), or a pharmaceutically acceptable salt, hydrate, solvate or prodrug thereof, has an isotopic purity of at least 98%. In another embodiment, the compound of any of Formula (I), Formula (II), Formula (III), and Formula (IV), or a pharmaceutically acceptable salt, hydrate, solvate or prodrug thereof, has an isotopic purity of at least 99%. In another embodiment, the compound of any of Formula (I), Formula (II), Formula (III), and Formula (IV), or a pharmaceutically acceptable salt, hydrate, solvate or prodrug thereof, has an isotopic purity of at least 99.5%. In another embodiment, the compound of any of Formula (I), Formula (II), Formula (III), and Formula (IV), or a pharmaceutically acceptable salt, hydrate, solvate or prodrug thereof, has an isotopic purity of at least 99.6%. In another embodiment, the compound of any of Formula (I), Formula (II), Formula (III), and Formula (IV), or a pharmaceutically acceptable salt, hydrate, solvate or prodrug thereof, has an isotopic purity of at least 99.7%. In another embodiment, the compound of any of Formula (I), Formula (II), Formula (III), and Formula (IV), or a pharmaceutically acceptable salt, hydrate, solvate or prodrug thereof, has an isotopic purity of at least 99.8%. In another embodiment, the compound of any of Formula (I), Formula (II), Formula (III), and Formula (IV), or a pharmaceutically acceptable salt, hydrate, solvate or prodrug thereof, has an isotopic purity of at least 99.9%. For such isotopically-labeled molecules, isotopic enrichment may be described as a percentage indicating the percent of isotopic atoms at a particular site on the molecule. The percentage can be referred to as the "isotopic purity" of the isotopically-labeled compound.

In some embodiments, a compound of any of Formula (I), Formula (II), Formula (III), and Formula (IV), or a pharmaceutically acceptable salt, hydrate, solvate or prodrug thereof, will be a mixture of the compound of any of Formula (I), Formula (II), Formula (III), and Formula (IV) of the invention (i.e., a deuterium-substituted compound, of any isotopic purity) and a corresponding non-substituted compound (i.e., the corresponding compound wherein none of the hydrogens are substituted by a deuterium, e.g., at no position of the compound will the presence of deuterium be higher than the natural abundance of deuterium isotope), or a pharmaceutically acceptable salt, hydrate, solvate or prodrug thereof. In such mixtures, at least 1%, 2%, 3%, 4%, 5%, 10%, 20%, 30%, 40%, 50%, 55%, 60%, 65%, 70%, 75%, 80%, 85%, 90%, 91%, 92%, 93%, 94%, 95%, 96%, 97%, 98%, 99%, 99.5%, 99.6%, 99.7%, 99.8%, 99.9%, or 100% are deuterium-substituted compounds of any of Formula (I), Formula (II), Formula (III), and Formula (IV), or a pharmaceutically acceptable salt, hydrate, solvate or prodrug thereof (wherein the other compounds in such mixtures are the corresponding non-substituted compounds). In an embodiment, at least 1% of the compounds of any of Formula (I), Formula (II), Formula (III), and Formula (IV), or a pharmaceutically acceptable salt, hydrate, solvate or prodrug thereof, are deuterium-substituted. In an embodiment, at least 2% of the compounds of any of Formula (I), Formula (II), Formula (III), and Formula (IV), or a pharmaceutically acceptable salt, hydrate, solvate or prodrug thereof, are deuterium-substituted. In an embodiment, at least 3% of the compounds of any of Formula (I), Formula (II), Formula (III), and Formula (IV), or a pharmaceutically acceptable salt, hydrate, solvate or prodrug thereof, are deuterium-substituted. In an embodiment, at least 4% of the compounds of any of Formula (I), Formula (II), Formula (III), and Formula (IV), or a pharmaceutically acceptable salt, hydrate, solvate or prodrug thereof, are deuterium-substituted. In an embodiment, at least 5% of the compounds of any of Formula (I), Formula (II), Formula (III), and Formula (IV), or a pharmaceutically acceptable salt, hydrate, solvate or prodrug thereof, are deuterium-substituted. In an embodiment, at least 10% of the compounds of any of Formula (I), Formula (II), Formula (III), and Formula (IV), or a pharmaceutically acceptable salt, hydrate, solvate or prodrug thereof, are deuterium-substituted. In an embodiment, at least 20% of the compounds of any of Formula (I), Formula (II), Formula (III), and Formula (IV), or a pharmaceutically acceptable salt, hydrate, solvate or prodrug thereof, are deuterium-substituted. In an embodiment, at least 30% of the compounds of any of Formula (I), Formula (II), Formula (III), and Formula (IV), or a pharmaceutically acceptable salt, hydrate, solvate or prodrug thereof, are deuterium-substituted. In an embodiment, at least 40% of the compounds of any of Formula (I), Formula (II), Formula (III), and Formula (IV), or a pharmaceutically acceptable salt, hydrate, solvate or prodrug thereof, are deuterium-substituted. In an embodiment, at least 50% of the compounds of any of Formula (I), Formula (II), Formula (III), and Formula (IV), or a pharmaceutically acceptable salt, hydrate, solvate or prodrug thereof, are deuterium-substituted. In an embodiment, the compound of any of Formula (I), Formula (II), Formula (III), and Formula (IV), or a pharmaceutically acceptable salt, hydrate, solvate or prodrug thereof, at least 55% are deuterium-substituted. In another embodiment, the compound of any of Formula (I), Formula (II), Formula (III), and Formula (IV), or a pharmaceutically acceptable salt, hydrate, solvate or prodrug thereof, at least 60% are deuterium-substituted. In yet another embodiment, the compound of any of Formula (I), Formula (II), Formula (III), and Formula (IV), or a pharmaceutically acceptable salt, hydrate, solvate or prodrug thereof, at least 65% are deuterium-substituted. In another embodiment, the compound of any of Formula (I), Formula (II), Formula (III), and Formula (IV), or a pharmaceutically acceptable salt, hydrate, solvate or prodrug thereof, at least 70% are deuterium-substituted. In another embodiment, the compound of any of Formula (I), Formula (II), Formula (III), and Formula (IV), or a pharmaceutically acceptable salt, hydrate, solvate or prodrug thereof, at least 75% are deuterium-substituted. In another embodiment, the compound of any of Formula (I), Formula (II), Formula (III), and Formula (IV), or a pharmaceutically acceptable salt, hydrate, solvate or prodrug thereof, at least 80% are deuterium-substituted. In another embodiment, the compound of any of Formula (I), Formula (II), Formula (III), and Formula (IV), or a pharmaceutically acceptable salt, hydrate, solvate or prodrug thereof, at least 85% are deuterium-substituted. In another embodiment, the compound of any of Formula (I), Formula (II), Formula (III), and Formula (IV), or a pharmaceutically acceptable salt, hydrate, solvate or prodrug thereof, at least 90% are deuterium-substituted. In another embodiment, the compound of any of Formula (I), Formula (II), Formula (III), and Formula (IV), or a pharmaceutically acceptable salt, hydrate, solvate or prodrug thereof, at least 91% are deuterium-substituted. In another embodiment, the compound of any of Formula (I), Formula (II), Formula (III), and Formula (IV), or a pharmaceutically acceptable salt, hydrate, solvate or prodrug thereof, at least 92% are deuterium-substituted. In another embodiment, the compound of any of Formula (I), Formula (II), Formula (III), and Formula (IV), or a pharmaceutically acceptable salt, hydrate, solvate or prodrug thereof, at least 93% are deuterium-substituted. In another embodiment, the compound of any of Formula (I), Formula (II), Formula (III), and Formula (IV), or a pharmaceutically acceptable salt, hydrate, solvate or prodrug thereof, at least 94% are deuterium-substituted. In another embodiment, the compound of any of Formula (I), Formula (II), Formula (III), and Formula (IV), or a pharmaceutically acceptable salt, hydrate, solvate or prodrug thereof, at least 95% are deuterium-substituted. In another embodiment, the compound of any of Formula (I), Formula (II), Formula (III), and Formula (IV), or a pharmaceutically acceptable salt, hydrate, solvate or prodrug thereof, at least 96% are deuterium-substituted. In another embodiment, the compound of any of Formula (I), Formula (II), Formula (III), and Formula (IV), or a pharmaceutically acceptable salt, hydrate, solvate or prodrug thereof, at least 97% are deuterium-substituted. In another embodiment, the compound of any of Formula (I), Formula (II), Formula (III), and Formula (IV), or a pharmaceutically acceptable salt, hydrate, solvate or prodrug thereof, at least 98% are deuterium-substituted. In another embodiment, the compound of any of Formula (I), Formula (II), Formula (III), and Formula (IV), or a pharmaceutically acceptable salt, hydrate, solvate or prodrug thereof, at least 99% are deuterium-substituted. In another embodiment, the compound of any of Formula (I), Formula (II), Formula (III), and Formula (IV), or a pharmaceutically acceptable salt, hydrate, solvate or prodrug thereof, at least 99.5% are deuterium-substituted. In another embodiment, the compound of any of Formula (I), Formula (II), Formula (III), and Formula (IV), or a pharmaceutically acceptable salt, hydrate, solvate or prodrug thereof, at least 99.6% are deuterium-substituted. In another embodiment, the compound of any of Formula (I), Formula (II), Formula (III), and Formula (IV), or a pharmaceutically acceptable salt, hydrate, solvate or prodrug thereof, at least 99.7% are deuterium-substituted. In another embodiment, the compound of any of Formula (I), Formula (II), Formula (III), and Formula (IV), or a pharmaceutically acceptable salt, hydrate, solvate or prodrug thereof, at least 99.8% are deuterium-substituted. In another embodiment, the compound of any of Formula (I), Formula (II), Formula (III), and Formula (IV), or a pharmaceutically acceptable salt, hydrate, solvate or prodrug thereof, at least 99.9% are deuterium-substituted. In any of the embodiments described above, a non-substituted compound may be described as a compound of any of Formula (I), Formula (II), Formula (III), and Formula (IV), or a pharmaceutically acceptable salt, hydrate, solvate or prodrug thereof, wherein all of the deuterium atoms are replaced with hydrogen atoms.

The individual compounds of the compositions of the invention will be understood to also encompass pharmaceutically acceptable salts of such compounds. The term "pharmaceutically acceptable salt" refers to salts prepared from pharmaceutically acceptable non-toxic acids or bases, and which may be synthesized by conventional chemical methods. Generally, such salts are prepared by reacting the free acid or base forms of these agents with a stoichiometric amount of the appropriate base or acid in water or in an organic solvent, or in a mixture of the two; generally, nonaqueous media (e.g., ether, ethyl acetate, ethanol, isopropanol, or acetonitrile) are preferred. For therapeutic use, salts of the compounds are those wherein the counter-ion is pharmaceutically acceptable.

Exemplary salts include 2-hydroxyethanesulfonate, 2-naphthalenesulfonate, 2-napsylate, 3-hydroxy-2-naphthoate, 3-phenylpropionate, 4-acetamidobenzoate, acefyllinate, acetate, aceturate, adipate, alginate, aminosalicylate, ammonium, amsonate, ascorbate, aspartate, benzenesulfonate, benzoate, besylate, bicarbonate, bisulfate, bitartrate, borate, butyrate, calcium edetate, calcium, camphocarbonate, camphorate, camphorsulfonate, camsylate, carbonate, cholate, citrate, clavulariate, cyclopentanepropionate, cypionate, d-aspartate, d-camsylate, d-lactate, decanoate, dichloroacetate, digluconate, dodecylsulfate, edentate, edetate, edisylate, estolate, esylate, ethanesulfonate, ethyl sulfate, fumarate, furate, fusidate, galactarate (mucate), galacturonate, gallate, gentisate, gluceptate, glucoheptanoate, gluconate, glucuronate, glutamate, glutarate, glycerophosphate, glycolate, glycollylarsanilate, hemisulfate, heptanoate (enanthate), heptanoate, hexafluorophosphate, hexanoate, hexylresorcinate, hippurate, hybenzate, hydrabamine, hydrobromide, hydrobromide/bromide, hydrochloride, hydroiodide, hydroxide, hydroxybenzoate, hydroxynaphthoate, iodide, isethionate, isothionate, 1-aspartate, 1-camsylate, 1-lactate, lactate, lactobionate, laurate, laurylsulphonate, lithium, magnesium, malate, maleate, malonate, mandelate, meso-tartrate, mesylate, methanesulfonate, methylbromide, methylnitrate, methylsulfate, mucate, myristate, N-methylglucamine ammonium salt, napadisilate, naphthylate, napsylate, nicotinate, nitrate, octanoate, oleate, orotate, oxalate, p-toluenesulfonate, palmitate, pamoate, pantothenate, pectinate, persulfate, phenylpropionate, phosphate, phosphateldiphosphate, picrate, pivalate, polygalacturonate, potassium, propionate, pyrophosphate, saccharate, salicylate, salicylsulfate, sodium, stearate, subacetate, succinate, sulfate, sulfosaliculate, sulfosalicylate, suramate, tannate, tartrate, teoclate, terephthalate, thiocyanate, thiosalicylate, tosylate, tribrophenate, triethiodide, undecanoate, undecylenate, valerate, valproate, xinafoate, zinc and the like. (See Berge et al. (1977) "Pharmaceutical Salts," J. Pharm. Sci. 66:1-19.) In some embodiments, preferred pharmaceutically acceptable salts are those employing a hydrochloride anion.

Prodrugs of the disclosed compounds also will be appreciated to be within the scope of the invention. The term "prodrug" refers to a precursor of a biologically active pharmaceutical agent. Prodrugs undergo a chemical or a metabolic conversion to become a biologically active pharmaceutical agent. A prodrug can be converted ex vivo to the biologically active pharmaceutical agent by chemical transformative processes. In vivo, a prodrug is converted to the biologically active pharmaceutical agent by the action of a metabolic process, an enzymatic process or a degradative process that removes the prodrug moiety, such as a glycoside or acetyl group, to form the biologically active pharmaceutical agent. Other examples include addition of hydroxyl groups (Tsujikawa et al. 2011. Xenobiotica, 41(7), 578-584; Yamamoto et al. 1984. Xenobiotica, 14(11), 867-875), acyloxyalkoxycarbonyl derivatives, amino acids, vitamins, or peptides (Vig et al. 2013. Advanced Drug Delivery Reviews, 65(10), 1370-1385), which are generally added to the amine, and can be removed within the body by chemical reactions or enzymes, but other prodrugs and precursors, at the amine and other sites, should be understood to be within the scope of the invention (Simplício, Clancy, & Gilmer. 2008. Molecules, 13(3), 519-547; Shah, Chauhan, Chauhan, & Mishra (Eds.). 2020. Recent Advancement in Prodrugs. CRC Press).

Types of prodrugs contemplated to be within the scope and spirit of the invention therefore include compounds that are transformed in various organs or locations in the body (e.g., liver, kidney, G.I., lung, tissue) to release the active compound. For example, liver prodrugs will include active compounds conjugated with a polymer or chemical moiety that is not released until acted upon by liver cytochrome enzymes; CYP metabolism includes dealkylation, dehydrogenation, reduction, hydrolysis, oxidation, and the breakdown of aromatic rings. Kidney prodrugs will include active compounds conjugated to L-gamma-glutamyl or N-acetyl-L-gamma glutamic moieties so that they are metabolized by gamma-glutamyl transpeptidase before they are bioactive; alternatively, they may be conjugated to alkylglucoside moieties to create glycosylation-based prodrugs. Digestive or G.I. prodrugs will include those where an active compound is, e.g., formulated into microspheres or nanospheres that do not degrade until the spheres are subjected to an acidic pH; formulated with an amide that will resist biochemical degradation until colonic pH is achieved; or conjugated with a linear polysaccharide such as pectin that will delay activation until the combination reaches the bacteria in the colon. Besides these exemplary prodrug forms, many others will be known to those of ordinary skill.

Typical examples of prodrugs also include compounds with biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a disclosed compound. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

In some embodiments, a prodrug comprising a disclosed compound is an amino acid prodrug. Amino acid refers to molecules comprising an amine group, a carboxylic acid group and a side-chain that varies among different amino acids. In some embodiments, one or more amino acids are directly conjugated to a disclosed compound to prepare a prodrug thereof. In some embodiments, a linker is used to conjugate a disclosed compound to the one or more amino acids to prepare a prodrug thereof. In some embodiments, amino acid prodrugs improve poor solubility, poor permeability, sustained release, intravenous delivery, drug targeting, and metabolic stability of the parent drug. See, e.g., Vig et al., Advanced Drug Delivery Reviews, 2013; 65(10): 1370-1385.

In some embodiments, a disclosed compound is attached to a single amino acid which is either a naturally occurring amino acid or a synthetic amino acid. In some embodiments, a disclosed compound is attached to a dipeptide or tripeptide, which could be any combination of naturally occurring amino acids and/or synthetic amino acids. In some embodiments, the amino acids are selected from L-amino acids for digestion by proteases. In some embodiments a carrier peptide is attached to a disclosed compound through the carrier peptide's N-terminus, C-terminus, or side chain of an amino acid which may be either a single amino acid or part of a longer chain sequence (i.e., a dipeptide, tripeptide, oligopeptide, or polypeptide). The carrier peptide may also be (i) a homopolymer of a naturally occurring amino acid, (ii) a heteropolymer of two or more naturally occurring amino acids, (iii) a homopolymer of a synthetic amino acid, (iv) a heteropolymer of two or more synthetic amino acids, or (v) a heteropolymer of one or more naturally occurring amino acids and one or more synthetic amino acids. For example, carrier peptides may be homopolymers or heteropolymers of glutamic acid, aspartic acid, serine, lysine, cysteine, threonine, asparagine, arginine, tyrosine, and glutamine. Examples of peptides include, Lys, Ser, Phe, Gly-Gly-Gly, Leu-Ser, Leu-Glu, homopolymers of Glu and Leu, and heteropolymers of (Glu)n-Leu-Ser. In some embodiments, a prodrug comprising a disclosed compound is a vitamin prodrug. In some embodiments, the vitamin is pyridoxine. Pyridoxine is the 4-methanol form of vitamin B6. Transporters, such as SLC19A2 and SLC19A3, also known as thiamine transporters (THTR) 1 and 2, have been shown to transport pyridoxine. Such transport may be exploited using pyridoxine as a prodrug component. See, e.g., Yamashiro et al., J Biol Chem. 2020; 295(50):16998-17008.

Generally, the individual disclosed compounds shall be administered as part of a pharmaceutical composition or formulation, but will be prepared for inclusion in such composition or formulations as isolated or purified compounds. The terms "isolated," "purified," or "substantially pure" as used herein, refer to material that is substantially or essentially free from components that normally accompany the material when the material is synthesized, manufactured, or otherwise produced. An "isolated," "purified," or "substantially pure" preparation of a compound is accordingly defined as a preparation having a chromatographic purity (of the desired compound) of greater than 90%, more preferably greater than 95%, more preferably greater than 96%, more preferably greater than 97%, more preferably greater than 98%, more preferably greater than 99%, more preferably greater than 99.5%, and most preferably greater than 99.9%, as determined by area normalization of an HPLC profile or other similar detection method.

Preferably the substantially pure compound used in the invention is substantially free of any other active compounds which are not intended to be administered to a subject. In this context "substantially free" can be taken to mean that no active compound(s) other than the active compound intended to be administered to a subject are detectable by HPLC or other similar detection method, or are below a desired threshold of detection such as defined above.

In some embodiments, the disclosed compounds are formulated in a pharmaceutically acceptable oral dosage form. Oral dosage forms include oral liquid dosage forms (such as tinctures, drops, emulsions, syrups, elixirs, suspensions, and solutions, and the like) and oral solid dosage forms. In some embodiments, the disclosed compounds also may be prepared as formulations suitable for intramuscular, subcutaneous, intraperitoneal, or intravenous injection, comprising physiologically acceptable sterile aqueous or non-aqueous solutions, dispersions, suspensions or emulsions, liposomes, and sterile powders for reconstitution into sterile injectable solutions or dispersions.

The disclosed compounds now generally described will be more readily understood by reference to the following description and examples, which are included for the purposes of illustration of certain aspects of the embodiments of the invention. The following is not intended to limit the invention, as one of skill in the art would recognize from the teachings and examples herein that other techniques and methods can satisfy the claims and be employed without departing from the scope of the invention. Indeed, while this invention has been particularly shown and described with reference to certain exemplary embodiments, it will be understood by those skilled in the art that various changes in form and details may be made without departing from the scope or spirit of the invention encompassed by the appended claims.

b. Mixtures of Deuterated and Undeuterated Compounds

In some embodiments, a composition of the invention will be a mixture of one or more deuterium-substituted compounds and corresponding non-substituted compounds in a fixed ratio, and will contain a ratio of deuterium-substituted to non-substituted compounds (as mole ratio or mass ratio), including a pharmaceutically acceptable salt, hydrate, solvate or prodrug thereof, of 1:1, at least 1:1, at least 1.1:1, at least 1.2:1, at least 1.3:1, at least 1.4:1, at least 0.5:1, at least 1.6:1, at least 1.7:1, at least 1.8:1, at least 1.9:1, at least 2.0:1, at least 2.5:1, at least 3.0:1, at least 4.0:1, at least 5.0:1, at least 6.0:1, at least 7.0:1, at least 8.0:1, at least 9.0:1, and at least 10:1, at least 11:1, at least 12:1, at least 13:1, at least 14:1, at least 15:1, at least 16:1, at least 17:1, at least 18:1, at least 19:1, at least 20:1, at least 25:1, at least 30:1, at least 40:1, at least 50:1, at least 60:1, at least 70:1, at least 80:1, at least 90:1, and at least 100:1, including the exact above-listed ratios themselves.

In some embodiments, a composition of the invention will be a mixture of one or more deuterium-substituted compounds and corresponding non-substituted compounds in a fixed ratio, and will contain a ratio of non-substituted to deuterium-substituted compounds (as mole ratio or mass ratio), including a pharmaceutically acceptable salt, hydrate, solvate or prodrug thereof, of 1:1, at least 1:1, at least 1.1:1, at least 1.2:1, at least 1.3:1, at least 1.4:1, at least 0.5:1, at least 1.6:1, at least 1.7:1, at least 1.8:1, at least 1.9:1, at least 2.0:1, at least 2.5:1, at least 3.0:1, at least 4.0:1, at least 5.0:1, at least 6.0:1, at least 7.0:1, at least 8.0:1, at least 9.0:1, and at least 10:1, at least 11:1, at least 12:1, at least 13:1, at least 14:1, at least 15:1, at least 16:1, at least 17:1, at least 18:1, at least 19:1, at least 20:1, at least 25:1, at least 30:1, at least 40:1, at least 50:1, at least 60:1, at least 70:1, at least 80:1, at least 90:1, and at least 100:1, including the exact above-listed ratios themselves.

c. Stereoisomers and Enantiomeric Mixtures

The disclosed compounds may contain one or more asymmetric centers and give rise to enantiomers, diastereomers, and other stereoisomeric forms. Each chiral center may be defined, in terms of absolute stereochemistry, as (R)- or (S)-. The invention is meant to include all such possible isomers, as well as mixtures thereof, including racemic and optically pure forms.

Optically active (R)- and (S)-, (−)- and (+)-, or (D)- and (L)-isomers may be prepared using chiral synthons or chiral reagents, or resolved using conventional techniques. Various methods are known in the art for preparing optically active forms and determining activity. Such methods include standard tests described herein and other similar tests which are well known in the art. Examples of methods that can be used to obtain optical isomers of the compounds according to the present disclosure include the following: i) physical separation of crystals whereby macroscopic crystals of the individual enantiomers are manually separated. This technique may particularly be used if crystals of the separate enantiomers exist (i.e., the material is a conglomerate), and the crystals are visually distinct; ii) simultaneous crystallization whereby the individual enantiomers are separately crystallized from a solution of the racemate, possible only if the latter is a conglomerate in the solid state; iii) enzymatic resolutions whereby partial or complete separation of a racemate by virtue of differing rates of reaction for the enantiomers with an enzyme; iv) enzymatic asymmetric synthesis, a synthetic technique whereby at least one step of the synthesis uses an enzymatic reaction to obtain an enantiomerically pure or enriched synthetic precursor of the desired enantiomer; v) chemical asymmetric synthesis whereby the desired enantiomer is synthesized from an achiral precursor under conditions that produce asymmetry (i.e., chirality) in the product, which may be achieved using chiral catalysts or chiral auxiliaries; vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer; vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers; viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions; ix) enantiospecific synthesis from non-racemic precursors whereby the desired enantiomer is obtained from non-chiral starting materials and where the stereochemical integrity is not or is only minimally compromised over the course of the synthesis; x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions; xi) chiral gas chromatography whereby the racemate is volatilized and enantiomers are separated by virtue of their differing interactions in the gaseous mobile phase with a column containing a fixed non-racemic chiral adsorbent phase; xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane, which allows only one enantiomer of the racemate to pass through.

The disclosed compounds may be provided in a composition that is enantiomerically enriched, such as a mixture of enantiomers in which one enantiomer is present in excess, in particular to the extent of at least 50%, at least 55%, at least 60%, at least 65%, at least 70%, at least 75%, at least 80%, at least 85%, at least 90%, at least 95%, at least 98%, at least 99%, at least 99.5%, or at least 99.9%, and up to (and including) 100%.

When the compounds described herein contain olefinic double bonds or other centers of geometric asymmetry, and unless specified otherwise, it is intended that the compounds include both E and Z geometric isomers. Likewise, tautomeric forms are included.

d. Exemplary Features of Disclosed Empathogens and Mixtures Comprising Deuterated and Undeuterated Compounds In some embodiments, a disclosed compound has reduced clearance relative to its corresponding undeuterated compound. In some embodiments, a disclosed compound has reduced clearance relative to another therapeutic empathogen. In one representative example, the corresponding undeuterated compound of known compound MDMA-d3 is MDMA. In some embodiments, a disclosed compound has reduced clearance relative to MDMA. In some embodiments, a disclosed compound has reduced clearance relative to deuterated MDMA, e.g., MDMA-d3. In some embodiments, a disclosed compound has reduced clearance relative to bk-MDMA. In some embodiments, clearance is reduced by about or at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, or 200%. In some embodiments, clearance refers to intrinsic clearance. In some embodiments, intrinsic clearance is determined using a metabolic stability study comprising human liver microsomes.

In some embodiments, a disclosed compound has an increased half-life. relative to its corresponding undeuterated compound. In some embodiments, a disclosed compound has an increased half-life relative to another therapeutic empathogen. In some embodiments, a disclosed compound has an increased half-life relative to MDMA. In some embodiments, a disclosed compound has an increased half-life relative to deuterated MDMA, e.g., MDMA-d3. In some embodiments, a disclosed compound has an increased half-life relative to bk-MDMA. In some embodiments, the half-life of a disclosed compound is increased by about or at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, or 200%.

The use of an alternate isotope may change the kinetics of a chemical reaction. This phenomenon is known as the kinetic isotope effect ("KIE"). For example, substituting a deuterium for a hydrogen may affect the reaction rate; this phenomenon is known as the "deuterium kinetic isotope effect" (DKIE). The DKIE can range from about 1 (no effect) to 50 or more, meaning that a reaction can be fifty or more times slower when deuterium is substituted for hydrogen (see, e.g., Foster et al., Adv. Drug Res., 14:1-36 (1985); Kushner et al., Can. J. Physiol. Pharmacol. 77:79-88 (1999)). In some embodiments, the experimental or computed DKIE is at least 1.1, at least 1.2, at least 1.3, at least 1.4, at least 1.5, at least 1.6, at least 1.7, at least 1.8, at least 1.9, at least 2.0, at least 2.5, at least 3.0, at least 3.5, at least 4.0, at least 4.5, at least 5.0, at least 5.5, at least 6.0, at least 6.5, at least 7.0, at least 7.5, at least 8.0, at least 8.5, at least 9.0, at least 9.5, at least 10.0, at least 11.0, at least 12.0, at least 13.0, at least 14.0, at least 15.0, at least 20.0, at least 25.0, at least 30.0, at least 40.0, at least 45.0, or at least 50.

Deuterium (2H or D), also called "heavy hydrogen," is a stable isotope of hydrogen (1H) with a natural abundance in the Earth's oceans of approximately one atom per 6,500 of hydrogen (~154 ppm). Deuterium thus accounts for approximately 0.0154% (alternately, on a mass basis, 0.0308%) of all naturally occurring hydrogen in the oceans. "Non-substituted," "non-deuterated," and "undeuterated" may refer to compounds having no greater than the amount of deuterium expected as a percentage of naturally occurring hydrogen in a compound.

In some embodiments, incorporating deuterium in place of hydrogen will improve the pharmacodynamic and pharmacokinetic profiles of the disclosed compounds by modifying the metabolic fate while retaining the pharmacologic activity and selectivity of the compounds.

In some embodiments, the disclosed deuterated compounds will positively impact safety, efficacy, and/or tolerability, compared to undeuterated compounds.

In some embodiments, a composition having a mixture of substituted and non-substituted compounds will reduce or eliminate the need for "re-dosing" compared to the non-substituted compound or composition, i.e., wherein a second or further additional "booster" dose is used or is necessary to prolong the effects of a composition to achieve a desired or therapeutic effect. Often, for example, a booster dose is taken at about 90 to about 120 minutes after administration of the initial dose, in an amount of about half the initial dose. In some embodiments, the improved pharmacokinetics of the disclosed compounds when used in a composition having a mixture of substituted and non-substituted compounds will reduce or eliminate the need for such re-dosing. In some embodiments, reducing or eliminating re-dosing will reduce or eliminate one or more adverse events or unwanted side effects. In some embodiments, reducing or eliminating re-dosing will provide benefits relating to ease of administration and patient compliance. In some embodiments, a composition having a mixture of substituted and non-substituted compounds will have an improved pharmacokinetic profile compared to the substituted compound or composition, such as earlier onset, shorter time to peak effect, or longer peak effects. In some embodiments, a composition having a mixture of substituted and non-substituted compounds will have an improved pharmacokinetic profile compared to the non-substituted compound or composition, such as earlier onset, shorter time to peak effect, or longer peak effects.

In some embodiments, a disclosed compound or composition will reduce or eliminate the need for "re-dosing" compared to the corresponding non-substituted compound or composition. In some embodiments, a disclosed compound or composition reduces or eliminates the need for re-dosing because of an improved in vivo pharmacokinetic profile, which may include a longer half-life.

In some embodiments, a disclosed compound or composition has a reduced rate of metabolism by N-demethylation or N-dealkylation relative to a corresponding non-substituted compound or composition, in an amount of at least a 5% reduction, at least a 10% reduction, at least a 15% reduction, at least a 25% reduction, at least a 50% reduction, at least a 75% reduction, at least a 90% reduction, at least a 95% reduction, or at least a 99% reduction.

In some embodiments, a disclosed compound has increased clearance relative to its corresponding undeuterated compound. In some embodiments, a disclosed compound has increased clearance relative to another therapeutic empathogen. In some embodiments, a disclosed compound has increased clearance relative to MDMA. In some embodiments, a disclosed compound has increased clearance relative to deuterated MDMA, e.g., MDMA-d3. In some embodiments, a disclosed compound has increased clearance relative to bk-MDMA. In some embodiments, clearance of a disclosed compound is increased by about or at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, or 200%.

In some embodiments, a disclosed compound has a reduced half-life relative to its corresponding undeuterated compound. In some embodiments, a disclosed compound has a reduced half-life relative to another therapeutic empathogen. In some embodiments, a disclosed compound has a reduced half-life relative to MDMA. In some embodiments, a disclosed compound has a reduced half-life relative to deuterated MDMA, e.g., MDMA-d3. In some embodiments, a disclosed compound has a reduced half-life relative to bk-MDMA. In some embodiments, the half-life of a disclosed compound is reduced by about or at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, or 200%.

In some embodiments, a disclosed compound has reduced adverse events relative to a corresponding non-substituted compound, in an amount for at least one adverse event of at least a 5% reduction, at least a 10% reduction, at least a 15% reduction, at least a 25% reduction, at least a 50% reduction, at least a 75% reduction, at least a 90% reduction, at least a 95% reduction, at least a 99% reduction, or a reduction beyond the threshold of measurement, whether determined within-patient or across patients or patient groups, or in a rodent or other suitable animal model, or determined in vitro, in silico, or otherwise measured using a standard such as one known to those of ordinary skill for the determination or quantification of the adverse event(s) in question, such as relating to anxiety, cardiovascular effects such as blood pressure and heart rate, hyperthermia, hyperhidrosis, jaw tightness and bruxism, muscle tightness, psychostimulation, appetite, nausea, concentration, and balance, as well as markers for or correlated with potential neurotoxicity, and including such exemplary tests and procedures that are in silico (e.g., computer analysis or simulation, including by AI, machine learning, or deep learning), in vitro (e.g., biochemical assays, tissue culture), and in vivo (e.g., behavioral assessment; functional observational batteries; tests of motor activity, schedule-controlled operant behavior, neurological function, neurophysiological function, nerve-conduction, evoked-potential; neurochemical, neuroendocrine, or neuropathological measures; EEG; imaging), as well as the use of physiological biomarkers (body temperature; heart rate; respiratory rate; blood oxygenation; systolic blood pressure (SBP); diastolic blood pressure (DBP); mean arterial pressure (MAP); pulse pressure (PP); Continuous Beat-by-Beat Blood Pressure (CNIBP); heart rate variability (HRV); hemodynamic response (HR); glucose; cortisol; serotonin; dopamine; and brain derived neurotrophic factor (BDNF)), and patient assessments.

In some embodiments, a disclosed compound or composition thereof does not cause a neurotoxic effect, such as in an in vitro assay or upon administration to a subject. In some embodiments, a disclosed compound or composition thereof causes a reduced neurotoxic effect, such as in an in vitro assay or upon administration to a subject. In some embodiments, the reduction of a neurotoxic effect is at least a 5% reduction, at least a 10% reduction, at least a 15% reduction, at least a 25% reduction, at least a 50% reduction, at least a 75% reduction, at least a 90% reduction, or at least a 95% reduction, or at least a 99% reduction, relative to a comparator. In some embodiments, the comparator is the disclosed compound's corresponding undeuterated compound. In some embodiments, the comparator is MDMA and/or MDMA-d3.

In some embodiments, the neurotoxic effect is determined by measuring one or more of: a) at least one toxic metabolite of MDMA or at least one toxic metabolite of an MDMA analog; b) oxidative stress and dopamine-based quinones; c) mitochondrial dysfunction; and d) activation of glial cells.

In some embodiments, neurotoxicity or a reduction thereof is determined by measuring the generation of toxic metabolites, e.g., MDA, such as from evaluating levels in blood, brain, or cerebrospinal fluid (CSF) samples. In some embodiments, neurotoxicity or a reduction thereof is determined by evaluating oxidative stress and dopamine-based quinones. In some embodiments, neurotoxicity or a reduction thereof is determined by evaluating activity and gene expression of antioxidant enzymes and/or pathways. In some embodiments, neurotoxicity or a reduction thereof is determined by measuring reactive oxygen species (ROS) production. See, e.g., Costa et al.'s assessment of superoxide dismutase and ubiquitin-proteasome system expression and activity in mouse neurons (Costa et al., Front Pharmacol. 2021; 12:713486). In humans, oxidative stress associated with administration of MDMA has been shown using blood samples. Specifically, Zhou et al., determined higher levels of erythrocyte lipoperoxide, superoxide dismutase, and catalase, and lower levels of plasma vitamin C, vitamin E, and carotene, in MDMA abusers (Zhou et al., Free Radic Res. 2003; 37(5):491-7).

In some embodiments, neurotoxicity or a reduction thereof is determined by evaluating mitochondrial dysfunction. Mitochondrial dysfunction may be evaluated by measuring one or more of mitochondrial membrane potential (MMP), mitochondrial swelling, mitochondrial outer membrane damage, the mitochondrial cytochrome c release, and ADP/ATP ratio. See, e.g., Taghizadeh et al.'s assessment of MDMA toxicity in mice, which showed markers of mitochondrial dysfunction following administration of MDMA, including significant increase in ROS formation, collapse of MMP, mitochondrial swelling, outer membrane damage, cytochrome c release from the mitochondria, and increased ADP/ATP ratio (Taghizadeh et al., Free Radic. Biol. Med. 2016; 99: 11-19).

In some embodiments, neurotoxicity or a reduction thereof is determined by assessing the activation of glial cells. Activation of quiescent glial cells by MDMA, MDA, and thioether metabolites of MDA derived from α-methyldopamine has been described, e.g., by Herndon et al., Toxicological Sciences, 2014; 138(1):130-138. Reactive astrogliosis can be measured with glial fibrillary acidic protein (GFAP) staining, and microglia reactivity can be visualized by immunostaining complement type 3 receptor (CD11b). See, e.g., Frau et al., J Neurochem. 2013; 124(1): 69-78 and Frau et al., Neurotoxicology. 2016; 56:127-138.

In embodiments, neurotoxicity or a reduction thereof is determined in vitro. In embodiments, neurotoxicity or a reduction thereof is determined in vivo.

The empathogen 3,4-methylenedioxymethamphetamine (MDMA) has shown promise in rapidly and effectively treating mental health disorders when taken in combination with psychotherapy. Findings from a randomized, double-blind, placebo-controlled, multi-site phase 3 clinical trial demonstrated that, compared to therapy with inactive placebo, MDMA-assisted therapy is highly efficacious in individuals with severe PTSD, and treatment is safe and well-tolerated, even in those with comorbidities (Mitchell et al., Nat. Med., 2021; 27, 1025-1033). Studies have demonstrated potential for MDMA to address other difficult-to-treat mental health conditions, including substance abuse, obsessive compulsive disorder (OCD), phobias, eating disorders, depression, end-of-life anxiety, and social anxiety.

Although MDMA generally produces no long-lasting or serious adverse events, it is known to cause transient adverse events that are mild to moderate in severity, including increased anxiety, cardiovascular effects such as increased blood pressure and heart rate, hyperthermia, hyperhidrosis, jaw tightness and bruxism, muscle tightness, unpleasant stimulation, reduced appetite, nausea, poor concentration, and impaired balance (see, e.g., Harris et al., Psychopharmacology (Berl), 2002; 162(4), 396-405; Lietchti 2001, Oehen et al., J. Psychopharmacol, 2013; 40-52; Mas et al., J. Pharmacol Exp. Ther., 1999; 290(1): 136-45, Mithoefer, et al., J. of Psychopharmacology, 2010; 25(4): 439-452; Rogers et al., Health Technol. Assess, 2009; 13(6): iii-iv, ix-xii, 1-315). Accordingly, compounds that can harness the therapeutic benefits of MDMA without its negative side effects have been highly sought after. Mitigating one or more of these side effects and improving the safety profile would both increase the value of an empathogen for therapeutic use, and broaden the population of patients who could benefit.

MDMA is metabolized in the liver, predominantly by the enzymatic activity of CYP2D6, CYP2B6, CYP1A2, and CYP2C19. Hepatic metabolism of MDMA by CYP2B6, CYP1A2, and CYP2C19 results in formation of the N-demethylated primary metabolite 3,4-methylenedioxyamphetamine (MDA). Evidence has shown that MDA may be responsible for the side effects associated with MDMA ingestion, such as described above, as well as serotonin depletion, serotonergic nerve terminal degeneration, and neuronal apoptosis. Accordingly, protecting MDMA from N-dealkylation may result in fewer adverse events.

B. Chemical Synthesis

In some aspects, provided herein are methods of preparing the disclosed therapeutic empathogens, such as compounds of Formula (I), Formula (II), Formula (III), and Formula (IV). In some embodiments, the method of preparing a disclosed compound comprises reductive amination. In some embodiments, the method of preparing a disclosed compound comprises a Leuckart reaction. In some embodiments, the method of preparing a disclosed compound comprises amination of alkyl halides.

In some embodiments, disclosed compounds can be synthesized following the reaction schemes provided in the scheme below:

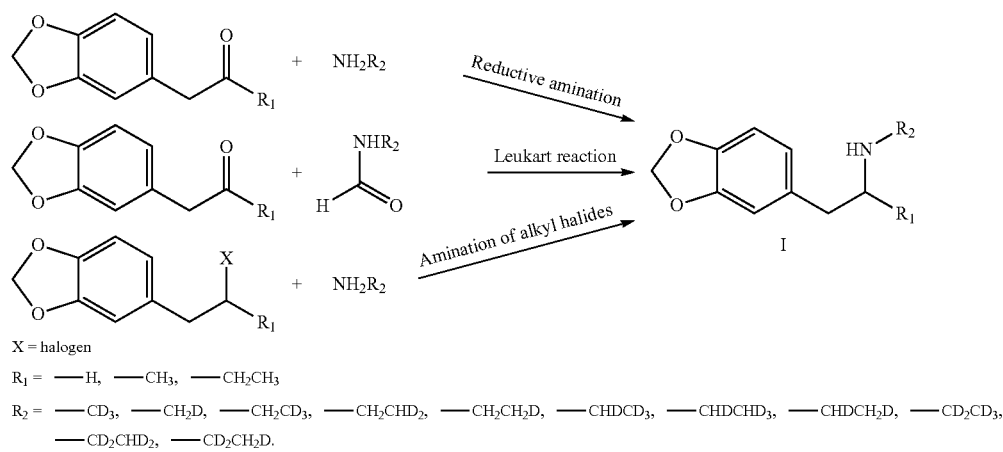

X = halogen
R₁ = —H, —CH₃, —CH₂CH₃
R₂ = —CD₃, —CH₂D, —CH₂CD₃, —CH₂CHD₂, —CH₂CH₂D, —CHDCD₃, —CHDCHD₂, —CHDCH₂D, —CD₂CD₃, —CD₂CHD₂, —CD₂CH₂D.

In an embodiment, deuterated analogs of any Formula (I), Formula (II), Formula (III), and Formula (IV) are synthesized by reductive amination of an aldehyde or ketone with a primary amine. In another embodiment, deuterated analogs of any of Formula (I), Formula (II), Formula (III), and Formula (IV) are synthesized by Leuckart reaction, wherein an aldehyde or ketone is treated with a formamide derivative. In yet another embodiment, deuterated analogs of any of Formula (I), Formula (II), Formula (III), and Formula (IV) are synthesized by amination of alkyl halides, wherein alkyl halides are treated with primary amines.

In some embodiments, deuterated methylone compounds of any of Formula (I), Formula (II), and Formula (IV)) of the invention can be synthesized following the reaction scheme provided in the scheme below:

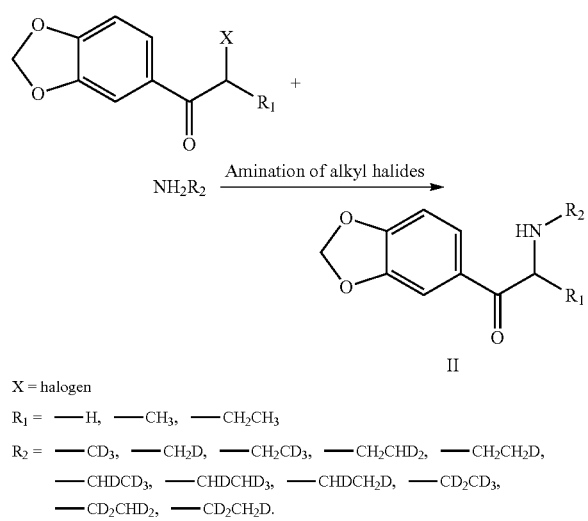

X = halogen
R₁ = —H, —CH₃, —CH₂CH₃
R₂ = —CD₃, —CH₂D, —CH₂CD₃, —CH₂CHD₂, —CH₂CH₂D, —CHDCD₃, —CHDCHD₂, —CHDCH₂D, —CD₂CD₃, —CD₂CHD₂, —CD₂CH₂D.

In an embodiment, deuterated analogs of any of Formula (I), Formula (II), and Formula (IV) are synthesized by amination of alkyl halides. For example, alpha-halo carbonyl compounds are treated with primary amines to synthesize deuterated analogs of any of Formula (I), Formula (II), and Formula (IV).

Additional methods for synthesis of the compounds described herein and any necessary starting materials are either described in the art or will be readily apparent to the skilled artisan in view of general references well-known in the art (see, e.g., Green et al., "Protective Groups in Organic Chemistry," (Wiley, 2nd ed. 1991); Harrison et al., "Compendium of Synthetic Organic Methods," Vols. 1-8 (John Wiley and Sons, 1971-1996); "Beilstein Handbook of Organic Chemistry," Beilstein Institute of Organic Chemistry, Frankfurt, Germany; Feiser et al, "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995) and may be used to synthesize the disclosed compounds.

In general, the approaches used for similar compounds (Shulgin & Shulgin. 1992. PiHKAL. A chemical love story, Transform Press, Berkeley CA; Glennon et al. 1986. J. Med. Chem., 29(2), 194-199; Nichols et al. 1991. J. Med. Chem., 34(1), 276-281; Kedrowski et al. 2007. Organic Letters, 9(17), 3205-3207; Heravi & Zadsirjan. 2016. Current Organic Synthesis, 13(6), 780-833; Keri et al. 2017. European J. Med. Chem., 138, 1002-1033; Pérez-Silanes et al. 2001. J. Heterocyclic Chem, 38(5), 1025-1030; and references therein), such adaptation being that known and understood to those of ordinary skill.

C. Pharmaceutical Compositions

In some aspects, provided herein are compositions, such as pharmaceutical compositions, comprising the disclosed compounds, such as compounds of any of Formula (I), Formula (II), Formula (III), and Formula (IV). While it is possible to administer a compound employed in the methods of this invention directly without any formulation, the compounds are usually administered in the form of pharmaceutical compositions.

"Pharmaceutical compositions" are compositions that include the disclosed compound(s) together in an amount (for example, in a unit dosage form) with a pharmaceutically acceptable carrier, diluent, or excipient. It should be understood that some embodiments do not have a single carrier, diluent, or excipient alone, but include multiple carriers, diluents, and/or excipients. Compositions can be prepared by standard pharmaceutical formulation techniques such as disclosed in, e.g., Remington: The Science and Practice of Pharmacy (2020) 23th ed., Academic Press., Cambridge, Mass.; The Merck Index (1996) 12th ed., Merck Publishing Group, Whitehouse, N.J.; Pharm. Principles of Solid Dosage Forms (1993), Technomic Publishing Co., Inc., Lancaster, Pa.; and Ansel and Stoklosa, Pharm. Calculations (2001) 11th ed., Lippincott Williams & Wilkins, Baltimore, Md.; and Poznansky et al. Drug Delivery Systems (1980), R. L. Juliano, ed., Oxford, N.Y., pp. 253-315).

"Pharmaceutically acceptable" as used in connection with an excipient, carrier, diluent, or other ingredient means that the ingredient is generally safe and, within the scope of sound medical judgment, suitable for use in contact with the cells of humans and other animals without undue toxicity, irritation, allergic response, or complication, and commensurate with a reasonable risk/benefit ratio.

In some embodiments, pharmaceutical compositions comprising a compound of any of Formula (I), Formula (II), Formula (III), and Formula (IV) can be administered by a variety of routes including oral, mucosal (e.g., buccal, sublingual), rectal, transdermal, subcutaneous, intravenous, intramuscular, inhaled, and intranasal. In some embodiments, the compounds employed in the methods of this invention are effective as oral, mucosal (e.g., buccal, sublingual), rectal, transdermal, subcutaneous, intravenous, intramuscular, inhaled, and intranasal compositions. Such compositions are prepared in a manner well known in the pharmaceutical art and comprise at least one active compound. (See, e.g., Remington, 2020.)

In making the compositions employed in the invention the active ingredient is usually mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier, or medium for the active ingredient. Thus, the compositions can be in the form of tablets (including orally disintegrating, swallowable, sublingual, buccal, and chewable tablets), pills, powders, lozenges, troches, oral films, thin strips, sachets, cachets, elixirs, suspensions, emulsions, microemulsions, liposomal dispersions, aqueous and non-aqueous solutions, slurries, syrups, aerosols (as a solid or in a liquid medium), ointments containing for example up to 10% by weight of the active compound, soft and hard gelatin capsules, suppositories, topical preparations, transdermal patches, sterile injectable solutions, and sterile packaged powders. Compositions may be formulated as immediate release, controlled release, sustained (extended) release or modified release formulations. In some embodiments, the composition is prepared as a dry powder for inhalation or a liquid preparation for vaporization and inhalation, and is administered, e.g., using an electronic cigarette or other vaping device, a nebulizer, a pressurized metered dose inhaler (pMDI), or a dry powder inhaler (DPI).

It should be readily appreciated that the compositions of the invention are not limited to combinations of a single compound, or (when formulated as a pharmaceutical composition) limited to a single carrier, diluent, and/or excipient alone, but may also include combinations of multiple compounds (including additional active compounds), and/or multiple carriers, diluents, and excipients. Pharmaceutical compositions of this invention thus may comprise a compound of any of Formula (I), Formula (II), Formula (III), and Formula (IV) together with one or more other active agents (or their derivatives and analogs) in combination, together with one or more pharmaceutically-acceptable carriers, diluents, and/or excipients, and additionally with one or more other active compounds.

In some embodiments, a composition or formulation of the invention (the terms being used interchangeably herein, unless context demands otherwise) will be prepared so as to increase an existing therapeutic effect, provide an additional therapeutic effect, increase a desired property such as stability or shelf-life, decrease an unwanted effect or property, alter a property in a desirable way (such as pharmacokinetics or pharmacodynamics), modulate a desired system or pathway (e.g., a neurotransmitter system), or provide synergistic effects.

"Therapeutic effects" that may be increased or added in embodiments of the invention include, but are not limited to, antioxidant, anti-inflammatory, analgesic, antineuropathic, antinociceptive, antimigraine, anxiolytic, antidepressant, antipsychotic, anti-PTSD, dissociative, immunostimulant, anti-cancer, antiemetic, orexigenic, antiulcer, antihistamine, antihypertensive, anticonvulsant, antiepileptic, bronchodilator, neuroprotective, empathogenic, psychedelic, sedative, and stimulant effects.

"Synergistic effects" should be understood to include increases in potency, bioactivity, bioaccessibility, bioavailability, or therapeutic effect, that are greater than the additive contributions of the components acting alone. Numerous methods known to those of skill in the art exist to determine whether there is synergy as to a particular effect, i.e., whether, when two or more components are mixed together, the effect is greater than the sum of the effects of the individual components when applied alone, thereby producing "1+1>2." One such method is the isobologram analysis (or contour method) (see Huang, Front Pharmacol., 2019; 10:1222).

The goal of increasing an existing therapeutic effect, providing an additional therapeutic effect, increasing a desired property such as stability or shelf-life, decreasing an unwanted effect or property, altering a property in a desirable way (such as pharmacokinetics or pharmacodynamics), modulating a desired system or pathway (e.g, a neurotransmitter system), or otherwise inducing synergy, in some embodiments is achieved by the inclusion of an additional active compound.

Such additional active compounds may be selected from the group including amino acids, antioxidants, anti-inflammatory agents, analgesics, antineuropathic and antinociceptive agents, antimigraine agents, anxiolytics, antidepressants, antipsychotics, anti-PTSD agents, cannabinoids, dissociatives, immunostimulants, anti-cancer agents, antiemetics, orexigenics, antiulcer agents, antihistamines, antihypertensives, anticonvulsants, antiepileptics, bronchodilators, neuroprotectants, empathogens, psychedelics, monoamine oxidase inhibitors, tryptamines, terpenes, phenethylamines, sedatives, stimulants, nootropics, and vitamins. These ingredients may be in ion, freebase, or salt form, and may be isomers, prodrugs, derivatives (preferably physiologically functional derivatives), or analogs.

In some embodiments, an additional active compound is a tryptamine. "Tryptamines" are as readily understood by those in the art, and non-limiting examples include: 6-Allyl-N,N-diethyl-norlysergic acid (AL-LAD), N,N-dibutyl-tryptamine (DBT), N,N-diethyl-tryptamine (DET), N,N-diisopropyl-tryptamine (DiPT), 5-methyoxy-α-methyl-tryptamine (α,O-DMS), N,N-dimethyl-tryptamine (DMT), 2,α-dimethyl-tryptamine (2,α-DMT), α,N-dimethyl-tryptamine (α,N-DMT), N,N-dipropyl-tryptamine (DPT), N-ethyl-N-isopropyl-tryptamine (EiPT), α-ethyl-tryptamine (AET), 6,N,N-tryptamineriethyl-norlysergic acid (ETH-LAD), 3,4-dihydro-7-methoxy-1-methyl-carboline (Harmaline), 7-methyoxy-1-methyl-carboline (Harmine), N,N- dibutyl-4-hydroxy-tryptamine (4-HO-DBT), N,N-diethyl-4-hydroxy-tryptamine (4-HO-DET), N,N-diisopropyl-4-hydroxy-tryptamine (4-HO-DiPT), N,N-dimethyl-4-hydroxy-tryptamine (4-HO-DMT), N,N-dimethyl-5-hydroxy-tryptamine (5-HO-DMT), N,N-dipropyl-4-hydroxy-tryptamine (4-HO-DPT), N-ethyl-4-hydroxy-N-methyl-tryptamine (4-HO-MET), 4-hydroxy-N-isopropyl-N-methyl-tryptamine (4-HO-MiPT), 4-hydroxy-N-methyl-N-propyl-tryptamine (4-HO-MPT), 4-hydroxy-N,N-tetramethylene-tryptamine (4-HO-pyr-tryptamine), 12-methoxyibogamine (Ibogaine), N-butyl-N-methyl-tryptamine (MBT), N,N-diisopropyl-4,5-methylenedioxy-tryptamine (4,5-MDO-DiPT), N,N-diisopropyl-5,6-methylenedioxy-tryptamine (5,6-MDO-DiPT), N,N-dimethyl-4,5-methylenedioxy-tryptamine (4,5-MDO-DMT), N,N-dimethyl-5,6-methylenedioxy-tryptamine (5,6-MDO-DMT), N-isopropyl-N-methyl-5,6-methylenedioxy-tryptamine (5,6-MDO-MiPT), N,N-diethyl-2-methyl-tryptamine (2-Me-DET), 2,N,N-tryptaminerimethyl-tryptamine (2-Me-DMT), N-acetyl-5-methoxy-tryptamine (melatonin), N,N-diethyl-5-methoxy-tryptamine (5-MeO-DET), N,N-diisopropyl-5-methoxy-tryptamine (5-MeO-DiPT), 5-methoxy-N,N-dimethyl-tryptamine (5-MeO-DMT), N-isopropyl-4-methoxy-N-methyl-tryptamine (4-MeO-MiPT), N-isopropyl-5-methoxy-N-methyl-tryptamine (5-MeO-MiPT), 5,6-dimethoxy-N-isopropyl-N-methyl-tryptamine (5,6-MeO-MiPT), 5-methoxy-N-methyl-tryptamine (5-MeO-NMT), 5-methoxy-N,N-tetramethylene-tryptamine (5-MeO-pyr-tryptamine), 6-methoxy-1-methyl-1,2,3,4-tetrahydro-carboline (6-MeO-tryptamineHH), 5-methoxy-2,N,N-trimethyl-tryptamine (5-MeO-tryptamineMT), N,N-dimethyl-5-methylthio-tryptamine (5-MeS-DMT), N-isopropyl-N-methyl-tryptamine (MiPT), α-methyl-tryptamine (α-MT), N-ethyl-tryptamine (NET), N-methyl-tryptamine (NMT), 6-propyl-norlysergic acid (PRO-LAD), N,N-tetramethylene-tryptamine (pyr-T), Tryptamine (T), 7-methoxy-1-methyl-1,2,3,4-tetrahydrocarboline (Tetrahydroharmine), or α,N-dimethyl-5-methoxy-tryptamine (α,N,O-TMS), or a pharmaceutically acceptable salt, hydrate, solvate, prodrug, stereoisomer, or tautomer thereof, or a combination thereof. See Shulgin and Shulgin, TIHKAL: The Continuation, Transform Press (1997), which is incorporated by reference herein for the specific teachings thereof.

In embodiments, a tryptamine useful as an additional active compound will be a substituted tryptamine having the structure below, wherein $R^{N1}$, $R^{N2}$, $R^\alpha$, $R^\beta$, $R^2$, $R^4$, $R^5$, $R^6$, and $R^7$ will be as taught herein and as generally understood in the art:

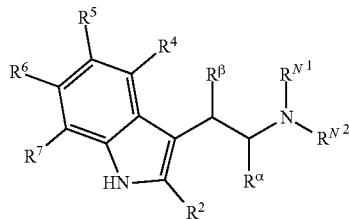

For example, in some embodiments, $R^{N1}$, $R^{N2}$, $R^\alpha$, $R^\beta$, $R^2$, $R^4$, $R^5$, $R^6$, and $R^7$ are independently hydrogen, deuterium, halogen, hydroxy, methoxy, phosphoryloxy, $C_1$-$C_5$ alkyl, $C_2$-$C_8$ alkenyl, $C_2$-$C_8$ alkynyl, $C_3$-$C_8$ cycloalkyl (independently or ring closed with the nitrogen), $C_3$—$C_8$ cycloalkenyl (independently or ring closed with the nitrogen), aryl, or heterocyclyl, any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, —OP(O)(OH)$_2$, —OC(O)H, —OSO$_2$H, —OC(O)NH$_2$, and —SONH. In some embodiments, the tryptamine comprises a quaternary ammonium cation wherein each of $R^{N1}$, $R^{N2}$, and an additional $R^{N3}$ are independently an alkyl group or an aryl group, and with all other substituents as above.

In some embodiments, an additional tryptamine of the invention will be a "complex tryptamine" or other indolamine and including such non-limiting examples as ergolines, lysergamides, ibogaine and its analogs and derivatives, and beta-carbolines.

In some embodiments, the additional active compound is a phenethylamine. Non-limiting examples of phenethylamines useful in the practice of the invention include: α-ethyl-3,4,5-trimethoxy-phenethylamine (AEM), 4-allyloxy-3,5-dimethoxy-phenethylamine (AL), 4-methylthio-2,5-dimethoxy-amphetamine (ALEPH), 4-ethylthio-2,5-dimethoxy-amphetamine (ALEPH-2), 4-isopropylthio-2,5-dimethoxy-amphetamine (ALEPH-4), 4-phenylthio-2,5-dimethoxy-amphetamine (ALEPH-6), 4-propylthio-2,5-dimethoxy-amphetamine (ALEPH-7), 2,5-dimethoxy-α-ethyl-4-methyl-phenethylamine (ARIADNE), 3,4-diethoxy-5-methoxy-phenethylamine (ASB), 4-butoxy-3,5-dimethoxy-phenethylamine (B), 2,5-dimethoxy-4,N-dimethyl-amphetamine (BEATRICE), 2,5-bismethylthio-4-methyl-amphetamine (BIS-TOM), 4-bromo-2,5,β-trimethoxy-phenethylamine (BOB), 2,5,β-trimethoxy-4-methyl-phenethylamine (BOD), p-methoxy-3,4-methylenedioxy-phenethylamine (BOH), 2,5-dimethoxy-β-hydroxy-4-methyl-phenethylamine (BOHD), 3,4,5,β-tetramethoxy-phenethylamine (BOM), 4-bromo-3,5-dimethoxy-amphetamine (4-Br-3,5-DMA), 2-bromo-4,5-methylenedioxy-amphetamine (2-Br-4,5-MDA), 4-bromo-2,5-dimethoxy-phenethylamine (2C-B), 4-benzyloxy-3,5-dimethoxy-amphetamine (3C-BZ), 4-chloro-2,5-dimethoxy-phenethylamine (2C-C), 4-methyl-2,5-dimethoxy-phenethylamine (2C-D), 4-ethyl-2,5-dimethoxy-phenethylamine (2C-E), 4-ethoxy-3,5-dimethoxy-amphetamine (3C-E), 4-fluoro-2,5-dimethoxy-phenethylamine (2C-F), 3,4-dimethyl-2,5-dimethoxy-phenethylamine (2C-G), 3,4-trimethylene-2,5-dimethoxy-phenethylamine (2C-G-3), 3,4-tetramethylene-2,5-dimethoxy-phenethylamine (2C-G-4), 3,4-norbornyl-2,5-dimethoxy-phenethylamine (2C-G-5), 1,4-dimethoxynaphthyl-2-ethylamine (2C-G-N), 2,5-dimethoxy-phenethylamine (2C-H), 4-iodo-2,5-dimethoxy-phenethylamine (2C-I), 4-nitro-2,5-dimethoxy-phenethylamine (2C-N), 4-isopropoxy-2,5-dimethoxy-phenethylamine (2C-G-4), 4-propyl-2,5-dimethoxy-phenethylamine (2C-P), 4-cyclopropylmethoxy-3,5-dimethoxy-phenethylamine (CPM), 4-methylseleno-2,5-dimethoxy-phenethylamine (2C-SE), 4-methylthio-2,5-dimethoxy-phenethylamine (2C-T), 4-ethylthio-2,5-dimethoxy-phenethylamine (2C-T-2), 4-isopropylthio-2,5-dimethoxy-phenethylamine (2C-T-4), 4-isopropylthio-2,6-dimethoxy-phenethylamine (psi-2C-T-4), 4-propylthio-2,5-dimethoxy-phenethylamine (2C-T-7), 4-cyclopropylmethylthio-2,5-dimethoxy-phenethylamine (2C-T-8), 4-(t)-butylthio-2,5-dimethoxy-phenethylamine (2C-T-9), 4-(2-methoxyethylthio)-2,5-dimethoxy-phenethylamine (2C-T-13), 4-cyclopropylthio-2,5-dimethoxy-phenethylamine (2C-T-15), 4-(s)-butylthio-2,5-dimethoxy-phenethylamine (2C-T-17), 4-(2-fluoroethylthio)-2,5-dimethoxy-phenethylamine (2C-T-21), 4-trideuteromethyl-3,5-dimethoxy-phenethylamine (4-D), β,β-dideutero-3,4,5-trimethoxy-phenethylamine (B-D), 4-methyl-3,5-dimethoxy-phenethylamine (DESOXY), 2,4-dimethoxy-amphetamine (2,4-DMA),2,5-dimethoxy-amphetamine (2,5-DMA), 3,4-dimethoxy-amphetamine (3,4-DMA), 2-(2,5-dimethoxy-4-methylphenyl)-cyclopropylamine (DMCPA), 3,4-dimethoxy-β-hydroxy-phenethylamine (DME), 2,5-dimethoxy-3,4-methylenedioxy-amphetamine (DMMDA), 2,3-dimethoxy-4,5-methylenedioxy-amphetamine (DMMDA-2), 3,4-dimethoxy-phenethylamine (DMPEA), 4-amyl-2,5-dimethoxy-amphetamine (DOAM), 4-bromo-2,5-dimethoxy-amphetamine (DOB), 4-butyl-2,5-dimethoxy-amphetamine (DOBU), 4-chloro-2,5-dimethoxy-amphetamine (DOC), 4-(2-fluoroethyl)-2,5-dimethoxy-amphetamine (DOEF), 4-ethyl-2,5-dimethoxy-amphetamine (DOET), 4-iodo-2,5-dimethoxy-amphetamine (DOI), 4-methyl-2,5-dimethoxy-amphetamine (DOM (STP)), 4-methyl-2,6-dimethoxy-amphetamine (psi-DOM), 4-nitro-2,5-dimethoxy-amphetamine (DON), 4-propyl-2,5-dimethoxy-amphetamine (DOPR), 4-ethoxy-3,5-dimethoxy-phenethylamine (E), 2,4,5-triethoxy-amphetamine (EEE), 2,4-diethoxy-5-methoxy-amphetamine (EEM), 2,5-diethoxy-4-methoxy-amphetamine (EME), 2-ethoxy-4,5-dimethoxy-amphetamine (EMM), N,α-diethyl-3,4-methylenedioxy-phenethylamine (ETHYL-J), N-ethyl-α-propyl-3,4-methylenedioxy-phenethylamine (ETHYL-K), benzofuran-2-methyl-5-methoxy-6-(2-aminopropane) (F-2), benzofuran-2,2-dimethyl-5-methoxy-6-(2-aminopropane) (F-22), N-hydroxy-N-methyl-3,4-methylenedioxy-amphetamine (FLEA), 3,4-trimethylene-2,5-dimethoxy-amphetamine (G-3), 3,4-tetramethylene-2,5-dimethoxy-amphetamine (G-4), 3,4-norbornyl-2,5-dimethoxy-amphetamine (G-5), 3,4-dimethyl-2,5-dimethoxy-amphetamine (GANESHA), 1,4-dimethoxynaphthyl-2-isopropylamine (G-N), 2,5-dimethoxy-N-hydroxy-4-ethylthio-phenethylamine (HOT-2), 2,5-dimethoxy-N-hydroxy-4-(n)-propylthio-phenethylamine (HOT-7), 2,5-dimethoxy-N-hydroxy-4-(s)-butylthio-phenethylamine (HOT-17), 2,5-dimethoxy-N,N-dimethyl-4-iodo-amphetamine (IDNNA), 2,3,4-trimethoxy-phenethylamine (IM), 3,5-dimethoxy-4-isopropoxy-phenethylamine (IP), 5-ethoxy-2-methoxy-4-methyl-amphetamine (IRIS), α-ethyl-3,4-methylenedioxy-phenethylamine (J), 3-methoxy-4,5-methylenedioxy-phenethylamine (LOPHOPHINE), 3,4,5-trimethoxy-phenethylamine (M), 4-methoxy-amphetamine (4-MA), 2,N-dimethyl-4,5-methylenedioxy-amphetamine (MADAM-6), 3,5-dimethoxy-4-methallyloxy-phenethylamine (MAL), 3,4-methylenedioxy-amphetamine (MDA), N-allyl-3,4-methylenedioxy-amphetamine (MDAL), N-butyl-3,4-methylenedioxy-amphetamine (MDBU), N-benzyl-3,4-methylenedioxy-amphetamine (MDBZ), N-Cyclopropylmethyl-3,4-methylenedioxy-amphetamine (MDCPM), N,N-dimethyl-3,4-methylenedioxy-amphetamine (MDDM), N-ethyl-3,4-methylenedioxy-amphetamine (MDE), N-(2-hydroxyethyl)-3,4-methylenedioxy-amphetamine (MDHOET), N-isopropyl-3,4-methylenedioxy-amphetamine (MDIP), N-methyl-3,4-methylenedioxy-amphetamine (MDMA), N-methyl-3,4-ethylenedioxy-amphetamine (MDMC), N-methoxy-3,4-methylenedioxy-amphetamine (MDMEO), N-(2-methoxyethyl)-3,4-methylenedioxy-amphetamine (MDMEOET), α,α,N-trimethyl-3,4-methylenedioxy-phenethylamine (MDMP), N-hydroxy-3,4-methylenedioxy-amphetamine (MDOH), 3,4-methylenedioxy-phenethylamine (MDPEA), α,α-dimethyl-3,4-methylenedioxy-phenethylamine (MDPH), N-propargyl-3,4-methylenedioxy-amphetamine (MDPL), N-propyl-3,4-methylenedioxy-amphetamine (MDPR), 3,4-dimethoxy-5-ethoxy-phenethylamine (ME), 3-methoxy-4,5-ethylenedioxy-amphetamine (MEDA), 2-methoxy-4,5-diethoxy-amphetamine (MEE), 2,5-dimethoxy-4-ethoxy-amphetamine (MEM), 3-methoxy-4-ethoxy-phenethylamine (MEPEA), 5-bromo-2,4-dimethoxy-amphetamine (META-DOB),5-methylthio-2,4-dimethoxy-amphetamine (META-DOT),N-methyl-2,5-dimethoxy-amphetamine (METHYL-DMA), 4-bromo-2,5-dimethoxy-N-methyl-amphetamine (METHYL-DOB), N-methyl-α-ethyl-3,4-methylenedioxy-phenethylamine (METHYL-J), N-methyl-α-propyl-3,4-methylenedioxy-phenethylamine (METHYL-K), N-methyl-4-methoxy-amphetamine (METHYL-MA),N-methyl-2-methoxy-4,5-methylenedioxy-amphetamine (METHYL-MMDA-2), 3-methoxy-4,5-methylenedioxy-amphetamine (MMDA), 2-methoxy-4,5-methylenedioxy-amphetamine (MMDA-2), 2-methoxy-3,4-methylenedioxy-amphetamine (MMDA-3a),4-methoxy-2,3-methylenedioxy-amphetamine (MMDA-3b), 2,4-dimethoxy-5-ethoxy-amphetamine (MME), 3,4-dimethoxy-5-propoxy-phenethylamine (MP),2,5-dimethoxy-4-propoxy-amphetamine (MPM), 2-methylthio-4,5-dimethoxy-amphetamine (ORTHO-DOT), 3,5-dimethoxy-4-propoxy-phenethylamine (P), 3,5-dimethoxy-4-phenethyloxy-phenethylamine (PE), phenethylamine (PEA), 4-propynyloxy-3,5-dimethoxy-phenethylamine (PROPYNYL), 3,5-diethoxy-4-methoxy-phenethylamine (SB),2,3,4,5-Tetramethoxy-amphetamine (TA),4-ethoxy-3-ethylthio-5-methoxy-phenethylamine (3-TASB), 3-ethoxy-4-ethylthio-5-methoxy-phenethylamine (4-TASB), 3,4-diethoxy-5-methylthio-phenethylamine (5-TASB), 4-thiobutoxy-3,5-dimethoxy-phenethylamine (TB), 4-ethoxy-5-methoxy-3-methylthio-phenethylamine (3-TE), 3,5-dimethoxy-4-ethylthio-phenethylamine (4-TE), 2-methylthio-3,4-dimethoxy-phenethylamine (2-TIM), 3-methylthio-2,4-dimethoxy-phenethylamine (3-TIM), 4-methylthio-2,3-dimethoxy-phenethylamine (4-TIM), 3-methylthio-4,5-dimethoxy-phenethylamine (3-TM), 4-methylthio-3,5-dimethoxy-phenethylamine (4-TM), 3,4,5-trimethoxy-amphetamine (TMA), 2,4,5-trimethoxy-amphetamine (TMA-2), 2,3,4-trimethoxy-amphetamine (TMA-3), 2,3,5-trimethoxy-amphetamine (TMA-4), 2,3,6-trimethoxy-amphetamine (TMA-5), 2,4,6-trimethoxy-amphetamine (TMA-6), 4,5-dimethoxy-3-ethylthio-phenethylamine (3-TME), 3-ethoxy-5-methoxy-4-methylthio-phenethylamine (4-TME), 3-ethoxy-4-methoxy-5-methylthio-phenethylamine (5-TME), 2-methylthio-3,4-methylenedioxy-amphetamine (2T-MMDA-3a), 4,5-thiomethyleneoxy-2-methoxy-amphetamine (4T-MMDA-2), 2,4,5-trimethoxy-phenethylamine (TMPEA), 4-ethyl-5-methoxy-2-methylthio-amphetamine (2-TOET), 4-ethyl-2-methoxy-5-methylthio-amphetamine (5-TOET), 5-methoxy-4-methyl-2-methylthio-amphetamine (2-TOM), 2-methoxy-4-methyl-5-methylthio-amphetamine (5-TOM), 2-methoxy-4-methyl-5-methylsulfinyl-amphetamine (TOMSO), 4-propylthio-3,5-dimethoxy-phenethylamine (TP), 3,4,5-triethoxy-phenethylamine (TRIS), 3-ethoxy-5-ethylthio-4-methoxy-phenethylamine (3-TSB), 3,5-diethoxy-4-methylthio-phenethylamine (4-TSB), 4,5-diethoxy-3-ethylthio-phenethylamine (3-T-TRIS), 3,5-diethoxy-4-ethylthio-phenethylamine (4-T-TRIS), (R)-2,5-dimethoxy-4-iodoamphetamine, or a pharmaceutically acceptable salt, hydrate, solvate, prodrug, stereoisomer, or tautomer thereof, or a combination thereof. See Shulgin and Shulgin, PIHKAL: A Chemical Love Story, Transform Press (1994), which is incorporated by reference herein for the specific teachings thereof.

In embodiments, a phenethylamine useful as an additional active compound will be a substituted phenethylamine having the structure below, wherein $R^{N1}$, $R^{N2}$, $R^{\alpha}$, $R^{\beta}$, and each of $R^{2-6}$ will be as taught herein and as generally understood in the art:

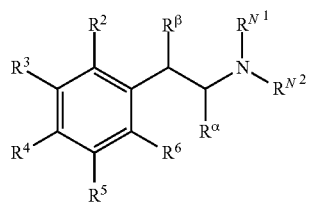

For example, in some embodiments, $R^{N1}$, $R^{N2}$, $R^{\alpha}$, $R^{\beta}$, and each of $R^{2-6}$ are independently hydrogen, deuterium, halogen, $C_1$-$C_5$ alkyl, $C_2$-$C_8$ alkenyl, $C_2$-$C_8$ alkynyl, $C_3$-$C_8$ cycloalkyl (independently or ring closed with the nitrogen, when $R^N$), $C_3$-$C_8$ cycloalkenyl (independently or ring closed with the nitrogen, when $R^N$), aryl, or heterocyclyl; including where $R^3$ and $R^4$ may be joined together to form a dioxole (as with MDMA), a furan, a tetrahydrofuran, a thiophene, a pyrrole, a pyridine, a pyrrolidine, an ethylene oxide, an ethylenimine, a trimethylene oxide, a pyran, a piperidine, an imidazole, a thiazole, a dioxane, a morpholine, a pyrimidine, or otherwise so as to create a benzene heterocycle; and any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, —OP(O)(OH)$_2$, —OC(O)H, —OSO$_2$OH, —OC(O)NH$_2$, and —SONH. In some embodiments, the phenethylamine comprises a quaternary ammonium cation wherein each of $R^{N1}$, $R^{N2}$, and an additional $R^{N3}$ are independently an alkyl group or an aryl group, and with all other substituents as above.

Other tryptamines and phenethylamines useful as additional active compounds for purposes of the invention and thus contemplated for inclusion therein will be as generally known in the art (see, e.g., Grob & Grigsby, Handbook of Medical Hallucinogens, 2021; Luethi & Liechti, Arch. Toxicol., 2020; 94, 1085-1133; Nichols, Pharmacological Reviews, 2016; 68(2), 264-355; Glennon, Pharmacology Biochemistry and Behavior, 1999; 64, 251-256).

Different embodiments of the invention include the following examples: Pharmaceutically acceptable complex derivatives of each drug in each group, including solvates, salts, esters, enantiomers, isomers (stereoisomers and/or constitutional, including ones based on substituting deuterium for hydrogen), derivatives or prodrugs of the disclosed compounds. Among derivatives of a compound are included its "physiologically functional derivatives," which refers to physiologically tolerated chemical derivatives of the compound having the same physiological function thereof, for example, by being convertible in the body thereto, and which on administration to a mammal such as a human is able to form (directly or indirectly) the compound or an active metabolite thereof (acting therefore, like a prodrug), or by otherwise having the same physiological function, despite one or more structural differences. According to the invention, examples of physiologically functional derivatives include esters, amides, carbamates, ureas, and heterocycles.

Another embodiment of the invention includes multiple variations in the pharmaceutical dosages of each drug in the combination as further outlined below. Another embodiment of the invention includes various forms of preparations including using solids, liquids, immediate or delayed or extended-release forms. Many types of variations are possible as known to those skilled in the art.

Another embodiment of the invention includes multiple routes of administration, which may differ in different patients according to their preference, comorbidities, side effect profile, pharmacokinetic and pharmacodynamic considerations, and other factors (IV, PO, transdermal, etc.). Another embodiment of the invention includes the presence of other substances with the active drugs, known to those skilled in the art, such as fillers, carriers, gels, skin patches, lozenges, or other modifications in the preparation to facilitate absorption through various routes (such as gastrointestinal, transdermal, etc.) and/or to extend the effect of the drugs, and/or to attain higher or more stable serum levels or to enhance the therapeutic effect of the active drugs in the combination.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing a therapeutically effective amount of the active ingredients, for example in the dosage amounts disclosed below. The term "unit dosage form" refers to a physically discrete unit suited as unitary dosages for the subject to be treated, each unit containing a predetermined quantity of active material calculated to produce the desired therapeutic effect(s), in association with a suitable pharmaceutical carrier, diluent, or excipient. Unit dosage forms are often used for ease of administration and uniformity of dosage. Unit dosage forms can contain a single or individual dose or unit, a sub-dose, or an appropriate fraction thereof (e.g., one half a "full" dose for a "booster" dose as described below), of the pharmaceutical composition administered.

Unit dosage forms include capsules, troches, cachets, lozenges, tablets, ampules and vials, which may include a composition in a freeze-dried or lyophilized state; a sterile liquid carrier, for example, can be added prior to administration or delivery in vivo. Unit dosage forms also include ampules and vials with liquid compositions disposed therein. Unit dosage forms further include compounds for transdermal administration, such as "patches" that contact the epidermis (including the mucosa) of a subject for an extended or brief period of time.

In some embodiments, the compositions of the invention are formulated in a pharmaceutically acceptable oral dosage form. Oral dosage forms include oral solid dosage forms and oral liquid dosage forms.

a. Oral Solid Dosage Forms

Oral solid dosage forms may include but are not limited to, lozenges, troches, tablets, capsules, caplets, powders, pellets, multiparticulates, beads, spheres, and/or any combinations thereof. Oral solid dosage forms may be formulated as immediate release, controlled release, sustained release, extended release, or modified release formulations. Accordingly, in some embodiments, the oral solid dosage forms of the invention may be in the form of a tablet (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including a fast-melt tablet. Additionally, pharmaceutical formulations of the invention may be administered as a single capsule or in multiple capsule dosage form. In some embodiments, the pharmaceutical formulation is administered in two, three, four, or more capsules or tablets.

Oral solid dosage forms may contain pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof. Oral solid dosage forms also can comprise one or more pharmaceutically acceptable additives such as a compatible carrier, complexing agent, ionic dispersion modulator, disintegrating agent, surfactant, lubricant, colorant, moistening agent, plasticizer, stabilizer, penetration enhancer, wetting agent, anti-foaming agent, alone or in combination, as well as supplementary active compound(s).

Supplementary active compounds include preservatives, antioxidants, antimicrobial agents including biocides and biostats such as antibacterial, antiviral and antifungal agents. Preservatives can be used to inhibit microbial growth or increase stability of the active ingredient thereby prolonging the shelf life of the formulation. Suitable preservatives are known in the art and include EDTA, EGTA, benzalkonium chloride or benzoic acid or benzoates, such as sodium benzoate. Antioxidants include vitamin A, vitamin C (ascorbic acid), vitamin E, tocopherols, other vitamins or provitamins, and compounds such as alpha lipoic acid.

Using standard coating procedures, a film coating may be provided around the active agents of the invention (see Remington, supra). In one embodiment, some or all of the active agents of the invention are coated. In another embodiment, some or all of the active agents of the invention are microencapsulated. In yet another embodiment, some or all of the active agents of the invention are amorphous material coated and/or microencapsulated with inert excipients. In still another embodiment, the active agents of the invention are not microencapsulated and are uncoated.

Suitable carriers for use in oral solid dosage forms include acacia, gelatin, colloidal silicon dioxide, calcium glycerophosphate, calcium lactate, maltodextrin, glycerin, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose (HPMC), hydroxypropylmethylcellulose acetate stearate (HPMCAS), sucrose, microcrystalline cellulose, lactose, and mannitol.

Suitable filling agents for use in oral solid dosage forms include lactose, calcium carbonate, calcium phosphate, dibasic calcium phosphate, calcium sulfate, microcrystalline cellulose, cellulose powder, dextrose, dextrates, dextrose, dextran, starches, pregelatinized starch, HPMC, HPMCAS, hydroxypropylmethylcellulose phthalate, sucrose, xylitol, lactitol, mannitol, sorbitol, sodium chloride, and PEG.

Suitable disintegrants for use in oral solid dosage forms include those disclosed below for oral liquid aqueous suspensions and dispersions.

Suitable binders impart cohesiveness to solid oral dosage form formulations. For powder-filled capsules, they aid in plug formation that can be filled into soft or hard shell capsules. For tablets, they ensure that the tablet remains intact after compression and help assure blend uniformity prior to a compression or fill step. Materials suitable for use as binders in the solid dosage forms described herein include celluloses, microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar (e.g., sucrose, glucose, dextrose, molasses, mannitol, sorbitol, xylitol, lactose), a natural or synthetic gum (e.g., acacia, tragacanth, ghatti gum, mucilage of isapol husks), starch, PVP, larch arabinogalactan, Veegum®, PEG, waxes, and sodium alginate.

In general, binder levels of 20-70% are used in powder-filled gelatin capsule formulations. Binder usage level in tablet formulations is a function of whether direct compression, wet granulation, roller compaction, or usage of other excipients such as fillers which itself can act as moderate binders are used. Formulators skilled in the art can determine binder level for formulations, but binder usage of up to 70% in tablet formulations is common.

Suitable lubricants or glidants for use in oral solid dosage forms include stearic acid, calcium hydroxide, talc, corn starch, sodium stearyl fumarate, alkali-metal and alkaline earth metal salts, stearic acid, sodium stearates, magnesium stearate, zinc stearate, waxes, Stearowet®, boric acid, sodium benzoate, sodium acetate, sodium chloride, leucine, PEG, methoxy-polyethylene glycol, propylene glycol, sodium oleate, glyceryl behenate, glyceryl palmitostearate, glyceryl benzoate, and magnesium or sodium lauryl sulfate.

Suitable diluents for use in oral solid dosage forms include sugars (including lactose, sucrose, and dextrose), polysaccharides (including dextrates and maltodextrin), polyols (including mannitol, xylitol, and sorbitol), and cyclodextrins. Non-water-soluble diluents are compounds typically used in the formulation of pharmaceuticals, such as calcium phosphate, calcium sulfate, starches, modified starches and microcrystalline cellulose, and micro cellulose (e.g., having a density of about 0.45 g/cm3, e.g., Avicel, powdered cellulose), and talc.

Suitable wetting agents for use in oral solid dosage forms include oleic acid, triethanolamine oleate, glyceryl monostearate, sorbitan monooleate, sorbitan monolaurate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, and vitamin E TPGS. Wetting agents include surfactants.

Suitable surfactants for use in the solid dosage forms described herein include docusate and its pharmaceutically acceptable salts, sodium lauryl sulfate, sorbitan monooleate, polyoxyethylene sorbitan monooleate, polysorbates, poloxamers, bile salts, glyceryl monostearate, copolymers of ethylene oxide and propylene oxide, e.g., Pluronic® (BASF), and the like.

Suitable suspending agents for use in oral solid dosage forms include polyvinylpyrrolidone, PEG (having a molecular weight of about 300 to about 6000, or about 3350 to about 4000, or about 7000 to about 18000), vinylpyrrolidone/vinyl acetate copolymer (S630), sodium alginate, gums (e.g., gum tragacanth and gum acacia, guar gum, xanthans, including xanthan gum), sugars, celluloses, polysorbate-80, polyethoxylated sorbitan monolaurate, polyethoxylated sorbitan monolaurate, and povidone.

Suitable antioxidants for use in oral solid dosage forms include butylated hydroxytoluene (BHT), butyl hydroxyanisole (BHA), sodium ascorbate, Vitamin E TPGS, ascorbic acid, sorbic acid, and tocopherol.

Immediate-release formulations may be prepared by combining a superdisintegrant such as croscarmellose sodium and different grades of microcrystalline cellulose in different ratios. To aid disintegration, sodium starch glycolate may be added.

In cases where different agents included in the fixed-dose combinations of the invention are incompatible, cross-contamination can be avoided by incorporation of the agents in different layers in the oral dosage form with the inclusion of barrier layer(s) between the different layers, wherein the barrier layer(s) comprise inert and non-functional material(s).

The above-listed additives should be taken as merely exemplary types of additives that can be included in solid dosage forms of the invention. The amounts of such additives can be readily determined by one skilled in the art, according to the particular properties desired.

Tablets of the invention can be prepared by methods well known in the art. Various methods for the preparation of the immediate release, modified release, controlled release, and extended-release dosage forms (e.g., as matrix tablets having one or more modified, controlled, or extended-release layers) and the vehicles therein are well known in the art. For example, a tablet may be made by compression or molding. Compressed tablets may be prepared by compressing, in a suitable machine, an active ingredient in a free-flowing form such as a powder or granules, optionally mixed with a binder, lubricant, inert diluent, preservative, surface-active or dispersing agent. Molded tablets may be produced by molding, in a suitable apparatus, a mixture of powdered compound moistened with an inert liquid diluent. The tablets may optionally be coated or scored and may be formulated so as to provide a slow or controlled release of the active ingredient therein. Generally recognized compendia of methods include: Remington (2020); Sheth et al. (1980), Compressed tablets, in Pharm. dosage forms, Vol. 1, Lieberman & Lachtman, eds., Dekker, NY.

In certain embodiments, solid dosage forms are prepared by mixing the active agents of the invention with one or more pharmaceutical excipients to form a "bulk blend" composition. The bulk blend composition is homogeneous, i.e., the active agents are dispersed evenly throughout so that the bulk blend may be readily subdivided into equally effective unit dosage forms, such as tablets, pills, and capsules. The individual unit dosages may also comprise film coatings, which disintegrate upon oral ingestion or upon contact with diluents. These formulations can be manufactured by conventional pharmaceutical techniques.

Conventional pharmaceutical techniques for preparation of solid dosage forms include the following methods, which may be used alone or in combination: (1) dry mixing, (2) direct compression, (3) milling, (4) dry or non-aqueous granulation, (5) wet granulation, or (6) fusion. See, e.g., Lachman et al., Theory and Practice of Industrial Pharmacy (1986). Other methods include spray drying, pan coating, melt granulation, granulation, fluidized bed spray drying or coating (e.g., Wurster coating), tangential coating, top spraying, tableting, and extruding.

Compressed tablets are solid dosage forms prepared by compacting the bulk blend. In various embodiments, compressed tablets which are designed to dissolve in the mouth will comprise one or more flavoring agents. In other embodiments, the compressed tablets will comprise a film surrounding the final compressed tablet. In some embodiments, the film coating can provide a delayed release of the active agents of the invention formulation. In other embodiments, the film coating aids in patient compliance (e.g., flavor or sweetener coatings).

A capsule may be prepared by placing the bulk blend inside of a capsule, such as a soft gelatin capsule, a standard gelatin capsule, or a non-gelatin capsule such as a capsule comprising HPMC. The bulk blend also may be placed in a sprinkle capsule, wherein the capsule may be swallowed whole or the capsule may be opened and the contents sprinkled on food prior to eating. In some embodiments, the therapeutic dose is split into multiple capsules. In some embodiments, the entire dose of the active agents of the invention formulation is delivered in a capsule form. In some embodiments the capsule is a size 000, size 00, or size 0 soft gelatin capsule. In other embodiments, the capsule is a size 1, size 2, size 3, or size 4 soft gelatin capsule. In other embodiments, the capsule is a hard gelatin capsule of equivalent size.

Capsules can be capped and packaged using a manual capsule filling machine as follows: (1) Open empty capsules and place lower halves (the 'bodies') in the holes of the bottom plate of the filling machine. Often machines have spacers that are inserted between the base plate and the plate with holes into which capsules are fitted. These need to be set so that the lower body of each capsule is flush with the top of the plate that holds the capsule bodies. (2) Place powder into the body of each capsule, ensuring an even distribution of powder using a spreader plate. (3) Take out the spacers and gently tap the plate with holes downwards so that each of the capsule bodies protrudes from the top of the plate. (4) Place the top half ('cap') of each capsule onto the lower half but do not press down firmly until all are in place. Once all the tops are in place, they can be pressed down gently (often a click is heard when they are all completely fitted). (5) If the machine has an upper plate into which caps can be loaded, fit these into the upper plate, and then flip the plate over and align it with the bottom plate, ensuring that all capsules halves are perfectly aligned. (6) Press the top plate firmly to secure the top of each capsule with the corresponding lower half. The above process also can be automated.

In certain embodiments, the formulations of the invention are fixed-dose pharmaceutical compositions of the invention and at least one other pharmacological agent. Fixed-dose combination formulations may contain therapeutically efficacious fixed-dose combinations of formulations of the active agents of the invention and other pharmacological agents in the form of a single-layer monolithic tablet or multi-layered monolithic tablet or in the form of a core tablet-in-tablet or multi-layered multi-disk tablet or beads inside a capsule or tablets inside a capsule.

Depending on the desired release profile, oral solid dosage forms may be prepared as immediate release formulations, or as modified release formulations, such as controlled release, extended release, sustained release, or delayed release.

In some embodiments, oral solid dosage forms are formulated as a delayed release dosage form by utilizing an enteric coating to affect release in the small intestine of the gastrointestinal tract. An enteric-coated oral dosage form may be a compressed or molded or extruded tablet/mold (coated or uncoated) containing granules, powder, pellets, beads or particles of the active ingredient and/or other composition components, which are themselves coated or uncoated. The enteric-coated oral dosage form may also be a capsule (coated or uncoated) containing pellets, beads or granules of the solid carrier or the composition, which are themselves coated or uncoated.

Enteric coatings may also be used to prepare other controlled release dosage forms including extended release and pulsatile release dosage forms. Pulsatile release dosage forms may be formulated using techniques known in the art, such as those described in U.S. Pat. Nos. 5,011,692, 5,017,381, 5,229,135, and 5,840,329. Other suitable dosage forms are described in U.S. Pat. Nos. 4,871,549, 5,260,068, 5,260,069, 5,508,040, 5,567,441 and 5,837,284.

In one embodiment, the controlled release dosage form is a pulsatile release solid oral dosage form comprising at least two groups of particles, each containing active agents of the invention described herein. The first group of particles provides a substantially immediate dose of the active agents of the invention upon ingestion by a subject. The first group of particles can be either uncoated or comprise a coating and/or sealant. The second group of particles comprises coated particles, which may comprise from about 2% to about 75%, preferably from about 2.5% to about 70%, or from about 40% to about 70%, by weight of the total dose of the active agents of the invention, in admixture with one or more binders. Using such means, a single unit dosage form can provide both a first and a second dosage amount in the single form (i.e., the first dosage amount in an immediate release form, and the second dosage amount in a delayed release form).

In another embodiment, gastroretentive sustained release tablets are formulated by using a combination of hydrophilic polymer (e.g., hydroxypropyl methylcellulose), together with swelling agents (e.g., crospovidone, sodium starch glycolate, and croscarmellose sodium), and an effervescent substance (e.g., sodium bicarbonate). Using known methods, gastroretentive tablets can be formulated so as to prolong the gastric emptying time and extend the mean residence time (MRT) in the stomach for optimal drug release and absorption (see, e.g., Arza et al. Formulation and evaluation of swellable and floating gastroretentive ciprofloxacin hydrochloride tablets, AAPS PharmSciTech., 10(1): 220-226 (2009)).

Coatings for providing a controlled, delayed, or extended release may be applied to the pharmaceutical compositions of the invention or to a core containing the compositions. The coating may comprise a pharmaceutically acceptable ingredient in an amount sufficient, e.g., to provide an extended release from e.g., about 1 hours to about 7 hours following ingestion before release of the compositions. Suitable coatings include one or more differentially degradable coatings including pH-sensitive coatings (enteric coatings), or non-enteric coatings having variable thickness to provide differential release of the active agents.

Many other types of modified release systems are known to those of ordinary skill in the art and are suitable for the formulations described herein. Examples of such delivery systems include both polymer- and nonpolymer-based systems, silastic systems, peptide-based systems, wax coatings, bioerodible dosage forms, and compressed tablets using conventional binders. (See, e.g., Liberman et al. Pharmaceutical Dosage Forms, 2 Ed., Vol. 1, pp. 209-214 (1990); Singh et al. Encyclopedia of Pharmaceutical Technology, 2nd Ed., pp. 751-753 (2002); U.S. Pat. Nos. 4,327,725; 4,624,848; 4,968,509; 5,461,140; 5,456,923; 5,516,527; 5,622,721; 5,686,105; 5,700,410; 5,977,175; 6,465,014; and 6,932,983.)

b. Oral Liquid Dosage Forms

Oral liquid dosage forms include tinctures, drops, emulsions, syrups, elixirs, suspensions, and solutions, and the like. These oral liquid dosage forms may be formulated with any pharmaceutically acceptable excipient known to those of skill in the art for the preparation of liquid dosage forms, and with solvents, diluents, carriers, excipients, and the like chosen as appropriate to the solubility and other properties of the active agents and other ingredients. Solvents may be, for example, water, glycerin, simple syrup, alcohol, medium chain triglycerides (MCT), and combinations thereof.

Liquid dosage forms for oral administration may be in the form of pharmaceutically acceptable emulsions, syrups, elixirs, suspensions, and solutions, which may contain an inactive diluent, such as water. Pharmaceutical formulations may be prepared as liquid suspensions or solutions using a sterile liquid, such as but not limited to, an oil, water, an alcohol, and combinations of these pharmaceutically suitable surfactants, suspending agents, emulsifying agents, may be added for oral or parenteral administration. Liquid formulations also may be prepared as single dose or multi-dose beverages. Suspensions may include oils. Such oils include peanut oil, sesame oil, cottonseed oil, corn oil, and olive oil. Suitable oils also include carrier oils such as MCT and long chain triglyceride (LCT) oils. Suspension preparation may also contain esters of fatty acids such as ethyl oleate, isopropyl myristate, fatty acid glycerides, and acetylated fatty acid glycerides. Suspension formulations may include alcohols, (such as ethanol, isopropyl alcohol, hexadecyl alcohol), glycerol, and propylene glycol. Ethers, such as poly(ethylene glycol), petroleum hydrocarbons such as mineral oil and petrolatum, and water may also be used in suspension formulations. Suspension can thus include an aqueous liquid or a non-aqueous liquid, an oil-in-water liquid emulsion, or a water-in-oil emulsion.

In some embodiments, formulations are provided comprising the compositions of the invention and at least one dispersing agent or suspending agent for oral administration to a subject. The formulation may be a powder and/or granules for suspension, and upon admixture with water, a substantially uniform suspension is obtained. The aqueous dispersion can comprise amorphous and non-amorphous particles consisting of multiple effective particle sizes such that a drug is absorbed in a controlled manner over time.

Dosage forms for oral administration can be aqueous suspensions selected from the group including pharmaceutically acceptable aqueous oral dispersions, emulsions, solutions, and syrups. See, e.g., Singh et al., Encyclopedia of Pharm. Tech., 2nd Ed., 754-757 (2002). In addition to the active agents of the invention, the liquid dosage forms may comprise additives, such as one or more (a) disintegrating agents, (b) dispersing agents, (c) wetting agents, (d) preservatives, (e) viscosity enhancing agents, (f) sweetening agents, or (g) flavoring agents.

Examples of disintegrating agents for use in the aqueous suspensions and dispersions include a starch, e.g., a natural starch such as corn starch or potato starch, a pregelatinized starch, or sodium starch glycolate; a cellulose such as a wood product, microcrystalline cellulose, methylcellulose, croscarmellose, or a cross-linked cellulose, such as cross-linked sodium carboxymethylcellulose, cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay; a gum such as agar, guar, locust bean, Karaya, pectin, or tragacanth; sodium starch glycolate; bentonite; a natural sponge; a surfactant; a resin such as a cation-exchange resin; citrus pulp; and sodium lauryl sulfate.

Examples of dispersing agents suitable for the aqueous suspensions and dispersions include hydrophilic polymers, electrolytes, Tween® 60 or 80, polyethylene glycol (PEG), polyvinylpyrrolidone (PVP), carbohydrate-based dispersing agents, noncrystalline cellulose, magnesium aluminum silicate, triethanolamine, polyvinyl alcohol (PVA), polyvinylpyrrolidone/vinyl acetate copolymer, poloxamers, and poloxamines.

Examples of wetting agents (including surfactants) suitable for the aqueous suspensions and dispersions include acetyl alcohol, glycerol monostearate, polyoxyethylene sorbitan fatty acid esters, PEG, oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, and phosphatidylcholine.

Examples of preservatives suitable for aqueous suspensions or dispersions include potassium sorbate, parabens (e.g., methylparaben and propylparaben) and their salts, benzoic acid and its salts, other esters of para hydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Examples of viscosity enhancing agents suitable for aqueous suspensions or dispersions include methyl cellulose, xanthan gum, carboxymethylcellulose, hydroxypropyl cellulose, hydroxypropylmethyl cellulose, Plasdone® S-630, carbomer, polyvinyl alcohol, alginates, acacia, chitosans, and combinations thereof. The concentration of the viscosity-enhancing agent will depend upon the agent selected and the viscosity desired.

In addition to the additives listed above, the liquid formulations of the invention can also comprise inert diluents commonly used in the art, such as water or other solvents, solubilizing agents, emulsifiers, flavoring agents and/or sweeteners. Co-solvents and adjuvants also may be added to a formulation. Non-limiting examples of co-solvents contain hydroxyl groups or other polar groups, for example, alcohols, glycols, glycerol, polyoxyethylene alcohols, and polyoxyethylene fatty acid esters. Adjuvants include surfactants such as soy lecithin and oleic acid, sorbitan esters such as sorbitan trioleate, and PVP.

c. Additional Dosage Forms

The pharmaceutical compositions of the invention also may be prepared as formulations suitable for intramuscular, subcutaneous, intraperitoneal, or intravenous injection, comprising physiologically acceptable sterile aqueous or non-aqueous solutions, dispersions, suspensions or emulsions, liposomes, and sterile powders for reconstitution into sterile injectable solutions or dispersions.

Examples of suitable aqueous and non-aqueous carriers, diluents, solvents, or vehicles include water, ethanol, polyols, suitable mixtures thereof, vegetable oils, and injectable organic esters such as ethyl oleate. Additionally, the compositions of the invention can be dissolved at concentrations of >1 mg/ml using water-soluble beta cyclodextrins (e.g., beta-sulfobutyl-cyclodextrin and 2-hydroxypropyl-betacyclodextrin. Proper fluidity can be maintained, for example, by the use of a coating such as a lecithin, by the maintenance of the required particle size in the case of dispersions, and by the use of surfactants.

Formulations suitable for subcutaneous injection also may contain additives such as preserving, wetting, emulsifying, and dispensing agents. Prevention of the growth of microorganisms can be ensured by various antibacterial and antifungal agents, such as parabens, benzoic acid, benzyl alcohol, chlorobutanol, phenol, and sorbic acid. Isotonic agents, such as sugars and sodium chloride may be used. Prolonged drug absorption of an injectable form can be brought about by use of agents delaying absorption, e.g., aluminum monostearate or gelatin.

The compositions of the invention may also be prepared as suspension formulations designed for extended-release via subcutaneous or intramuscular injection. Such formulations avoid first-pass metabolism, and lower dosages of the active agents will be necessary to maintain equivalent plasma levels when compared to oral formulations. In such formulations, the mean particle size of the active agents and the range of total particle sizes can be used to control the release of those agents by controlling the rate of dissolution in fat or muscle. The compositions also may be prepared for microinjection or injection cannula.

In still other embodiments, effervescent powders containing the compositions of the invention may be prepared. Effervescent salts are used to disperse medicines in water for oral administration. Effervescent salts also may be packaged as single dose or multi-dose drink mixes, alone or in combination with other ingredients, such as vitamins or electrolytes. Effervescent salts are granules or coarse powders containing a medicinal agent in a dry mixture, usually composed of sodium bicarbonate and sodium carbonate, citric acid, and/or tartaric acid. When salts of the invention are added to water, the acids and the base react to liberate carbon dioxide gas, thereby causing "effervescence." Any acid-base combination that results in the liberation of carbon dioxide can be used, as long as the ingredients are suitable for pharmaceutical use and result in a pH of about 6.0 or higher.

In yet other embodiments, the pharmaceutical compositions disclosed herein are prepared for administration as a nanostructured formulation such as a nanoemulsion, a nanocapsule, a nanoparticle conjugate, or a nano-encapsulated oral or nasal spray. Preparations of the compositions of the invention as certain nanostructured formulations may be done by reference to the general knowledge of the art. (See, e.g., Jaiswal et al., Nanoemulsion: an advanced mode of drug delivery system, Biotech 3(5):123-27 (2015).)

The prefix "nano" as used in the terms describing various embodiments of a nanostructured formulation denotes a size range in the nanometer ("nm") scale. Accordingly, sizes of such nanoparticle delivery vehicles include those in the about 1 to about 100 nm, about 100 to about 200 nm, about 200 to about 400 nm, about 400 to about 600 nm, about 600 to about 800 nm, and about 800 to about 1000 nm, as well as "microparticles" in the about 1000 to about 2000 nm (1-2 micrometer ("m") scale). Particles of certain sizes may be particularly advantageous depending on the method of administration (e.g., for oral liquid emulsion versus for transdermal or topical application). Regardless of method of administration, one will appreciate that smaller particles provide for increased surface area over larger particles such that a higher concentration of agent may be applied per volume of particles. A nanoparticle may be metal, lipid, polymer or other materials, or a combination of materials, and nanoparticles may be functionalized such that another moiety also may be attached thereto. Surface functionalization may involve the use of a moiety comprising an anchor group, a spacer and/or a functional group.

Lipid-based nanoparticles (LBNPs) such as liposomes, solid lipid nanoparticles (SLN), and nanostructured lipid carriers (NLC) can be used to transport both hydrophobic and hydrophilic molecules, and can be formulated to display very low or no toxicity, and increase the time of drug action by means of prolonged half-life and controlled release of active agents. Lipid nanosystems also can include chemical modifications to avoid immune system detection (e.g., gangliosides or PEG) or to improve solubility of active agents. In addition, such nanosystems can be prepared in formulations sensitive to pH so as to promote drug release in an acid environment.

The primary components of nanoparticles are phospholipids, which are organized in a bilayer structure due to their amphipathic properties. In presence of water, they form vesicles, improving the solubility and stability of the active agents once they are loaded into their structure. Besides phospholipids, other compounds can be added to the formulations, such as cholesterol, which decreases the fluidity of the nanoparticle and increases the permeability of hydrophobic drugs through the bilayer membrane, improving stability of nanoparticles in blood. Cholesterol-modified liposomes may present a multiple bilayer with sizes from 0.5-10 nm, as multilaminar vesicles (MLVs); a single bilayer with sizes above 100 nm, as large unilamellar vesicles (LUVs); and intermediate sizes (10-100 nm), as small unilamellar vesicles (SUVs).

In other embodiments, pharmaceutical compositions of the invention may be formulated into a topical dosage form. Topical dosage forms include transmucosal and transdermal formulations, such as aerosols, emulsions, sprays, ointments, salves, gels, pastes, lotions, liniments, oils, and creams. For such formulations, penetrants and carriers can be included in the pharmaceutical composition. Penetrants are known in the art, and include, for transmucosal administration, detergents, bile salts, and fusidic acid derivatives. For transdermal administration, carriers which may be used include Vaseline®, lanolin, PEG, alcohols, transdermal enhancers, and combinations thereof.

An exemplary topical delivery system is a transdermal delivery device ("patch") containing the active agents. Such transdermal patches may be used to provide continuous or discontinuous infusion of the disclosed compound in controlled amounts. Such patches may be constructed for continuous, gradual, pulsatile, or on demand delivery of pharmaceutical agents. A "patch" within the meaning of the invention may be simply a medicated adhesive patch, i.e., a patch impregnated with a disclosed composition for application onto the skin. Thus, a patch may be a single-layer or multi-layer drug-in-adhesive patch, wherein the one or more adhesive layers also contain the active agents.

A patch may also be a "matrix" (or "monolithic") patch, wherein the adhesive layer surrounds and overlays the drug layer (wherein a solution or suspension of the active agents is in a semisolid matrix). A "reservoir" patch may also be used, comprising a drug layer, typically as a solution or suspension of the active agents in a liquid compartment (i.e., the reservoir), separate from an adhesive layer. For example, the reservoir may be totally encapsulated in a shallow compartment molded from a drug-impermeable metallic plastic laminate, with a rate-controlling membrane made of vinyl acetate or a like polymer on one surface. A patch also may be part of a delivery system, for instance used with an electronic device communicatively coupled to the mobile device of a user, and coupled with a mobile application (e.g., to control the delivery rate from the reservoir, and optionally to provide information about delivery back to the application or user). Various transdermal patch technologies may be accordingly utilized.

One such transdermal patch technology as herein contemplated comprises a self-contained module including a built-in battery that produces a low-level electric current to heat the skin and deliver a prescribed dose of a disclosed composition, wherein a therapeutically effective amount of the composition crosses the skin and enters the underlying tissue, so as to produce a therapeutic effect. Such a transdermal delivery device may, for example, comprise an adhesive layer, a protective film, a drug-containing reservoir (for the pharmaceutical compositions of the invention), a heating coil, a battery, a hardware board, optionally all within a device holder, and optionally, functionally coupled to a device which is able to control drug delivery (e.g., a mobile device such as a smartphone) using a downloadable application. Such devices may, for instance, additionally shut off drug delivery automatically when a prescribed dose has been administered, or may shut off automatically upon reaching a certain temperature or defined time. Such transdermal devices may be reusable or disposable.

By way of non-limiting and merely suggestive example, the following formulations may be used in the methods of the invention, wherein "therapeutic compound" refers to one or more of the disclosed compounds.

Example 1: Formulation of Tablets

A tablet is prepared using the ingredients below:

| Ingredient | Quantity (mg/tablet) |
|---|---|
| Therapeutic Compound | 62.5 |
| Cellulose, microcrystalline | 170.0 |
| Colloidal silicon dioxide | 10.0 |
| Stearic acid | 7.5 |

The ingredients are blended and compressed to form tablets.

Example 2: Alternate Formulation of Tablets

Scorable tablets are prepared as follows:

| Ingredient | Quantity (mg/tablet) |
| --- | --- |
| Therapeutic Compound | 125.0 |
| Starch | 45.0 |
| Microcrystalline cellulose | 35.0 |
| PVP (as 10% solution in water) | 4.0 |
| Sodium carboxymethyl starch | 4.5 |
| Magnesium stearate | 0.5 |
| Talc | 1.0 |

The active agents, starch and cellulose are passed through a No. 20 mesh U.S. sieve and mixed thoroughly. The solution of polyvinylpyrrolidone (PVP) is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets. Tablets are scored to provide the ability to create equal half doses.

Example 3: Formulation of Capsules

Capsules are made as follows:

| Ingredient | Quantity (mg/capsule) |
| --- | --- |
| Therapeutic Compound | 80.0 |
| Starch | 119.0 |
| Magnesium stearate | 1.0 |

The active agents, cellulose, starch, and magnesium stearate are blended, passed through a No. 20 mesh U.S. sieve, and filled into hard or soft gelatin capsules.

Example 4: Formulation of Suspension

Suspensions are made as follows:

| Ingredient | Amount |
| --- | --- |
| Therapeutic Compound | 80.0 mg |
| Xanthan gum | 4.0 mg |
| Sodium carboxymethyl cellulose (11%) | 50.0 mg |
| Microcrystalline cellulose (89%) | 50.0 mg |
| Sucrose | 1.75 g |
| Sodium benzoate | 10.0 mg |
| Flavor and color (optional) | q.v. |
| Purified water | To 5.0 ml |

The active agents, sucrose and xanthan gum are blended, passed through a No. 10 mesh U.S. sieve, and then mixed with a previously made solution of the microcrystalline cellulose and sodium carboxymethyl cellulose in water. The sodium benzoate and optional flavor and color are diluted with some of the water and added with stirring. Sufficient water is then added to produce the required volume.

Example 5: Formulation of Intravenous Solution

An intravenous formulation may be prepared as follows:

| Ingredient | Amount |
| --- | --- |
| Therapeutic Compound | 500 mg |
| Isotonic saline | 1000 mL |

Active agents are dissolved in appropriate solvent as will be understood by those of ordinary skill; isotonic saline is used in this Example, but it will be appreciated that other solvents may be used, and additional active or inactive ingredients such as preservatives may be added, as otherwise described above, and within the general knowledge of the art. It will be understood that the amount of therapeutic compound can be adjusted accordingly to reach desired mg/mL.

Example 6: Formulations of Injectable Solution

Injectable formulations may be prepared as follows:

| Ingredient | Amount |
| --- | --- |
| Therapeutic Compound | 125 mg |
| Isotonic saline | 5 mL |

Active agents are dissolved in appropriate solvent as will be understood by those of ordinary skill; isotonic saline is used in this Example, but it will be appreciated that other solvents may be used, and additional active or inactive ingredients such as preservatives may be added, as otherwise described above, and within the general knowledge of the art.

Example 7: Formulation of Topical for Transdermal Administration

A topical formulation may be prepared as follows:

| Ingredient | Amount (g) |
| --- | --- |
| Therapeutic Compound | 1.0 |
| Emulsifying Wax | 30.0 |
| Liquid Paraffin | 20.0 |
| White Soft Paraffin | To 100 |

The white soft paraffin is heated until molten. The liquid paraffin and emulsifying wax are incorporated and stirred until dissolved. The active ingredient is added and stirring is continued until dispersed. The mixture is then cooled until solid.

Example 8: Formulation of Cut Matrix Sublingual or Buccal Tablets

Sublingual or buccal tablets are made as a single matrix and then cut to size:

| Ingredient | Amount (mg/tablet) |
| --- | --- |
| Therapeutic Compound | 100.0 |
| Glycerol | 210.5 |

-continued

| Ingredient | Amount (mg/tablet) |
|---|---|
| Water | 143.0 |
| Sodium Citrate | 4.5 |
| Polyvinyl Alcohol | 26.5 |
| Polyvinylpyrrolidone | 15.5 |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

Example 9: Formulation of Individually Formed Sublingual or Buccal Lozenges

Sublingual or buccal lozenges are made from individual forms or molds:

| Ingredient | Amount (mg/each lozenge) |
|---|---|
| Therapeutic Compound | 50.0 |
| Silica gel powder | 350.0 |
| Citric acid powder | 400.0 |
| Acacia powder | 600.0 |
| Flavor (optional) | 100.0 |
| Polyethylene glycol | 1,000 |

The inactive ingredients are admixed by continuous stirring and maintaining the temperature at about 90° C. When the PEG has melted and the other ingredients have gone into solution, the solution is cooled to about 50-55° C. and the active agents are slowly admixed. The homogenous mixture is poured into separate molds and allowed to cool. Reference may also be made to U.S. Pat. No. 10,034,832 and the Examples therein, the entirety of which is incorporated herein.

It should be readily appreciated that the above formulation examples are illustrative only. An "active agent" or "active ingredient" in the above examples will be understood to include the one or more compound(s) of the invention, e.g., any of any of Formula (I), Formula (II), Formula (III), and Formula (IV), that comprise the formulation. Accordingly, any of the compounds may be substituted with the same compound in a different dosage amount. It will be understood that reference to particular compounds is merely illustrative, and both active and inactive compounds in any Example may be substituted by other disclosed compounds.

Moreover, for any of the disclosed compounds, substitution of the compound by its ion, free base, salt form, polymorph, hydrate or solvate form, co-crystal, or an isomer or enantiomerically enriched mixture, shall be understood to provide merely an alternative embodiment still within the scope of the invention (with modifications to the formulation and dosage amounts made according to the teachings herein and ordinary skill, if necessary or desired). Further, compositions within the scope of the invention should be understood to be open-ended and may include additional active or inactive compounds and ingredients.

The type of formulation employed for the administration of the compounds employed in the methods of the invention generally may be dictated by the compound(s) employed, the type of pharmacokinetic profile desired from the route of administration and the compound(s), and the state of the patient. It will be readily appreciated that any of the above embodiments and classes of embodiments can be combined to form additional embodiments.

D. Methods of Use

In some aspects, provided herein are methods of using the disclosed compounds. In some embodiments, disclosed compounds are used as research tools. In some embodiments, disclosed compounds are used to modulate neurotransmission. In some embodiments, disclosed compounds are used to treat a condition, such as a disease or a disorder. In some embodiments, disclosed compounds are used in the manufacture of a medicament for the therapeutic and/or the prophylactic treatment of a condition, such as a disease or a disorder. In some embodiments, disclosed compounds are administered to a subject having a condition, such as a disease or a disorder. In some embodiments, the condition is a mental health disorder. In some embodiments, the condition is a neurodegenerative disorder. In some embodiments, disclosed compounds are administered to a subject that is healthy.

In some embodiments, the disclosed compounds are administered to a subject, e.g., a subject having a condition, such as a disease or a disorder. As used herein, the terms "subject," "user," "patient," and "individual" are used interchangeably, and refer to any mammal although preferably a human. Such terms will be understood to include one who has an indication for which a compound, composition, or method described herein may be efficacious, or who otherwise may benefit by the invention. In general, all of the compounds, compositions, and methods of the invention will be appreciated to work for all individuals, although individual variation is to be expected, and will be understood. The disclosed methods of treatment also can be modified to treat multiple patients at once, including couples or families. Hence, these terms will be understood to also mean two or more individuals.

a. Research Tools

In some embodiments, disclosed compounds are used as research tools, such as tools for scientific research. In some embodiments, the disclosed compounds are used as analytical reagents. In some embodiments, the disclosed compounds are used for spectroscopy applications. In some embodiments, the disclosed compounds are used for quality control applications. In some embodiments, the disclosed compounds are used for forensic applications.

In some embodiments, the disclosed compounds are useful as analytical reagents. One exemplary use is for determining the concentration of the naturally occurring compound in solution, i.e., the compound wherein all hydrogen and all carbon atoms are present at their natural isotopic abundance percentages. It is recognized that some variation of natural isotopic abundance occurs depending upon the origin of chemical materials. The concentration of naturally abundant stable hydrogen and carbon isotopes, notwithstanding this variation, is small and immaterial with respect to the degree of stable isotopic substitution of compounds of this invention (see, e.g., Gannes 1998, Wada 1994). Use of deuterated MDMA (MDMA-d5) and MDA (MDA-d5) as analytical standards is described in, e.g., Lin et al., J Anal Toxicol. 2004; 28(8):650-4. Differences in binding affinities of MDMA and analogs thereof, in both deuterated and undeuterated forms, is described by, e.g., Romberg et al., J Anal Toxicol. 2011; 35(1):15-22.

In some embodiments, the disclosed compounds are useful in spectroscopy applications. Use of deuterated MDMA and analogs thereof, such as MDMA-d5 and MDA-d5, is described in e.g, GC/MS (Belal et al., see, e.g., J Chromatogr Sci. 2009; 47(5):359-64), MALDI (see, Poetzsch et al., e.g., Drug Test Anal. 2016; 8(2):235-40), and LC-MS/MS, among other spectroscopic applications (see, e.g., Concheiro et al., Forensic Sci Int. 2007 Aug. 24; 171(1):44-51). In another example, disclosed compounds are used in isotope ratio mass spectrometry (IRMS) applications. In some embodiments, the disclosed compounds are used for drug quality control and product authentication. Exemplary applications of quality control and product authentication include differentiating batches of drug and identifying counterfeits.

In some embodiments, disclosed compounds are used to compare the behavioral effects of an undeuterated corresponding compound. In one example, Berquist et al. found that d2-MDMA is behaviorally active and produces locomotor effects that are similar to MDMA (Psychopharmacology (Berl). 2020; 237(2):431-442). Berquist et al. also found that deuterium substitution of hydrogen at the methylenedioxy ring moiety (d2-MDMA) does not impact MDMA's interoceptive effects and has reduced potential for producing hyperthermic effects (Berquist et al., Drug Alcohol Depend. 2020; 208:107850.

In some embodiments, disclosed compounds are used for pharmacokinetic (PK) studies. Pharmacokinetics refers to the absorption, distribution, metabolism, and excretion of a compound in an organism. In one representative example, disclosed compounds may be used to determine drug partitioning, distribution within an organism, and drug dosing, for instance by providing quantitative information about the half-life and rate of metabolism of a compound.

In some embodiments, disclosed compounds are used for forensic applications. For example, the disclosed compounds may be used to elucidate different production batches and different synthetic precursors. The undeuterated counterparts of disclosed compounds may be federally controlled substances. Accordingly, deuteration will also allow healthcare providers or law enforcement to distinguish (e.g., by analytical methods) use of a regulated (i.e., deuterated) drug product from an illegal (i.e., non-substituted) one, or to quantify levels of a compound in urine, serum, or plasma by LC/MS or GC/MS for clinical toxicology or drug testing. In one example, quantification of MDMA, MDEA, and MDA in confiscated tablets, using deuterated standards, is described by Teng et al., Forensic Sci Int. 2006; 161(2-3): 202-8. Postmortem and antemortem analysis of MDMA and MDA heart blood, gastric content, urine, and bile specimens, using MDMA-d5 and MDA-d5, has also been described (Liu et al., J Anal Toxicol. 2006; 30(8):545-50).

b. Modulating Neurotransmission

In some embodiments, the disclosed compounds modulate neurotransmission. In some embodiments, modulating neurotransmission comprises regulating levels of monoamines in, for example, the CNS and peripheral tissues. In some embodiments, modulating neurotransmission comprises increasing levels of monoamines in, for example, the CNS and peripheral tissues of a subject to whom a therapeutic compound has been administered. In some embodiments, modulating neurotransmission comprises decreasing levels of monoamines in, for example, the CNS and peripheral tissues of a subject to whom a therapeutic compound has been administered. In some embodiments, modulating neurotransmission by administering a disclosed compound to a subject treats a disease or disorder in the subject.

In some embodiments, the disclosed compounds modulate neurotransmission, such as neurotransmission in a subject. In some methods herein, the compositions of the invention, when administered in a pharmacologically effective amount, thus affect monoaminergic neurotransmission, including serotonergic, dopaminergic, and noradrenergic neurotransmission. Accordingly, in some embodiments, the compositions of the invention, when administered in a pharmacologically effective amount, are used to treat a medical condition linked to dysregulation or inadequate functioning of neurotransmission, and in specific embodiments, are used to treat a medical condition linked to monoaminergic neurotransmission.

In some embodiments, the compositions of the invention, when administered in a pharmacologically effective amount, act on or modulate one or more membrane transporters, including any one or more of a serotonin membrane transporter, a dopamine membrane transporter, a norepinephrine membrane transporter, and a vesicular monoamine transporter.

In some embodiments, disclosed compounds are relatively weak releasers of serotonin compared to the corresponding undeuterated compound. In the representative example of known compound MDMA-d3, the undeuterated corresponding compound is MDMA. In some embodiments, serotonin release of disclosed compounds is reduced by at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, or 200% relative to the corresponding undeuterated compound.

In some embodiments, disclosed compounds are relatively weak releasers of serotonin compared to MDMA and/or MDMA-d3. In some embodiments, serotonin release of disclosed compounds is reduced by at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, or 200% relative to MDMA. In some embodiments, serotonin release of disclosed compounds is reduced by at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, or 200% relative to MDMA-d3.

In some embodiments, serotonin release of disclosed compounds is reduced by at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, or 200% relative to bk-MDMA (methylone). In some embodiments, serotonin release of disclosed compounds is reduced by at least 5%, 10%, 15%, 20%, 25%, 30%, 35%, 40%, 45%, 50%, 55%, 60%, 65%, 70%, 75%, 80%, 85%, 90%, 95%, 100%, 125%, 150%, or 200% relative to deuterated bk-MDMA.

By initiating the release of large amounts of serotonin, MDMA can cause the brain to become significantly depleted of this neurotransmitter, contributing to negative psychological effects that people may experience for several days after taking MDMA. Depletion of serotonin can, e.g., create the experience of depression in a patient, with special concerns for patients who are already diagnosed with depression or anxiety and impair the patient's memory of the therapy session. Among others, these negative effects and experiences may reduce a patient's future psychiatric medication adherence. Such effects are described in, e.g., Bolla et al., Neurology. 1998; 51(6):1532-1537, Kish et al., Neurology. 2000; 55(2):294-296, and Mithoefer et al., Psychopharmacol 236:2735-2745. This is especially problematic in subject populations that already show reduced treatment adherence, such as subjects having or diagnosed with a mental health disorder. See, e.g., Salas et al., J Affect Disord 260, 119-123, Hung et al., Curr. Opin. Psychiatry 27, 344-349, Lockwood et al., Ann. Pharmacother. 43, 1227-1232, and Maddox et al., Journal of Psychopharmacology, 8, 48-53.

In some embodiments, the compositions of the invention, when administered in a pharmacologically effective amount, act on or modulate one or more receptors. In some embodiments, the compositions are agonists or partial agonists of a monoamine receptor, including a serotonin receptor, a dopamine receptor, or a norepinephrine receptor. In some embodiments, administration of a deuterium-substituted disclosed composition according to the methods herein will have an improved pharmacological profile, such as a relative increase in agonism of serotonin receptors compared to dopamine and/or norepinephrine receptors, compared to a corresponding non-substituted composition, which may be an increase of 5% or more, 10% or more, 25% or more, or 50% or more, and including amounts in between. Measurements of agonism of a receptor will be as understood by those in the art or by reference to the general knowledge in the art.

In some embodiments, the compositions of the invention, when administered in a pharmacologically effective amount, inhibit the reuptake of one or more neurotransmitters.

In some embodiments, the compositions of the invention, when administered in a pharmacologically effective amount, inhibit a monoamine oxidase enzyme, including MAO-A and MAO-B.

In some embodiments, the compositions of the invention, when administered in a pharmacologically effective amount, increase the extracellular concentration of one or more neurotransmitters, including the amount of extracellular serotonin, dopamine, or norepinephrine. In some embodiments, an improved pharmacological profile of a deuterium-substituted disclosed composition will be a relative increase in extracellular concentration of serotonin compared to dopamine and/or norepinephrine, compared to a corresponding non-substituted composition, which may be an increase of 5% or more, 10% or more, 25% or more, or 50% or more, and including amounts in between. Measurements of extracellular concentration of a neurotransmitter will be as understood by those in the art or by reference to the general knowledge in the art.

Phenthylamine empathogens are a potent releaser and/or reuptake inhibitor of presynaptic serotonin (5-HT), dopamine (DA), and norepinephrine (NE), actions which result from their interaction with the membrane transporters involved in neurotransmitter reuptake and vesicular storage systems (e.g., SERT, DAT, NET, VMAT) (de la Torre et al., Therapeutic Drug Monitoring, 2004; 26(2), 137-144). Phenthylamine empathogens also have direct effects on a variety of receptors, including (among numerous more), $5-HT_{1A}$, $5-HT_{1D}$, $5-HT_{1E}$, $5-HT_{2A}$, $5-HT_{5A}$, $5-HT_6$, $5-HT_7$, D1, D2, D3, D4, D5, NMDA, and Imidazolinel (Vegting, Psychopharmacology, 2016; 233(19-20), 3473-3501; Ray, PloS one, 2010; 5(2), e9019). Phenthylamine empathogens have also been shown to be releasers of serotonin by a $Ca^{2+}$-independent mechanism. They additionally inhibit the 5-HT reuptake system, and inhibits monoamine oxidase (MAO), both of which can result in an in-creased amount of extracellular 5-HT. (Leonardi & Azmitia, Neuropsychopharmacology, 1994; 10(4), 231-238). Other empathogens have shown similar pharmacological profiles (see, e.g., Simmler & Liechti, Handbook of Experimental Pharmacology, 2018; 252, 143-164).

Detecting a change in monoamine levels in a subject, such as an increase or a decrease, can be achieved according to methods known to one of skill, for example, brain microdialysis (Chefer et al., Curr Protoc Neurosci. 2009; Chapter: Unit 7.1; Darvesh et al., Expert Opin Drug Discov. 2011; 6(2): 109-127) and brain imaging, for example, positron emission tomography (PET) and single photon emission computed tomography (SPECT) (see e.g., Wong & Gjedde, Encyclopedia of Neuroscience, 2009; 939-952 and Takano, Front Psychiatry., 2018; 9:228).

c. Treatment

In some embodiments, the disclosed compounds are used to treat a condition, such as a disease or a disorder. In some embodiments, described herein are disclosed compounds for use in treating a condition, such as a disease or a disorder. In some embodiments, the disclosed compounds are used in the manufacture of a medicament to treat a condition, such as a disease or disorder. In some embodiments, described are methods of administering disclosed compounds to a subject having a condition, such as a disease or disorder, thereby treating said condition.

In some embodiments, pharmaceutical compositions comprising the disclosed compounds are administered to a subject by one or more routes of administration, including, e.g., oral, mucosal, rectal, subcutaneous, intravenous, intramuscular, intranasal, inhaled, and transdermal routes. When administered through one or more of such routes, the compound(s) of the invention and the disclosed compositions and formulations comprising them are useful in methods for treating a patient in need of such treatment.

i. Mental Health Disorders

In some embodiments, the disclosed compounds are used to treat mental health disorders. In some embodiments, disclosed compounds are administered to a subject having a mental health disorder, thereby treating said mental health disorder. In some methods herein, the compositions of the invention, when administered in a pharmacologically effective amount, provide beneficial therapeutic effects for the treatment of mental health disorders.

"Mental health disorder" refers to a disease condition in a mammal, and preferably in a human, that generally involves negative changes in emotion, mood, thinking, and/or behavior. In some embodiments, disclosed compounds are used to treat mental health disorders, including any of depression, major depressive disorder, treatment-resistant depression, dysthymia, anxiety and phobia disorders (including generalized anxiety, social anxiety, panic, post-traumatic stress and adjustment disorders), feeding and eating disorders (including binge eating, bulimia, and anorexia nervosa), other binge behaviors, body dysmorphic syndromes, a substance use disorder, such as any of alcohol use disorder, cannabis use disorder, hallucinogen use disorder, inhalant use disorder, opioid use disorder, nicotine dependence and tobacco use disorder, sedative, hypnotic, and anxiolytic use disorder, and stimulant use disorder, drug abuse or dependence disorders, disruptive behavior disorders, impulse control disorders, gaming disorders, gambling disorders, memory loss, dementia of aging, attention deficit hyperactivity disorder, personality disorders (including antisocial, avoidant, borderline, histrionic, narcissistic, obsessive compulsive, paranoid, schizoid and schizotypal personality disorders), attachment disorders, autism, and dissociative disorders, as well as such other mental health disorders as will be readily apparent to those of skill.

For instance, other classifications and examples of mental health disorders include those disclosed in Merck Manual of Diagnosis and Therapy, 20th Ed. (2018), i.e., anxiety and stressor-related disorders, dissociative disorders, eating disorders, mood disorders, obsessive-compulsive and related disorders, personality disorders, schizophrenia and related disorders, sexuality, gender dysphoria, and paraphilias, somatic symptom and related disorders, suicidal behavior and self-injury, and substance-related disorders, which includes substance-induced and substance use disorders.

A mental health disorder, where otherwise undefined, will be understood to refer to the disorder as defined in the Diagnostic and Statistical Manual of Mental Disorders, 5th Edition (DSM-5). Although such terms generally shall refer to the criteria in the DSM-5, or a patient with a diagnosis based thereon, it will be appreciated that the compositions and methods of the invention are equally applicable to patients having the equivalent underlying disorder, whether that disorder is diagnosed based on the criteria in DSM-5 or in DSM-IV, whether the diagnosis is based on other clinically acceptable criteria, or whether the patient has not yet had a formal clinical diagnosis.

In some embodiments, disclosed compounds are used to treat "trauma- and stressor-related disorders," which include acute stress disorder, adjustment disorders, and post-traumatic stress disorder (Merck Manual, 20th Ed.), as well as reactive attachment disorder, disinhibited social engagement disorder, and others (Am. Psych. Assoc., Diagnostic and Statistical Manual of Mental Disorders (DSM-5) (2013)), including such stressor-related disorders as brief psychotic disorder with marked stressor(s), and other disorders associated with psychological trauma. In certain embodiments, the mental health disorder of the invention is specifically PTSD.

While the neurophysiology underlying mental health disorders may be distinct, an aspect in common of many is the presence of a deleterious, repetitive, and often "rigid" thought process that negatively impacts an individual's ability to function. For someone with PTSD, for instance, symptoms involve re-experiencing trauma and the feelings associated with it; for depression it can take the form of a recurrent internal editor that attaches negative connotations to normal life events; and for addiction it is the preoccupation with acquiring and using the substance of choice. Thus, in many embodiments, the method of treating a mental health disorder involves the treatment of a disorder related to rigid modes of thinking. In different embodiments, the disorder related to rigid modes of thinking can be anxiety, depression, addiction, an eating disorder, obsessive compulsive disorder, or PTSD.

In some embodiments, the pharmaceutical compositions and formulations of the invention are used to reduce the symptoms of a mental health disorder. The symptoms of the mental health disorder to be treated shall be able to be determined by one of skill in the art, by reference to the general understanding of the art regarding that disorder.

Symptoms of PTSD, for example, include transient waking dissociative states in which events are relived as if happening ("flashbacks"), nightmares, distressing and intense memories, other intrusive negative memories, distress or physical reactions after being exposed to triggers, blaming self or others for the trauma, decreased interest in things that were once enjoyable and other feelings of emotional numbness, negative feelings about self and the world, inability to remember the trauma clearly, difficulty feeling positive, feelings of isolation, negative affect, difficulty feeling positive, other negative alterations in cognition and mood, avoidance, aggression or irritability, hypervigilance and hyper-awareness, difficulty concentrating, difficulty sleeping, heightened startle response, engaging in self-destructive, or risky behavior, difficulty sleeping or staying asleep, and suicidal ideation. Accordingly, methods of the invention that reduce the symptoms of PTSD would be understood to reduce any such symptoms.

As would be apparent to one of skill, symptoms for each mental health condition will be different, however, through medical monitoring (such as monitoring of objective measurements, as described herein), patient reporting (such as, but not limited to through journaling), completion of questionnaires, etc., one will be able to objectively determine if a symptom has reduced in its frequency and/or magnitude.

In some embodiments, measures of therapeutic efficacy include reports by a subject or an observer. In some embodiments, measures of therapeutic efficacy include responses to a questionnaire. Non-limiting representative examples of applicable measures of symptom improvement include The Generalized Anxiety Disorder Scale-7 (GAD-7), the Montgomery-Asberg Depression Rating Scale (MADRS), Global Assessment of Functioning (GAF) Scale, Clinical Global Impression (CGI), The Substance Abuse Questionnaire (SAQ), and related subject- or observer-reported measures.

ii. Neurodegenerative Conditions

In some embodiments, disclosed compounds are used to treat a neurological disorder. In some embodiments, disclosed compounds are administered to a subject having a neurological disorder, thereby treating said neurological disorder. In some embodiments, the neurological disorder is any of multiple sclerosis, Parkinson's disease, dementia, Alzheimer's disease, Huntington's disease, amyotrophic lateral sclerosis (ALS), and motor neuron disease.

Neurodegeneration may be assessed, e.g., by measuring markers of neuronal loss, such as cerebrospinal fluid markers, e.g., visinin-like protein 1 (VILIP-1), tau, and p-tau181 (Tarawneh et al., Neurol. 2015; 72(6): 656-665). In one specific example, Alzheimer's disease may be assessed using any of biomarket PET scans, blood tests, CSF tests, and neuropsychological assessments, e.g., to assess the presence of amyloid plaque and aggregated tau. Cognitive decline may also be used as a measure of neurodegeneration. Methods for assessing cognitive decline, e.g., comprehensive neuropsychological testing, are known to one of skill in the art. Exemplary cognitive evaluations include Mini-Mental State Examination (MMSE) and Montreal Cognitive Assessment (MoCA). See, e.g., Toh et al., Transl Neurodegener. 2014; 3:15. Cognitive decline and the progression of disease state may also be assessed using a condition-specific measure, e.g., the Unified Huntington's Disease Rating Scale (UHDRS).

Neurodegenerative conditions, such as diseases or disorders include, e.g., dementia, Alzheimer's disease, Huntington's disease, multiple sclerosis, and Parkinson's disease. A feature of neurodegenerative conditions is neuronal cell death, which, among other aspects, has been implicated in the promotion of inflammation. See, e.g., Chan et al., Annu Rev Immunol. 2015; 33: 79-106 and Chi et al., Int J Mol Sci. 2018; 19(10):3082. Neurodegenerative diseases can be classified according to primary clinical features, e.g., dementia, parkinsonism, or motor neuron disease, anatomic distribution of neurodegeneration, e.g., frontotemporal degenerations, extrapyramidal disorders, or spinocerebellar degenerations, or principal molecular abnormality (Dugger & Dickson, Cold Spring Harb Perspect Biol. 2017; 9(7): a028035.

iii. Empathogenic Effects

In some embodiments, features of the disclosed compounds provide improved empathogenic effects. In some embodiments, disclosed compounds provide improved empathogenic effects relative to a comparator. In some embodiments, improved empathogenic effects comprise enhanced feelings of compassion for self or others, heart opening, or a spiritual or mystical experience. In some embodiments, improved empathogenic effects comprise a higher score on the Oceanic Boundlessness rating scale or the Mystical Experience Questionnaire (MEQ). In some embodiments, improved empathogenic effects comprise a higher score on any one of the criteria of the Oceanic Boundlessness rating scale, such as insightfulness, blissful state, experience of unity, and spiritual experience. In some embodiments, the comparator is the corresponding undeuterated compound. In some embodiments, the comparator is MDMA. In some embodiments, the comparator is MDMA-d3.

In some embodiments, improved empathogenic effects comprise reduced feelings of anxiety. In some embodiments, improved empathogenic effects comprise a lower score on the Dread of Ego Dissolution Inventory. In some embodiments, improved empathogenic effects comprise a lower score on any one of the criteria of the Dread of Ego Dissolution Inventory. In some embodiments, the comparator is the corresponding undeuterated compound. In some embodiments, the comparator is MDMA. In some embodiments, the comparator is MDMA-d3.

Determining the magnitude of an empathogen experience may include use of questionnaires, natural language processing (NLP), and other tools available to one of skill. Exemplary questionnaires for determining the magnitude of psychedelic effects or a psychedelic experience include the Altered States of Consciousness (ASC), Mystical Experience Questionnaire (MEQ), Oceanic Boundlessness (OBN), and Dread of Ego Dissolution (DED). The quality or magnitude of mystical and spiritual experiences has been positively correlated with favorable treatment outcomes. See, e.g., McCulloch et al., Front Pharmacol. 2022; 13: 841648; Roseman et al., Front Pharmacol., 2018; 8:974). Enhanced efficacy and duration of action of disclosed compounds may contribute to improved empathogenic effects.

As used herein, "an effective amount" or "a pharmacologically effective amount" refers to an amount of an active agent that is non-toxic and sufficient to provide the desired therapeutic effect with performance at a reasonable benefit/risk ratio attending any medical treatment. The effective amount will vary depending upon the subject and the disease condition being treated or health benefit sought, the weight and age of the subject, the severity of the disease condition or degree of health benefit sought, the manner of administration, and the like, all of which can readily be determined by one of ordinary skill in the art.

As used herein, "therapeutic effect" or "therapeutic efficacy" means the responses(s) in a mammal, and preferably a human, after treatment that are judged to be desirable and beneficial. Hence, depending on the disorder to be treated, or improvement in mental health or functioning sought, and depending on the particular constituent(s) in the formulations of the invention under consideration, those responses shall differ, but would be readily understood by those of skill.

Measures of therapeutic effect includes any outcome measure, endpoint, effect measure, or measure of effect within clinical or medical practice or research which is used to assess the effect, both positive and negative, of an intervention or treatment, whether patient-reported (e.g., questionnaires), based on other patient data (e.g., patient monitoring), gathered through laboratory tests such as blood work, urine samples, etc., through medical examination by a doctor or other medical professional, or by digital tools or means, e.g., electronic tools such as online tools, smartphones, wireless devices, biosensors, or health apps.

In some embodiments, measures of therapeutic effect will include an assessment. "Assessment" refers to any means or method used with a patient, whether before, during, after, or unrelated in time to a specific treatment protocol, to measure, estimate, or evaluate a nature, ability, symptom, disorder, or other characteristic of the patient, whether qualitatively or quantitatively, and whether performed by the therapist or other clinician (e.g., an interview), by the patient his or herself (e.g., a self-reported questionnaire), by a third-party or by a computer, including a medical device (e.g., as such as defined by the FDA or other regulatory body) or other device (e.g., a medical sensor or biosensor, a watch or fitness tracker, or a "wearable"), and whether graded by a human decision-maker or an artificial intelligence, machine learning, or computer algorithm. Non-limiting examples of assessments include those in Table 1 below.

TABLE 1

Exemplary Patient Assessments

1 The Mini International Neuropsychiatric Interview 5 (MINI 5) (Sheehan et al. 1998) to screen for comorbid psychiatric disorders.
2 The Columbia Suicide Severity Rating Scale (C-SSRS) (Mundt, JC et al. 2013), to screen for acute and recent suicide and self-harm thoughts and behaviors, taking approximately five minutes to complete.
3 The Patient Health Questionnaire (PHQ-9) (Kroenke et al. 2001). A brief self-administered screening questionnaire for depressive symptoms.
4 Generalized Anxiety Disorder 7 (GAD-7) (Spitzer et al. 2006) is a self-reported questionnaire for screening and severity measuring of generalized anxiety disorder.
5 Pittsburgh Sleep Quality Index (PSQI) (Buysse 1989) is used to assess the level of sleep disturbance.
6 Interpersonal reactivity Index (IRI) (Davis 1980) comprises 28 items answered on a 5 point scale. This scale measures different aspects of empathy and provides different subscales relating to these.
7 The Short Form (36) Health Survey (SF-36) is a gold standard patient-reported measure of quality of life.
8 The Self-Compassion Scale (SCS) (Neff 2003) Comprises 26 items answered on a 5 point scale. This scale measures core aspects of self-compassion including components of mindfulness.
9 The Trauma History Questionnaire (THQ) (Green 1996) is a self-report measure that examines experiences with potentially traumatic events using a yes/no format. For each event endorsed, respondents are asked to provide the frequency of the event as well as their age at the time of the event.

An assessment may be computer-assisted, and other computer-assisted assessments may be performed besides the assessments above. The term "computer-assisted" in "computer-assisted assessment" means an assessment comprising the use of electronic tools such as online tools, smartphones, wireless devices, or health apps (in some such examples, also known as "digital phenotyping"). Computer-assisted assessment will include the use of an electronic psychiatric notes system, where relevant clinical information will be recorded for the duration of the therapy by a therapist interacting face-to-face with a patient, and will also include the use of computer systems where the therapist and patient interact virtually (either synchronously or asynchronously), as well as where a patient only interacts with a computer ("computer" broadly meaning any electronic tool suitable for such purposes, including desktop, laptop, and notebook computers; tablets, smartphones, and other mobile devices; watches, fitness trackers, and personal electronic devices; and the like). One or more other aspects of a psychosocial, behavioral, or drug-assisted therapy also may be "computer-assisted," wherein one or more steps of such therapy involve the use of a computer in addition to or as a replacement for some work which would otherwise be performed by a therapist.

In embodiments, the invention provides methods of treating and/or preventing a condition, such as a medical condition, in a mammal, the method comprising administering to the mammal a therapeutically effective and/or prophylactically effective amount of a formulation with one or more active agents. As used herein, "treating" or "treatment" covers any treatment of a disorder in a mammal, and preferably in a human, and includes causing a desired biological or pharmacological effect as above, as well as any one or more of: (a) preventing a disorder from occurring in a subject who may be predisposed to the disorder but has not yet been diagnosed with it; (b) inhibiting a disorder, i.e. arresting its development; (c) relieving a disorder, i.e., causing regression thereof; (d) protection from or relief of a symptom or pathology caused by or related to a disorder; (e) reduction, decrease, inhibition, amelioration, or prevention of onset, severity, duration, progression, frequency or probability of one or more symptoms or pathologies associated with a disorder; and (f) prevention or inhibition of a worsening or progression of symptoms or pathologies associated with a disorder or comorbid with a disorder. Other such measurements, benefits, and surrogate or clinical endpoints, alone or in combination, will be understood to one of ordinary skill based on the teachings herein and the knowledge in the art.

In some embodiments, the invention provides methods of improving mental health or functioning, which may include one or more of a reduction of neuroticism or psychological defensiveness, an increase in creativity or openness to experience, an increase in decision-making ability, an increase in feelings of wellness or satisfaction, or an increase in ability to fall or stay asleep, and measurements of such will be readily understood and appreciated according to ordinary skill.

iv. Empathogen-Assisted Therapy

In some embodiments, a disclosed compound or composition thereof is administered together with psychotherapy, such as psychosocial or behavioral therapy, including any of (or adapted from any of) cognitive behavioral therapy (e.g., as described in Arch. Gen. Psychiatry 1999; 56:493-502), interpersonal therapy (e.g., as described in Psychol Addict Behav 2009; 23(1): 168-174), contingency management based therapy (e.g., as described in Psychol Addict Behav 2009; 23(1): 168-174; in J. Consul. Clin. Psychol. 2005; 73(2): 354-59; or in Case Reports in Psychiatry, Vol. 2012, Article ID 731638), motivational interviewing based therapy (e.g., as described in J. Consul. Clin. Psychol. 2001; 69(5): 858-62), meditation based therapy, such as transcendental meditation based therapy (e.g., as described in J. Consul. Clin. Psychol. 2000; 68(3): 515-52), or the therapeutic approach used by MAPS to treat patients with PTSD (e.g., as described in Mithoefer, M (2017). A Manual for MDMA-Assisted Psychotherapy in the Treatment of Post-traumatic Stress Disorder).

Empathogen-assisted psychotherapy, broadly, includes a range of related approaches that involve at least one session where the patient ingests an empathogen (or broadly, a "psychedelic") and is monitored, supported, or otherwise engaged by one or more trained mental health professionals while under the effects of the compound (see, e.g., Schenberg 2018). Protocols have been developed for the standardization of procedures which emphasize a high degree of care (see, e.g., Johnson 2008), such as the therapeutic approach used by MAPS to treat patients with PTSD using MDMA (e.g., as described in Mithoefer 2017).

In some embodiments, the psychotherapy conducted with a disclosed compound or composition is conducted in widely spaced sessions, typically with two administrations of a disclosed compound or composition per session (a first dose, and a "booster" dose, although in some embodiments, only a single dose). These sessions can be as frequently as weekly but are more often approximately monthly or less frequently. In most cases, a small number of sessions, on the order of one to three, is needed for a patient to experience significant clinical progress, as indicated, for example, by a reduction in the symptoms of the mental health disorder being treated. In some embodiments, psychotherapy comprises multiple sessions, during some of which a disclosed compound or composition is administered ("drug-assisted psychotherapy"); in others, the patient participates in psychosocial or behavioral therapy without concomitant administration of a drug, or without administration of a disclosed compound or composition.

In some embodiments, a disclosed compound or composition is administered together with standardized psychological treatment or support, which refers to any accepted modality of standard psychotherapy or counseling sessions, whether once a week, twice a week, or as needed; whether in person or virtual (e.g., over telemedicine or by means of a web program or mobile app); and whether with a human therapist or a virtual or AI "therapist." As used herein, "therapist" refers to a person who treats a patient using the compositions and methods of the invention, whether that person is a psychiatrist, clinical psychologist, clinical therapist, registered therapist, psychotherapist, or other trained clinician, counselor, facilitator, or guide, although it will be understood that certain requirements will be appropriate to certain aspects of the drug-assisted therapy (e.g., prescribing, dispensing, or administering a drug, offering psychotherapeutic support). In some embodiments, a "person" may also include an AI.

In some embodiments, a patient will participate in a treatment protocol or a method of the invention, or be administered a disclosed composition as part of such a method, if the patient meets certain specified inclusion criteria, does not meet certain specified exclusion criteria, does not meet any specified withdrawal criteria during the course of treatment, and otherwise satisfies the requirements of the embodiment of the invention as claimed.

Preferably, where the pharmaceutical compositions of the invention are administered, such administration occurs without or with reduced risk of side effects that would require physician supervision, and therefore allow for treatment at home or otherwise outside of a clinic and without the need for such supervision, and/or additionally without the requirement of adjunctive psychotherapy (although it also may be provided in certain embodiments herein).

In some embodiments, the compositions of the invention may be administered in conjunction with or as an adjunct to psychotherapy. In other embodiments, psychotherapy is neither necessitated nor desired, or no specific type of psychotherapy is necessitated or desired, however any of the disclosed methods can be used in combination with one or more psychotherapy sessions. The flexibility to participate in specific therapies, as well as to choose between any such therapies (or to decide to forgo any specific therapy), while still receiving clinically significant therapeutic effects, is among the advantages of the invention. Furthermore, a patient can participate in numerous other therapeutically beneficial activities, where such participation follows or is in conjunction with the administration of the composition, including breathing exercises, meditation and concentration practices, focusing on an object or mantra, listening to music, physical exercise, stretching or bodywork, journaling, grounding techniques, positive self-talk, or engaging with a pet or animal, and it should be understood that such participation can occur with or without the participation or guidance of a therapist.

In some instances, the described methods comprise certain personalized approaches (i.e., "personalized" or "precision" medicine) may be utilized, based on individual characteristics, including drug metabolism (e.g., CYP2B6, CYP1A2, CYP2C19, CYP2D6, or CYP3A4) or individual genetic variation. The term "genetic variation" refers to a change in a gene sequence relative to a reference sequence (e.g., a commonly-found and/or wild-type sequence). Genetic variation may be recombination events or mutations such as substitution/deletion/insertion events like point and splice site mutations.

In one embodiment, the genetic variation is a genetic variation in one or more cytochrome P450 (CYP or CYP450) enzymes that affects drug metabolism, including metabolism of a disclosed compound, and including CYP1A2, CYP2C9, CYP2D6, CYP2C19, CYP3A4 and CYP3A5. Other examples of CYP enzymes include CYP1A1, CYP1B1, CYP2A6, CYP2A13, CYP2B6, CYP2C8, CYP2C9, CYP2C18, CYP2E1, CYP2G1, CYP2J2, CYP2R1, CYP2S1, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

In some embodiments, a disclosed compound is taken together with a compound that is metabolized by the same CYP enzyme(s) as the disclosed compound, so as to permit a lower dose to be taken, increase the effective bioavailability of one or both, or otherwise affect drug metabolism or pharmacokinetics. In some embodiments, the dose of a disclosed compound is adjusted when administered to a subject known to be a "poor metabolizer" of the active agent in composition (e.g., having a genetic variation in CYP2D6, known to be the major metabolizer of the methylenedioxy moiety). In some embodiments, a genetic variation is an exclusion criteria for the administration of a disclosed compound or composition.

In one embodiment, the genetic variation is a genetic variation in metabotropic glutamate receptor type 5 (mGluR5), which has been implicated in mood and anxiety symptoms in humans. In another embodiment, the genetic variation is one or more single nucleotide polymorphisms (SNPs) in the FKBP5 gene that are associated with elevated levels of FKBP51 protein relative to persons lacking such SNPs. The FKBP5 gene has been implicated in responses to stress and trauma, and such SNPs are correlated with susceptibility to certain depression, PTSD, and anxiety disorders.

In one embodiment, the genetic variation is a genetic variation such as a SNP in a membrane transporter, such as SERT, DAT, NET, or VMAT.

In one embodiment, the mammal being treated has altered epigenetic regulation of a gene the expression of which is associated with a mental health condition or susceptibility to a mental health treatment, such as the SIGMAR1 gene for the non-opioid sigma-1 receptor.

In some embodiments, administration of a deuterium-substituted disclosed compound according to the methods herein will affect a decreased inhibition of, and/or metabolism by, at least one cytochrome P450 enzyme or monoamine oxidase isoform (e.g., MAOA and MAOB) in a subject during treatment, as compared to a corresponding non-substituted composition, which may be a decrease of 5% or more, 10% or more, 25% or more, or 50% or more, and including amounts in between. Measurements of inhibition and metabolism will be as understood by those in the art or by reference to the general knowledge in the art (see e.g., Ko et al., Br J Clin Pharmacol, 2000; 29(4), 343-451, Uebelhack et al., Pharmacopsychiatry, 1998; 31(5), 187-192; Weyler & Salach, J Biol Chem, 1985; 260(24), 13199-13207).

d. Dosing

In some aspects, provided are methods for using therapeutically effective amounts of the disclosed compounds and compositions in a mammal, and preferably a human. In some embodiments, therapeutically effective amounts of the disclosed compounds and compositions are used to modulate neurotransmission. In some embodiments, therapeutically effective amounts of the disclosed compounds and compositions are used to treat a condition, such as a disease or a disorder. In some embodiments, the condition is a mental health disorder. In some embodiments, therapeutically effective amounts of the disclosed compounds and compositions are used to improve mental health and functioning in a subject, including in a healthy individual.

Administration of compositions in a "therapeutically effective amount," or an "effective amount" to a subject means administration of an amount of composition sufficient to achieve the desired effect. When an "effective amount" means an amount effective in treating the stated disorder or symptoms in a subject, "therapeutic effect" would be understood to mean the responses(s) in a mammal after treatment that are judged to be desirable and beneficial. Hence, depending on the mental health disorder to be treated, or improvement in mental health or functioning sought, and depending on the particular constituent(s) in the compositions under consideration, those responses shall differ, but would be readily understood by those of ordinary skill, through an understanding of the disclosure herein and the general knowledge of the art (e.g., by reference to the symptoms listed in the DSM-5 for the stated disorder).

In embodiments, the disclosed pharmaceutical compositions comprise therapeutic amounts of deuterated empathogens and in some embodiments other active or inactive ingredients. Dosage amounts will be understood by reference to all of the teachings herein as well as the general knowledge in the art, but certain exemplary dosage amounts, known to be useful in the practice of the invention, are listed below for ease of reference.

In some embodiments, where a pharmaceutical composition includes a compound of any of Formula (I), Formula (II), Formula (III), and Formula (IV), it may be present in an amount so that a single dose is (in a milligram dosage amount calculated based on the kilogram weight of the patient), e.g., 0.25 mg/kg or less (including a dose of 0.10 mg/kg or less, 0.05 mg/kg or less, 0.01 mg/kg or less, and 0.005 mg/kg or less), at least 0.50 mg/kg, at least 0.55 mg/kg, at least 0.60 mg/kg, at least 0.65 mg/kg, at least 0.70 mg/kg, at least 0.75 mg/kg, at least 0.80 mg/kg, at least 0.85 mg/kg, at least 0.90 mg/kg, at least 0.95 mg/kg, at least 1.0 mg/kg, at least 1.1 mg/kg, at least 1.2 mg/kg, at least 1.3 mg/kg, or at least 1.4 mg/kg, at least 1.5 mg/kg, at least 1.6 mg/kg, at least 1.7 mg/kg, at least 1.8 mg/kg, at least 1.9 mg/kg, at least 2.0 mg/kg, at least 2.1 mg/kg, at least 2.2 mg/kg, at least 2.3 mg/kg, at least 2.4 mg/kg, at least 2.5 mg/kg, at least 2.6 mg/kg, at least 2.7 mg/kg, at least 2.8 mg/kg, at least 2.9 mg/kg, or at least 3.0 mg/kg, as well as amounts within these ranges.

In some embodiments, where a pharmaceutical composition includes a compound of any of Formula (I), Formula (II), Formula (III), and Formula (IV), it may be present in an amount so that a single dose is (whether or not such dose is present in a unit dosage form), e.g., 25 mg or less (including a dose of 10 mg or less, 5 mg or less, 1 mg or less, and 0.5 mg or less), at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 105 mg, at least 110 mg, at least 115 mg, at least 120 mg, at least 125 mg, at least 130 mg, at least 135 mg, at least 140 mg, at least 145 mg, at least 150 mg, at least 155 mg, at least 160 mg, at least 165 mg, at least 170 mg, at least 175 mg, at least 180 mg, at least 185 mg, at least 190 mg, at least 195 mg, at least 200 mg, at least 225 mg, or at least 250 mg, as well as amounts within these ranges.

In some embodiments, where a pharmaceutical composition includes an additional active compound, for instance where the additional active compound is a phenethylamine or tryptamine, it may be present in an amount so that a single dose is (in a milligram dosage amount calculated based on the kilogram weight of the patient), e.g., 0.25 mg/kg or less (including a dose of 0.10 mg/kg or less, 0.05 mg/kg or less, 0.01 mg/kg or less, and 0.005 mg/kg or less), at least 0.50 mg/kg, at least 0.55 mg/kg, at least 0.60 mg/kg, at least 0.65 mg/kg, at least 0.70 mg/kg, at least 0.75 mg/kg, at least 0.80 mg/kg, at least 0.85 mg/kg, at least 0.90 mg/kg, at least 0.95 mg/kg, at least 1.0 mg/kg, at least 1.1 mg/kg, at least 1.2 mg/kg, at least 1.3 mg/kg, or at least 1.4 mg/kg, at least 1.5 mg/kg, at least 1.6 mg/kg, at least 1.7 mg/kg, at least 1.8 mg/kg, at least 1.9 mg/kg, at least 2.0 mg/kg, at least 2.1 mg/kg, at least 2.2 mg/kg, at least 2.3 mg/kg, at least 2.4 mg/kg, at least 2.5 mg/kg, at least 2.6 mg/kg, at least 2.7 mg/kg, at least 2.8 mg/kg, at least 2.9 mg/kg, or at least 3.0 mg/kg, as well as amounts within these ranges.

In some embodiments, where a pharmaceutical composition includes an additional active compound, for instance where the additional active compound is a phenethylamine or tryptamine, it may be present in an amount so that a single dose is (whether or not such dose is present in a unit dosage form), e.g., 25 mg or less (including a dose of 10 mg or less, 5 mg or less, 1 mg or less, and 0.5 mg or less), at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 105 mg, at least 110 mg, at least 115 mg, at least 120 mg, at least 125 mg, at least 130 mg, at least 135 mg, at least 140 mg, at least 145 mg, at least 150 mg, at least 155 mg, at least 160 mg, at least 165 mg, at least 170 mg, at least 175 mg, at least 180 mg, at least 185 mg, at least 190 mg, at least 195 mg, at least 200 mg, at least 225 mg, or at least 250 mg, as well as amounts within these ranges.

It will be readily appreciated that dosages may vary depending upon whether the treatment is therapeutic or prophylactic, the onset, progression, severity, frequency, duration, probability of or susceptibility of the symptom to which treatment is directed, clinical endpoint desired, previous, simultaneous or subsequent treatments, general health, age, gender, and race of the subject, bioavailability, potential adverse systemic, regional or local side effects, the presence of other disorders or diseases in the subject, and other factors that will be appreciated by the skilled artisan (e.g., medical or familial history).

Dose amount, frequency or duration may be increased or reduced, as indicated by the clinical outcome desired, status of the pathology or symptom, any adverse side effects of the treatment or therapy, or concomitant medications. The skilled artisan with the teaching of this disclosure in hand will appreciate the factors that may influence the dosage, frequency, and timing required to provide an amount sufficient or effective for providing a therapeutic effect or benefit, and to do so depending on the type of therapeutic effect desired, as well as to avoid or minimize adverse effects.

It will be understood that, in some embodiments, the dose actually administered will be determined by a physician, in light of the relevant circumstances, including the disorder to be treated, the chosen route of administration, the actual composition or formulation administered, the age, weight, and response of the individual patient, and the severity of the patient's symptoms, and therefore any dosage ranges disclosed herein are not intended to limit the scope of the invention. In some instances, dosage levels below the lower limit of a disclosed range may be more than adequate, while in other cases doses above a range may be employed without causing any harmful side effects, provided for instance that such larger doses also may be divided into several smaller doses for administration, either taken together or separately.

In these embodiments, the pharmaceutical compositions of the invention will be administered and dosed in accordance with good medical practice, taking into account the method and scheduling of administration, prior and concomitant medications and medical supplements, the clinical condition of the individual patient and the severity of the underlying disease, the patient's age, sex, body weight, and other such factors relevant to medical practitioners, and knowledge of the particular compound(s) used. Starting and maintenance dosage levels thus may differ from patient to patient, for individual patients across time, and for different pharmaceutical compositions and formulations, but shall be able to be determined with ordinary skill.

It should be appreciated that in other embodiments, e.g., when the compositions of the invention are taken without the direct intervention or guidance of a medical professional, appropriate dosages to achieve a therapeutic effect, including the upper and lower bounds of any dose ranges, can be determined by an individual by reference to available public information and knowledge, and reference to subjective considerations regarding desired outcomes and effects.

Determination of appropriate dosing shall include not only the determination of single dosage amounts, but also the determination of the number and timing of doses, e.g., administration of a particular dosage amount once per day, twice per day, or more than twice per day, and the time(s) of day or time(s) during a psychotherapeutic session preferable for their administration.

In some embodiments, especially where a formulation is prepared in single unit dosage form, such as a capsule, tablet, or lozenge, suggested dosage amounts shall be known by reference to the format of the preparation itself. In other embodiments, where a formulation is prepared in multiple dosage form, for instance liquid suspensions and topical preparations, suggested dosage amounts may be known by reference to the means of administration or by reference to the packaging and labeling, package insert(s), marketing materials, training materials, or other information and knowledge available to those of skill or the public.

Accordingly, another aspect of this disclosure provides pharmaceutical kits containing a pharmaceutical composition or formulation of the invention, suggested administration guidelines or prescribing information therefor, and a suitable container. Individual unit dosage forms can be included in multi-dose kits or containers. Pharmaceutical formulations also can be packaged in single or multiple unit dosage forms for uniformity of dosage and ease of administration.

In an exemplary pharmaceutical kit, capsules, tablets, caplets, or other unit dosage forms are packaged in blister packs. "Blister pack" refers to any of several types of pre-formed container, especially plastic packaging, that contains separate receptacles (e.g., cavities or pockets) for single unit doses, where such separate receptacles are individually sealed and can be opened individually.

Blister packs thus include such pharmaceutical blister packs known to those of ordinary skill, including Aclar® Rx160, Rx20e, SupRx, and UltRx 2000, 3000, 4000, and 6000 (Honeywell). Within the definition of multi-dose containers, and also often referred to as blister packs, are blister trays, blister cards, strip packs, push-through packs, and the like.

Preferably, information pertaining to dosing and proper administration (if needed) will be printed onto a multi-dose kit directly (e.g., on a blister pack or other interior packaging holding the compositions or formulations of the invention); however, kits of the invention can further contain package inserts and other printed instructions (e.g., on exterior packaging) for administering the compositions of the invention and for their appropriate therapeutic use.

In some embodiments, a patient will have the option of using online software such as a website, or downloadable software such as a mobile application, to assist with compliance or to provide data relating to treatment. Such software can be used to, e.g., keep track of last dose taken and total doses taken, provide reminders and alerts for upcoming doses, provide feedback to discourage taking doses outside of set schedules, and allow for recording of specific subjective effects, or provide means for unstructured journaling. Such data collection can assist with individual patient compliance, can be used to improve or tailor individual patient care plans, and can be anonymized, aggregated, and analyzed (including by AI or natural language processing means) to allow research into the effects of various methods of treatment.

E. General Definitions and Terms

As used in this specification and the appended claims, the singular forms "a," "an," and "the" include plural referents unless the context clearly dictates otherwise. Thus, for example, reference to "an active agent" includes reference to a combination of two or more active agents, and reference to "an excipient" includes reference to a combination of two or more excipients. While the term "one or more" may be used, its absence (or its replacement by the singular) does not signify the singular only, but simply underscores the possibility of multiple agents or ingredients in particular embodiments.

The terms "comprising," "including," "such as," and "having" are intended to be inclusive and not exclusive (i.e., there may be other elements in addition to the recited elements). Thus, the term "including" as used herein means, and is used interchangeably with, the phrase "including but not limited to." The term "or" is used herein to mean, and is used interchangeably with, the term "and/or," unless context clearly indicates otherwise.

Unless otherwise indicated, all numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment.

In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

A comprehensive list of the abbreviations utilized by organic chemists of ordinary skill in the art appears in the first issue of each volume of the Journal of Organic Chemistry; this list is typically presented in a table entitled Standard List of Abbreviations; the current list as of the date of this filing is hereby incorporated by reference as if fully set forth herein.

Unless defined otherwise, all technical and scientific terms herein have the meaning as commonly understood by a person having ordinary skill in the art to which this invention belongs, who as a shorthand may be referred to simply as "one of skill." Further definitions that may assist the reader in understanding the disclosed embodiments are as follows; however, it will be appreciated that such definitions are not intended to limit the scope of the invention, which shall be properly interpreted and understood by reference to the full specification (as well as any plain meaning known to one of skill in the relevant art) in view of the language used in the appended claims. The terminology used herein is for the purpose of describing particular embodiments only, and is not intended to be limiting.

Generally, the nomenclature and terminology used and the procedures performed herein are those known in fields relating to that of one or more aspects of the invention, such as those of biology, pharmacology, neuroscience, organic chemistry, synthetic chemistry, medicinal chemistry, and/or pharmaceutical sciences, and are those that will be well-known and commonly employed in one or more of such fields. Standard techniques and procedures will be those generally performed according to conventional methods in the art. Although any materials and methods similar or equivalent to those described herein can be used in the practice of the invention, certain preferred materials and methods are described herein.

F. Examples

Example 10: Synthesis of Deuterated Empathogens by Reductive Amination

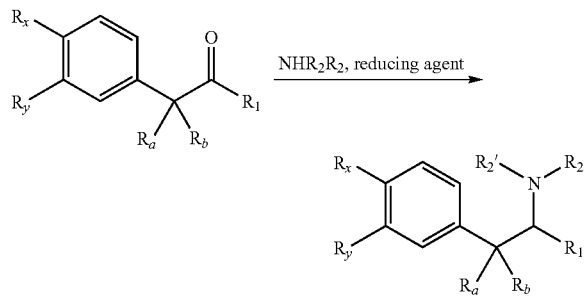

Deuterated empathogens are synthesized according to the following general procedure for reductive amination of a suitable ketone or aldehyde precursor with a deuterated primary or secondary amine.

A round bottom flask equipped with a magnetic stirrer is charged with deuterated primary amine (i.e., NH—$R_2R_{2'}$), or a salt thereof, and a suitable solvent (e.g., MeOH). With stirring, the corresponding ketone or aldehyde precursor is added, followed by a suitable reducing agent (e.g., NaCNBH$_3$). The pH is adjusted to about 7 by the addition of a suitable acid (e.g., hydrochloric acid). The resulting solution or suspension is stirred until conversion is complete, typically overnight.

The product is isolated according to standard procedures in organic chemistry, for example by acid-base work-up. An exemplary acid-base work-up is provided herein: the reaction mixture is then poured into an acidic aqueous solution, for example dilute aqueous hydrochloric acid. The aqueous phase is washed with a suitable organic solvent (e.g., CH$_2$Cl$_2$). The pH is then adjusted to approximately pH 11-12 by addition of a suitable alkaline solution, for example an aqueous sodium hydroxide solution. The resulting aqueous solution is then extracted with a suitable organic solvent (e.g., CH$_2$Cl$_2$). The pooled organic extracts are dried over a suitable drying agent (e.g., Na$_2$SO$_4$, MgSO$_4$). Subsequent evaporation of the volatiles yields the target compound, typically as an oil which can be further purified by crystallization as a salt. For example, the target compound may be converted to its hydrochloride salt by dissolving the crude oil in a suitable solvent (e.g., isopropanol) adding hydrochloric acid, optionally alongside a second solvent (e.g., diethyl ether), and waiting for crystallization to occur (typically overnight). Crystals of the hydrochloride salt can then be isolated by filtration, washed with a suitable solvent (e.g., diethyl ether), and dried under vacuum or by suction to yield the target deuterated empathogen as the hydrochloride salt.

Example 11: Synthesis of Deuterated Empathogens by Amination of an Alkyl Halide Precursor

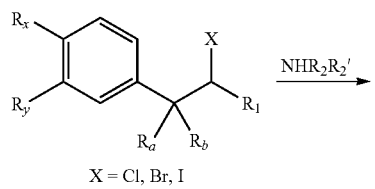

X = Cl, Br, I

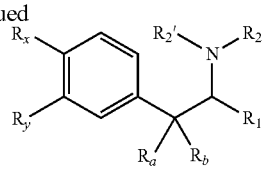

Deuterated empathogens are synthesized according to the following general procedure for amination of a suitable alkyl halide precursor with a deuterated primary or secondary amine.

A round bottom flask equipped with a magnetic stirrer is charged with deuterated primary amine (i.e., NH—$R_2R_{2'}$), or a salt thereof, a suitable base (e.g., triethylamine), and a suitable solvent (e.g., CH$_2$Cl$_2$). With stirring, the corresponding alkyl halide precursor is added and the reaction is stirred at ambient temperature. The reaction can be monitored by GC-MS.

The product is then isolated from the reaction mixture using standard techniques, for example using the purification procedure described in Example 10.

Example 12: Synthesis of Deuterated Empathogens by Leuckart Reaction

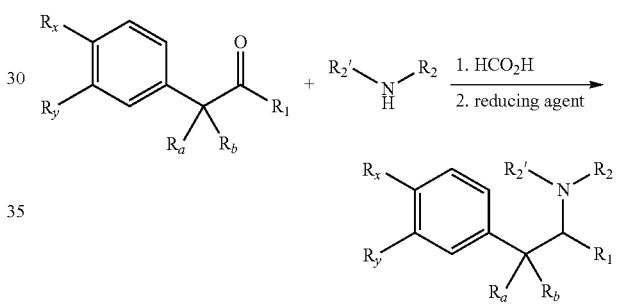

Deuterate empathogens are synthesized according to the following genera procedure for the Leuckart reaction of a suitable ketone or aldehyde precursor with a deuterated primary or secondary amine.

A round bottom flask equipped with a magnetic stirrer is charged with deuterated primary amine (i.e., NH—$R_2R_{2'}$), or a salt thereof, formic acid, a suitable ketone or aldehyde precursor, and a suitable solvent (e.g., DMF). The reaction is heated (e.g., to reflux) and optionally monitored by GC-MS.

The product is isolated from the reaction mixture using standard techniques, for example using the purification procedure described in Example 10.

Example 13: Synthesis of Deuterated MDMA

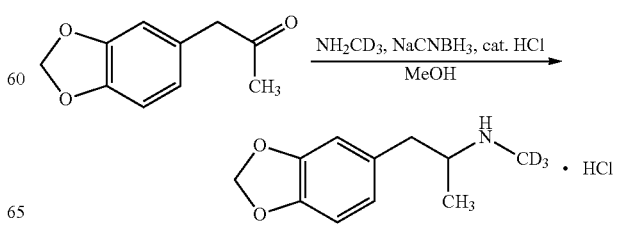

MDMA-d3 was synthesized according to the procedure described in Example 10. Specifically, a 100 mL round bottom flask equipped with a magnetic stirrer was charged with NH$_2$CD$_3$-HCl (10.0 g) and MeOH (42 mL). With stirring, 1-(benzo[d][1,3]dioxol-5-yl)propan-2-one (2.63 g) was added to the flask, followed by NaCNBH$_3$ (1.16 g). Hydrochloric acid (12 N) was added until a pH of 7 was achieved (ca. 5 drops). The resulting suspension was stirred overnight. The reaction mixture was then poured into an aqueous solution of 12 N hydrochloric acid (1.25 mL) in water (500 mL). The aqueous phase was washed with CH$_2$Cl$_2$ (2×50 mL). The aqueous phase was adjusted to pH 11-12 by the addition of a 25% aqueous NaOH solution. The aqueous phase was then extracted with CH$_2$Cl$_2$ (4×50 mL). The combined organic extracts were dried over anhydrous Na$_2$SO$_4$ overnight with stirring. After gravity filtration of the Na$_2$SO$_4$, the volatiles were removed by rotary evaporation to yield a yellow-green oil (2.96 g). The oil was dissolved in isopropanol (30 mL), to which was added 12 N hydrochloric acid (1.2 mL) and diethyl ether (60 mL). Crystallization occurred overnight. The crystals were recovered by filtration through a fritted funnel, washed with diethyl ether (2×30 mL), and dried via suction to yield MDMA-d3 as the hydrochloride salt (2.4 g).

Example 14: Synthesis of Deuterated Methylone (bk-MDMA)

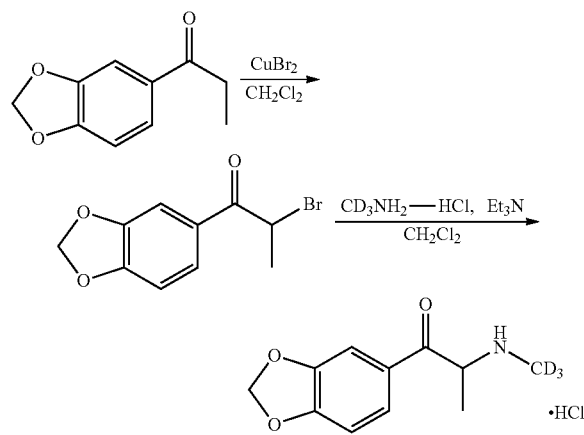

Methylone-d3 was synthesized according to the procedure described in Example 2. Specifically, a 500 mL round bottom flask equipped with a magnetic stirrer was charged with 3,4-methylenedioxypropiophenone (27.7 g) and CH$_2$Cl$_2$ (250 mL). CuBr$_2$ (68.2 g) was ground in a mortar and pestle and added to the flask over 10 minutes. The reaction was heated to reflux in a warm water bath. After 6 h, an additional portion of CuBr$_2$ (68.2 g) was added and the reaction continued stirring overnight. The reaction was monitored by GC-MS. After 72 h, the reaction was filtered and the gray solids were washed with CH$_2$Cl$_2$ (3×150 mL). The combined filtrate and washes were filtered through an alumina plug, and the solvent was removed by rotary evaporation to yield α-bromomethylenedioxypropiophenone (33.73 g, 84.4% yield) as a light brown solid that was used in the next step without further purification.

A 50 mL Erlenmeyer flask equipped with a magnetic stir bar was charged with methylamine-d3 HCl (0.277 g), triethylamine (1.583 g), and CH$_2$Cl$_2$ (10 mL). α-bromomethylenedioxypropiophenone (2.008 g) was added and the reaction was stirred at ambient temperature. The reaction was monitored by GC-MS and continued stirring for 4 h. Beige solids precipitated during the reaction. The suspension was poured into water (20 mL) and gently shaken with CH$_2$Cl$_2$ (15 mL). The aqueous layer was acidified with aqueous HCl (1 M) to pH ~2.5, and then washed with CH$_2$Cl$_2$ (3×15 mL), resulting in a pale yellow aqueous layer. To this aqueous layer was added diethyl ether (15 mL). The aqueous layer was basified with NaOH (ca. 40 drops of 25% aqueous NaOH) to a pH of 10. The organic layer was removed, and the aqueous layer was extracted again with diethyl ether (2×10 mL). The combined ether extracts were dried with anhydrous MgSO$_4$, then neutralized with 40 drops concentrated HCl, which produced a filterable white powder. A small amount of color was removed by treatment with boiling methyl ethyl ketone, which after drying resulted in methylone-d3 (639 mg, 21.6% yield).

Example 15: Synthesis of Deuterated Ethylone

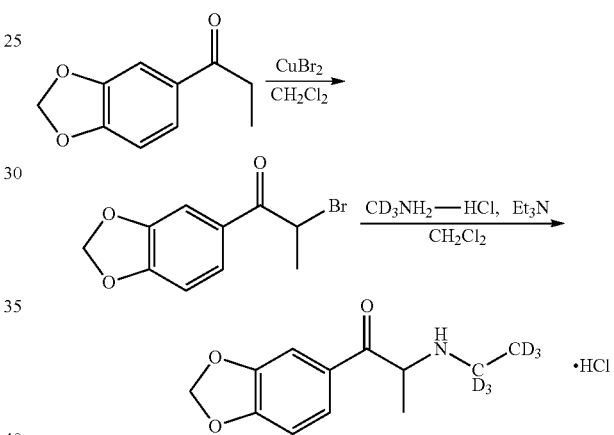

Ethylone-d5 was synthesized according to the procedure described in Example 2. Specifically, a 500 mL round bottom flask equipped with a magnetic stirrer was charged with 3,4-methylenedioxypropiophenone (27.7 g) and CH$_2$Cl$_2$ (250 mL). CuBr$_2$ (68.2 g) was ground in a mortar and pestle and added to the flask over 10 minutes. The reaction was heated to reflux in a warm water bath. After 6 h, an additional portion of CuBr$_2$ (68.2 g) was added and the reaction continued stirring overnight. The reaction was monitored by GC-MS. After 72 h, the reaction was filtered and the gray solids were washed with CH$_2$Cl$_2$ (3×150 mL). The combined filtrate and washes were filtered through an alumina plug, and the solvent was removed by rotary evaporation to yield α-bromomethylenedioxypropiophenone (33.73 g, 84.4% yield) as a light brown solid that was used in the next step without further purification.

A 50 mL Erlenmeyer flask equipped with a magnetic stir bar was charged with ethylamine-d5 HCl (0.55 g), triethylamine (1.303 g), and CH$_2$Cl$_2$ (10 mL). α-bromomethylenedioxypropiophenone (1.637 g) was added and the reaction was stirred at ambient temperature. The reaction was monitored by GC-MS and continued stirring for 4 h. Beige solids precipitated during the reaction. The suspension was poured into water (20 mL) and gently shaken with CH$_2$Cl$_2$ (15 mL). The aqueous layer was acidified with aqueous HCl (1 M) to pH ~2.5, and then washed with CH$_2$Cl$_2$ (3×15 mL), resulting in a pale yellow aqueous layer. To this aqueous layer was added diethyl ether (15 mL). The aqueous layer was basified with NaOH (ca. 40 drops of 25% aqueous NaOH) to a pH of 10. The organic layer was removed, and the aqueous layer was extracted again with diethyl ether (2×10 mL). The combined ether extracts were dried with anhydrous $MgSO_4$, then neutralized with 40 drops concentrated HCl, which produced a filterable white powder. A small amount of color was removed by treatment with boiling methyl ethyl ketone, which after drying resulted in ethylone-d5 (795 mg, 30.5% yield).

Example 16: Determination of Octanol-Water Partition Coefficients

The octanol-water partition coefficient (i.e., $K_{ow}$) is determined according to known procedures. For example, a solution of the test compound is provided in n-octanol or water. If the test compound is provided as a solution in water, n-octanol is subsequently added to the aqueous solution and the mixture is allowed to equilibrate. Likewise, if the test compound is provided as a solution in n-octanol, water is subsequently added to the aqueous solution and the mixture is allowed to equilibrate. Concentrations of the test compound in the aqueous and n-octanol layers are determined by any suitable method (e.g., GC-MS, NMR) and the log P value of the test compound is determined according to the following formula: $\log(K_{ow})=\log P$.

Example 17: Prodrugs of Deuterated Empathogens

Prodrugs of deuterated empathogens are synthesized according to known procedures, for example by converting the amine of the deuterated empathogen into an amide.

Amino acid prodrugs are synthesized according to the following reaction scheme:

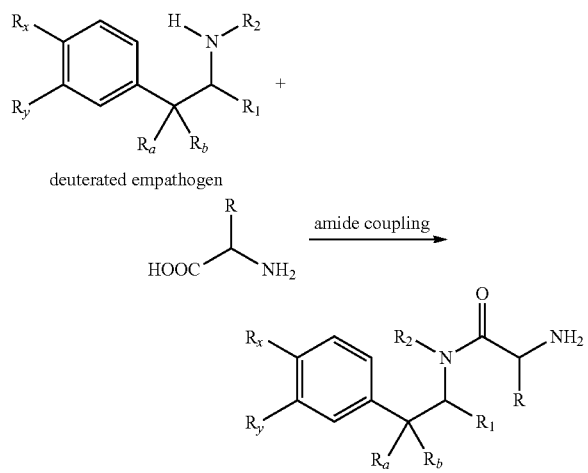

Alternatively, pyridoxal or pyridoxal phosphate prodrugs are synthesized according to the following reaction schemes:

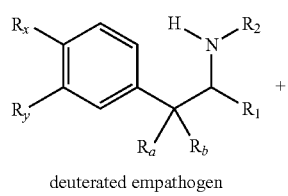

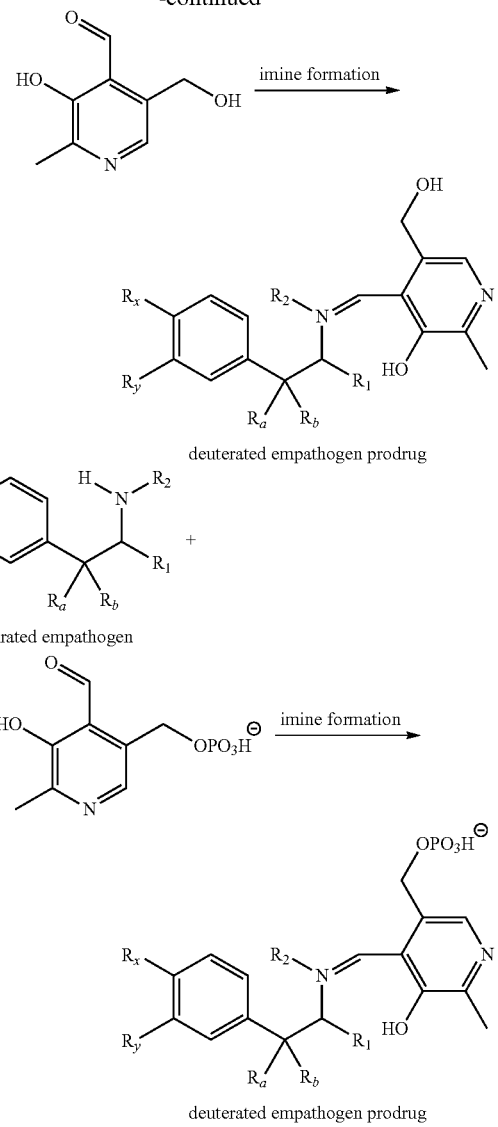

Example 18: Gas Chromatography Mass Spectrometry (GC-MS) Analysis of Deuterated Empathogens Throughout, reactions and final products were analyzed by GC/MS. Two instruments were used: GC1 was an HP 6890 GC with an HP 5973 single quadrupole mass spectrometer (MSD), running Agilent MSD Chemstation D.01.01; and GC2 was an HP 6890 with an Agilent 5973N MSD, running Agilent MSD Chemstation E.02.02. The spectrometers were tuned weekly using PFTBA (perfluorotertiarybutylamine), using the Agilent MSD Chemstation AutoTune routines. Samples were either free bases, or if crystalline salts, were dissolved in water, made basic, then extracted into DCM for GC injection as free bases. Sample concentrations were adjusted to approximately 1 mg/mL, and all sample injections were 1.0 μL, made with Agilent 7673 autosamplers.

GC1 was fitted with an Agilent Ultra-1, 0.20 mm×50m× 0.33 μm, 100% dimethylpolysiloxane column. The carrier gas was hydrogen at 9.0 psi, and an injector temperature of 250 C, operated in splitless mode. The purge time was 0.05 minutes, with a purge flow of 20.1 mL/min. The column oven ramp was initially at 50 C, with an 0.5 min hold, then ramped at 25.0 C/min to a final temperature of 320 C, which was held for 2.20 minutes. The MSD transfer line was set at 300 C, the MSD Source at 230 C, and the MSD Quads at 150 C. The MS was operated in full scan mode, from 40 to 500 amu.

GC2 was fitted with a J&W Scientific 122-1032, 0.10 mm×10m×0.10 μm column, 100% dimethylpolysiloxane column. The carrier gas was hydrogen at 9.8 psi, and an injector temperature of 250 C, operated in split mode with a 20:1 split, split flow of 4.2 mL/min and total flow of 8.6 mL/min. The column oven ramp was initially at 45 C, with a 1.0 min hold, then ramped at 35.0 C/min to a final temperature of 280 C, which was held for 0.29 minutes. The MSD transfer line was set at 300 C, the MSD Source at 230 C, and the MSD Quads at 150 C. The MS was operated in full scan mode, from 40 to 400 amu.

GC-MS data for deuterated empathogens are provided below:

| Compound | Chemical Formula | Exact Mass | Molecular Weight | Found m/z |
|---|---|---|---|---|
| 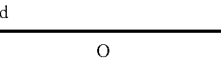 | $C_{11}H_{10}D_3NO_3$ | 210.1084 | 210.2473 | 210.1084 (100%) 211.1117 (11.9%) |
| 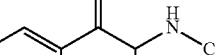 | $C_{12}H_{10}D_5NO_3$ | 226.1366 | 226.2865 | 226.1366 (100%) 227.1399 (13.0%) |

Example 19: In Vitro Receptor and Transporter Interactions

Purpose: A comprehensive study was conducted to profile the interactions of MDMA and a deuterated analog thereof with various receptors, transporters, and ion channels. Comparisons may then be made regarding the pharmacological activity of a deuterated compound and its undeuterated counterpart, among other empathogens. Among other targets, activity was assessed at serotonin receptors $HTR_{1A}$, $HTR_{1B}$, $HTR_{2A}$, $HTR_{2B}$, $HTR_{5A}$ $HTR_6$ $HTR_{7D}$, monoamine transporters DAT, NET, and SERT, and the nicotinic acetylcholine receptor nAChR (a4/b2).

Methods—Arrestin: Activation of $HTR_{5A}$ and $HTR_6$, was determined using the PathHunter® β-Arrestin assay. The assay monitors restoration of β-galactosidase (β-Gal) as a marker of GPCR activation and recruitment of β-Arrestin to the receptor.

To determine agonistic activity, cells were expanded from freezer stocks, seeded into multi-well plates, and incubated at 37° C. prior to addition of a test compound. 3.5 μL of concentrated sample was added to cells and incubated at 37° C. or room temperature for 90 to 180 minutes. Vehicle concentration was 1%.

Assay signal was generated through a single addition of 50% v/v of PathHunter Detection reagent cocktail, followed by a one hour incubation at room temperature. Microplates were read following signal generation with a plate reader set to detect chemiluminescent signals. Compound activity was analyzed using CBIS data analysis suite (ChemInnovation, CA).

Percentage activity was calculated using the following formula:

% Activity=100%×(mean RLU of test sample−mean RLU of vehicle control)/(mean MAX control ligand −mean RLU of vehicle control).

Methods—cAMP: Activation of $HTR_{1B}$ and GRM2, among other targets, was determined using the Hit Hunter® cAMP assay. The assay monitors the activation of a GPCR via Gi and Gs secondary messenger signaling, using β-Gal as a functional reporter.

To determine agonistic activity at Gi/Gs, cells were expanded from freezer stocks, seeded into multi-well plates, and incubated at 37° C. prior to addition of a test compound. To determine Gi/Gs agonism, media was aspirated from cells and replaced with 15 μL 2:1 HBSS/10 mM HEPES: cAMP XS+Ab reagent. Concentrated (4×) test compound in assay buffer was added to cells and incubated at 37° C. or room temperature for 30 or 60 minutes. For Gi agonist activation, cells were incubated with EC80 forskolin in addition to a test compound. Vehicle concentration was 1%.

Compound activity was analyzed using CBIS data analysis suite (ChemInnovation, CA).

For Gs agonist mode assays, percentage activity was calculated using the following formula:

% Activity=100%×(mean RLU of test sample−mean RLU of vehicle control)/(mean RLU of MAX control−mean RLU of vehicle control).

For Gi agonist mode assays, percentage activity was calculated using the following formula:

% Activity=100%×(1−(mean RLU of test sample− mean RLU of MAX control)/(mean RLU of vehicle control−mean RLU of MAX control)).

Methods—Calcium Mobilization: GPCR activity of serotonin receptor 2B ($HTR_{2B}$), among others, was measured using the Calcium No Wash$^{Plus}$ assay, which monitors calcium mobilization in cell lines expressing Gq-coupled GPCRs by loading a calcium-sensitive dye into cells. Administration of a compound results in the release of calcium from intracellular stores and an increase in dye fluorescence that can be measured.

Cell lines were expanded from freezer stocks and seeded into multi-well microplates. Then, the plates were incubated at 37° C. for an appropriate amount of time and loaded with Dye Loading buffer. To determine compound agonist activity, cells were incubated with the sample to induce a response, and HBSS/20 mM Hepes was added using a FLIPR Tetra (MDS). Activity was measured on a FLIPR Tetra. Calcium mobilization was monitored for 2 minutes.

To determine compound antagonist activity, cells were pre-incubated with the sample followed by an post-incubation administration of the compound with 3×EC$_{80}$ agonist using FLIPR. Compound antagonist activity was measured on a FLIPR Tetra (MDS) and calcium mobilization was monitored for 2 minutes.

Compound activity was analyzed using CBIS data analysis suite (ChemInnovation, CA). For agonist mode assays, percentage activity was calculated using the following formula:

% Activity=100%×(mean RFU of test sample−mean RFU of vehicle control)/(mean MAX RFU control ligand −mean RFU of vehicle control).

For antagonist mode assays, percentage inhibition was calculated using the following formula:

% Inhibition=100%×(1−(mean RFU of test sample−mean RFU of vehicle control)/(mean RFU of EC$_{80}$ control−mean RFU of vehicle control)).

Methods—Monoamine Transporter Assay: Neurotransmitter uptake via transporters was measured using the Neurotransmitter Transporter Uptake Assay Kit from Molecular Devices. Dopamine, norepinephrine or serotonin transporter activity in cells was detected using a homogeneous fluorescence based assay. Increased intracellular fluorescence intensity following uptake of biogenic amine neurotransmitters via transporters is measured and can be run in a kinetic or endpoint mode.

To determine percentage inhibition of neurotransmitter uptake via transporter, cell lines were expanded from freezer stocks, seeded into a multi-well microplate, and incubated at 37° C. Then, the compound was administered and the mix was incubated again. Following compound incubation, dye was added to the wells and the plate was re-incubated. Microplates were then transferred to a PerkinElmer Envision™ instrument for fluorescence signal detection.

Compound activity was analyzed using CBIS data analysis suite (ChemInnovation, CA). For blocker mode assays, percentage inhibition was calculated using the following formula:

% Inhibition=100%×(1−(mean RLU of test sample−mean RLU of vehicle control)/(mean RLU of positive control−mean RLU of vehicle control)).

Methods—Ion Channel Assay: Membrane potential changes were measured using the FLIPR® Membrane potential Assay Kit. A fluorescent indicator dye in combination with a quencher is used to reflect real-time membrane potential changes associated with ion channel activation and ion transporter proteins.

To determine agonist and antagonist activity, cell lines were expanded from freezer stocks, seeded into multi-well microplates, and incubated at 37° C. Cells were then loaded with dye and incubated again.

For agonist determination, cells were incubated with the sample a different dilutions to induce a response. For antagonist determination, cells were pre-incubated with the sample at different dilutions. Following dye administration, the sample was added to the cells in the presence of EC$_{80}$ agonist and then re-incubated at room temperature in the dark.

Compound activity was analyzed using CBIS data analysis suite (ChemInnovation, CA). For agonist mode assays, percentage activity was calculated using the following formula:

% Activity=100%×(mean RLU of test sample−mean RLU of vehicle control)/(mean MAX control ligand−mean RLU of vehicle control).

For antagonist mode assays, percentage inhibition was calculated using the following formula:

% Inhibition=100%×(1−(mean RLU of test sample−mean RLU of vehicle control)/(mean RLU of EC$_{80}$ control−mean RLU of vehicle control)).

Results & Significance: Table 2 shows in vitro activity of MDMA and MDMA-d3 at targets where the EC50 was determined to be less than 10 μM. In each case the activity of positive controls are also shown. The compounds displayed an EC$_{50}$ of >10 μM at other targets, indicating relatively weak activity at such targets.

TABLE 2

In Vitro Activity of MDMA and MDMA-d3

| Target | MDMA (EC$_{50}$/IC$_{50}$ in μM) | MDMA-d3 (EC$_{50}$/IC$_{50}$ in μM) | Positive control (EC$_{50}$/IC$_{50}$ in μM) |
|---|---|---|---|
| HTR$_{1B}$ (agonist mode) | 4.71 | 2.99 | Serotonin HCl (0.00011) |
| HTR$_{2B}$ (antagonist mode) | 5.34 | 4.20 | LY272015 (0.00096) |
| DAT (blocker) | 9.84 | 7.57 | GBR12909 (0.0021) |
| NET (blocker) | 2.49 | 3.87 | Despiramine (0.0086) |
| nAChR (a4/b2) (blocker) | 3.19 | 4.38 | Dihyro-AY-erythroidine (0.73) |

Although the EC$_{50}$ of MDMA and MDMA-d3 was determined to exceed 10 μM, the compounds did induce a response at the tested levels. An exemplary comparison between the two compounds is provided in Table 3.

TABLE 4

Max Responses (RLU) of MDMA and MDMA-d3

| Receptor | MDMA Max Response (RLU) | MDMA-d3 Max Response (RLU) |
|---|---|---|
| HTR$_{5A}$ | 4.77 | 0 |
| HTR$_6$ | 3.65 | 1.43 |
| HTR$_{7D}$ | 4.02 | 5.66 |
| GRM2 | 16.4 | 10.8 |

Example 20: Metabolic Stability

Purpose: To determine the metabolic stability of a disclosed compound relative to its corresponding undeuterated compound and reference compound MDMA-d3. Metabolic stability assays measure the intrinsic clearance (CL$_{int}$) of a compound, providing critical data needed to calculate other key pharmacokinetic parameters such as bioavailability and half-life (t$_{1/2}$).

Methods: A high-throughput assay is used to determine metabolic stability of disclosed compounds and undeuterated analogs thereof in various matrices, including human liver microsomes, using LCMS analysis to quantify the percent compound remaining after incubation. Briefly, the disclosed compound is mixed with liver microsomes and activated. Following this incubation, acetonitrile is added to terminate the reaction. Then, the samples are centrifuged and the supernatant is dried. The residue is reconstituted and analyzed using liquid chromatography-mass spectrometry. Pharmacokinetic parameters are calculated using a noncompartmental model. The half-life ($t_{1/2}$) is estimated from the slope of the initial linear range of the logarithmic curve of compound remaining (%) versus time, assuming first order kinetics.

Results & Significance: Disclosed compounds may have reduced clearance and an increased $t_{1/2}$ relative to corresponding undeuterated analogs of MDMA. In some cases, disclosed compounds may have comparable or reduced $CL_{int}$ relative to MDMA-d3, which results in a comparable or increased $t_{1/2}$. Reduced $CL_{int}$ and increased $t_{1/2}$ provide advantages, e.g., suitability for use in the treatment applications described herein.

Example 21: In Vitro Metabolic Profiling

Purpose: To determine whether the disclosed compounds are metabolized and to identify metabolites thereof.

Methods: An in vitro study is conducted to evaluate metabolism and metabolites of disclosed compounds in human liver microsomes, such as S9 hepatocytes. Briefly, disclosed compounds are incubated with human liver microsomes and/or various recombinant enzymes to determine metabolism and formation of metabolites. Following incubation, the supernatant is analyzed directly by ultra-high performance liquid chromatography-mass spectrometry.

Phase I and/or Phase II metabolites are identified using mass spectrometry (MS). The % compound remaining and half-life of the disclosed compound (parent compound) are determined. MS data, such as extracted ion chromatograms, show parent and major metabolites. Metabolic transformation for each observed metabolite is elucidated, and metabolite masses, peak areas, and retention times are determined. Metabolic profiling may also be conducted according to the methods described in Muller & Rentsch, Anal Bioanal Chem, 2012; 402:2141-2151 and Pedersen et al., Drug Metab Dispos, 2013; 41:1247-1255.

Results & Significance: Compounds that undergo metabolism in vivo may produce pharmacologically active or chemically reactive metabolites that produce unexpected effects or potential toxicities. The FDA Guidance for Industry on Safety Testing of Drug Metabolites highlights the relevance of in vitro metabolite profiling early in drug development, as metabolites which are unique to or disproportionate in humans may require additional toxicological studies.

Example 22: In Vitro CYP Enzyme Inhibition

Purpose: To assess the interactions between disclosed compounds and cytochrome P450 (CYP450) enzymes. Such interactions will provide insight into metabolism-mediated drug-drug interactions, which can occur when a compound affects the pharmacokinetics, such as the absorption, distribution, metabolism, and excretion, of simultaneously administered drugs by altering the activities of drug metabolizing enzymes and/or drug transporters.

Methods: An in vitro study is conducted to assess the inhibitory effect of the disclosed compound on recombinant human CYP450 isoenzymes. Recombinant human CYP450 isoenzymes are used to metabolize pro-fluorescent probe substrates to fluorescent products. Inhibition of human P450 isoforms is measured by reduced fluorescence following treatment with the disclosed compound at various concentrations.

Briefly, the disclosed compound is incubated in different concentrations in a mix containing buffer, enzymes, and substrate. Then, fluorescence is measured using a plate reader and percentage inhibition may be extrapolated out from the readings. Alternatively, the inhibitory effects of the disclosed compound on CYP enzymes may be assessed using high-performance liquid chromatography. Inhibition is evaluated using the Michaelis-Menten method. CYP enzyme inhibition may be conducted according to the methods described in Lin et al., J Pharm Sci. 2007 September; 96(9):2485-95 and Wójcikowski et al., Pharmacol Rep. 2020 June; 72(3):612-621.

Results & Significance: Metabolizing enzymes in the liver, such as CYP450 enzymes, are responsible for the majority of drug metabolism that occurs in the body. Six CYP450 class enzymes metabolize 90 percent of drugs, and two of the most significant metabolizers are CYP3A4 and CYP2D6 (Lynch & Price, Am Fam Physician. 2007; 76(3): 391-6). Compounds can interact with such enzymes by inhibiting their enzymatic activity (CYP inhibition) or by inducing their gene expression (CYP induction).

For context, MDMA has been shown to inhibit CYP2D6. See, e.g., Heydari et al., Drug Metab Dispos. 2004; 32(11): 1213-7. CYP2D6 plays a role in both major and minor routes of MDMA metabolism, 0-demethylation forming (6)-3,4-dihydroxymethamphetamine (HHMA) and N-demethylation resulting in (6)-3,4-methylenedioxyamphetamine (MDA), respectively.

The foregoing description, for purposes of explanation, uses specific nomenclature to provide a thorough understanding of the invention. However, it will be apparent to one skilled in the art that specific details are not required in order to practice the invention. Thus, the foregoing description of specific embodiments of the invention is presented for purposes of illustration and description. It is not intended to be exhaustive or to limit the invention to the precise forms disclosed; obviously, many modifications and variations are possible in view of the above teachings. The embodiments were chosen and described in order to best explain the principles of the invention and its practical applications, through the elucidation of specific examples, and to thereby enable others skilled in the art to best utilize the invention and various embodiments with various modifications as are suited to the particular use contemplated, when such uses are beyond the specific examples disclosed. Accordingly, the scope of the invention shall be defined solely by the following claims and their equivalents.

The invention claimed is:

1. A method of treating a mental health disorder in a subject, comprising administering to the subject a therapeutically effective amount of a compound of any of Formulas (IIIA), (IIIB), (IIIC), (IIIE), (IIIF), (IVA), (IVB), or (IVC):

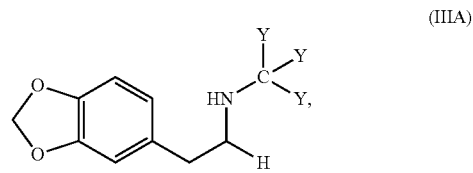

(IIIA)

-continued

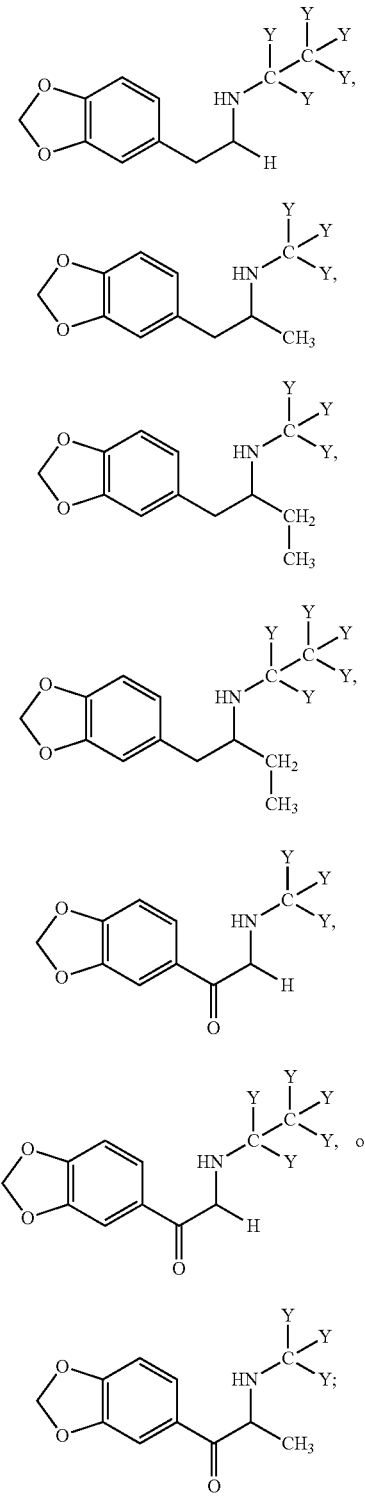

wherein each Y is independently protium (H) or deuterium (D), and wherein at least one Y is deuterium (D) and the remaining Ys are protium (H);

or a pharmaceutically acceptable salt, prodrug, hydrate, or solvate thereof;

provided that the compound is not

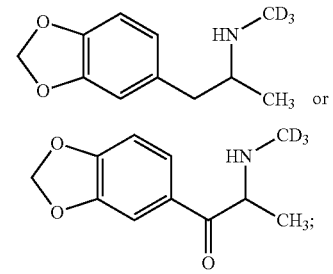

and wherein the mental health disorder is a trauma- or stressor-related disorder, an anxiety disorder, or a depressive disorder.

2. The method of claim 1, comprising administering a compound of any of Formulas (IIIA), (IIIB), (IIIC), (IIIE), or (IIIF):

or a pharmaceutically acceptable salt, prodrug, hydrate, or solvate thereof;

provided that the compound is not

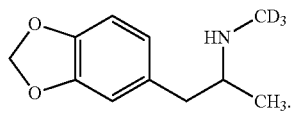 [SMILES: [2H]C([2H])([2H])NC(C)Cc1ccc2c(c1)OCO2]

3. The method of claim 2, comprising administering a compound of Formula (IIIA) selected from the group consisting of:

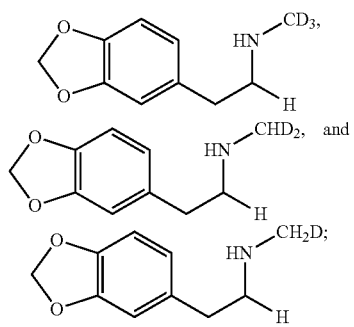

or a pharmaceutically acceptable salt, prodrug, hydrate, or solvate thereof.

4. The method of claim 2, comprising administering a compound of Formula (IIIB) selected from the group consisting of:

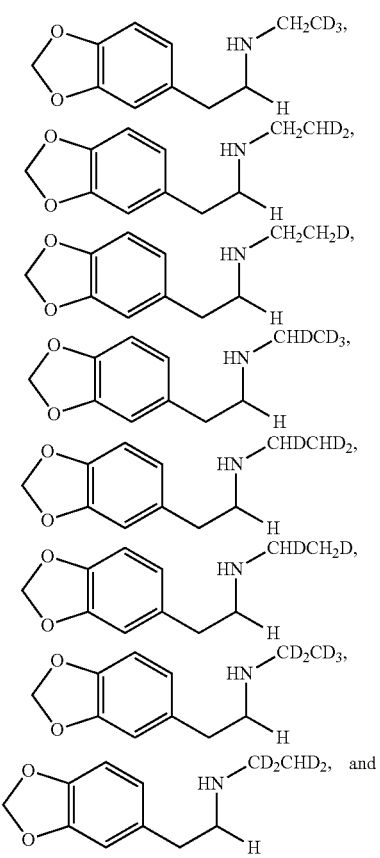

-continued

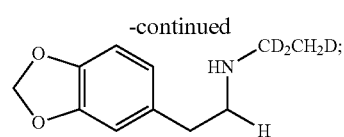

or a pharmaceutically acceptable salt, prodrug, hydrate, or solvate thereof.

5. The method of claim 2, comprising administering a compound of Formula (IIIE) selected from the group consisting of:

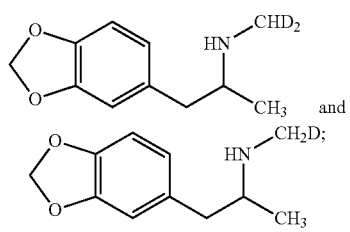

or a pharmaceutically acceptable salt, prodrug, hydrate, or solvate thereof.

6. The method of claim 2, comprising administering a compound of Formula (IIIE) selected from the group consisting of:

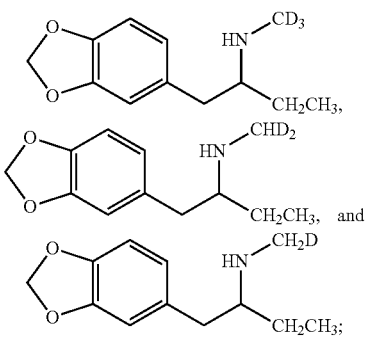

or a pharmaceutically acceptable salt, prodrug, hydrate, or solvate thereof.

7. The method of claim 2, comprising administering a compound of Formula (IIIF) selected from the group consisting of:

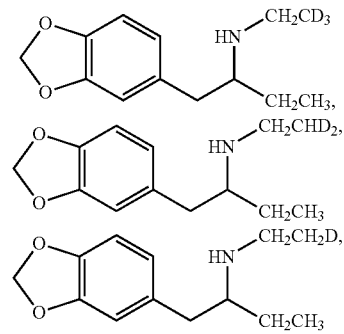

-continued

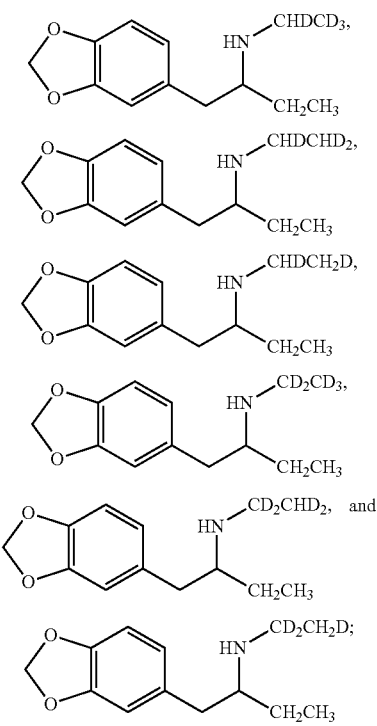

or a pharmaceutically acceptable salt, prodrug, hydrate, or solvate thereof.

8. The method of claim 1, comprising administering a compound of any of Formulas (IVA), (IVB), or (IVC):

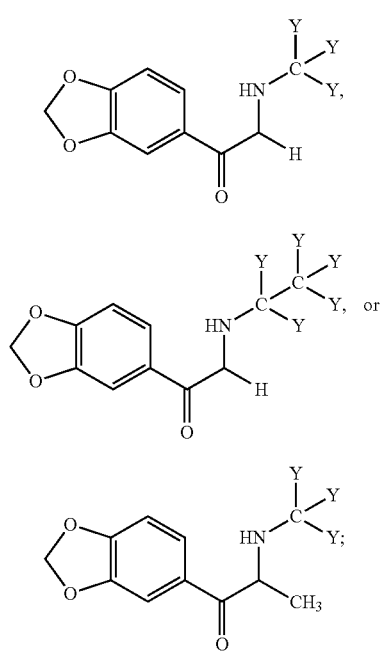

or a pharmaceutically acceptable salt, prodrug, hydrate, or solvate thereof;

provided that the compound is not

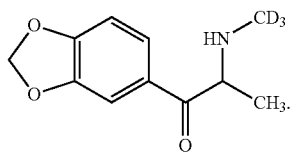 [SMILES: [2H]C([2H])([2H])NC(C)C(=O)c1ccc2c(c1)OCO2]

9. The method of claim 8, comprising administering a compound of Formula (IVA) selected from the group consisting of:

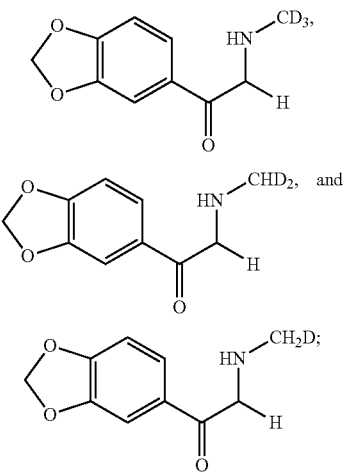

or a pharmaceutically acceptable salt, prodrug, hydrate, or solvate thereof.

10. The method of claim 8, comprising administering a compound of Formula (IVB) selected from the group consisting of:

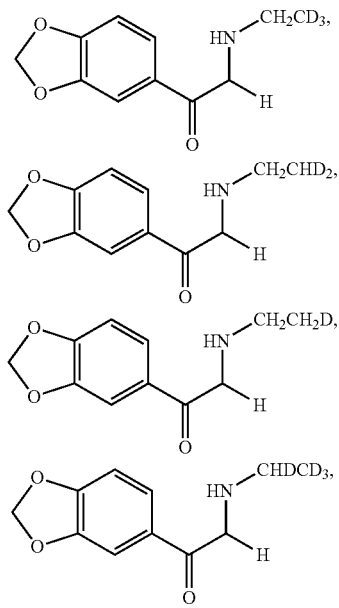

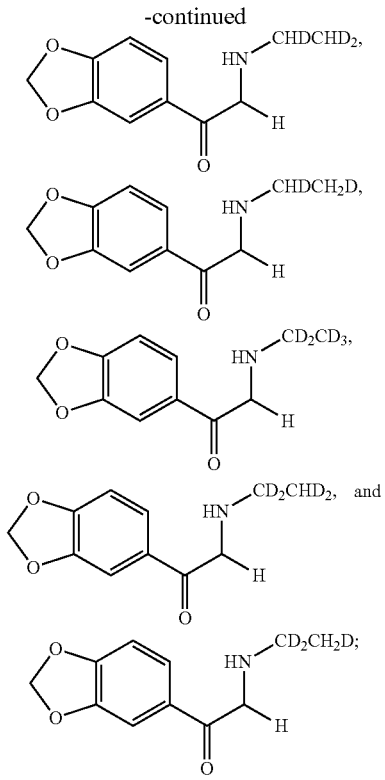

or a pharmaceutically acceptable salt, prodrug, hydrate, or solvate thereof.

11. The method of claim 8, comprising administering a compound of Formula (IVC) selected from the group consisting of:

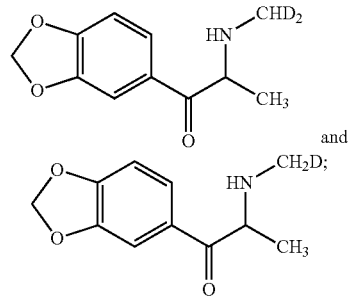

or a pharmaceutically acceptable salt, prodrug, hydrate, or solvate thereof.

12. The method of claim 1, wherein the trauma- or stressor-related disorder is acute stress disorder (ASD).

13. The method of claim 1, wherein the trauma- or stressor-related disorder is an adjustment disorder.

14. The method of claim 1, wherein the trauma- or stressor-related disorder is post-traumatic stress disorder (PTSD).

15. The method of claim 1, wherein the anxiety disorder is generalized anxiety disorder (GAD).

16. The method of claim 1, wherein the depressive disorder is major depressive disorder (MDD).

17. The method of claim 1, wherein the depressive disorder is treatment-resistant depression (TRD).

18. The method of claim 1, wherein the depressive disorder is postpartum depression.

19. The method of claim 1, wherein the depressive disorder is a depressive disorder due to a medical condition.

20. The method of claim 1, wherein the compound is administered together with one or more sessions of psychotherapy or psychological support.

* * * * *